(12) United States Patent
Asada et al.

(10) Patent No.: US 10,077,247 B2
(45) Date of Patent: Sep. 18, 2018

(54) TRICYCLIC SPIRO COMPOUND

(71) Applicant: ONO PHARMACEUTICAL CO., LTD., Osaka (JP)

(72) Inventors: Masaki Asada, Osaka (JP); Kousuke Tani, Osaka (JP); Masaya Hirobe, Osaka (JP); Satonori Higuchi, Osaka (JP); Kazuhiro Fuchibe, Osaka (JP); Ryo Oikawa, Osaka (JP); Tohru Kotani, Osaka (JP); Hirotsugu Takano, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/542,216

(22) PCT Filed: Jan. 8, 2016

(86) PCT No.: PCT/JP2016/050446
§ 371 (c)(1),
(2) Date: Jul. 7, 2017

(87) PCT Pub. No.: WO2016/111347
PCT Pub. Date: Jul. 14, 2016

(65) Prior Publication Data
US 2018/0002308 A1 Jan. 4, 2018

(30) Foreign Application Priority Data

Jan. 9, 2015 (JP) .................. 2015-002712

(51) Int. Cl.
| | |
|---|---|
| *C07D 311/96* | (2006.01) |
| *C07D 405/14* | (2006.01) |
| *A61K 39/395* | (2006.01) |
| *A61K 45/00* | (2006.01) |
| *A61K 31/277* | (2006.01) |
| *A61K 31/343* | (2006.01) |
| *A61K 31/352* | (2006.01) |
| *A61K 31/381* | (2006.01) |
| *A61K 31/397* | (2006.01) |
| *A61K 31/4025* | (2006.01) |

(Continued)

(52) U.S. Cl.
CPC .............. *C07D 311/96* (2013.01); *A61K 9/20* (2013.01); *A61K 31/277* (2013.01); *A61K 31/343* (2013.01); *A61K 31/352* (2013.01); *A61K 31/381* (2013.01); *A61K 31/397* (2013.01); *A61K 31/4025* (2013.01); *A61K 31/415* (2013.01); *A61K 31/4155* (2013.01); *A61K 31/4192* (2013.01); *A61K 31/422* (2013.01); *A61K 31/427* (2013.01); *A61K 31/4245* (2013.01); *A61K 31/437* (2013.01); *A61K 31/4406* (2013.01); *A61K 31/4427* (2013.01); *A61K 31/4433* (2013.01); *A61K 31/4439* (2013.01); *A61K 31/453* (2013.01); *A61K 31/496* (2013.01); *A61K 31/497* (2013.01); *A61K 31/501* (2013.01); *A61K 31/506* (2013.01); *A61K 31/5383* (2013.01); *A61K 33/24* (2013.01); *A61K 39/395* (2013.01); *A61K 45/00* (2013.01); *A61K 45/06* (2013.01); *C07C 255/60* (2013.01); *C07C 255/63* (2013.01); *C07D 213/40* (2013.01); *C07D 213/56* (2013.01); *C07D 231/12* (2013.01); *C07D 231/40* (2013.01); *C07D 307/94* (2013.01); *C07D 401/04* (2013.01); *C07D 405/04* (2013.01); *C07D 405/12* (2013.01); *C07D 405/14* (2013.01); *C07D 407/12* (2013.01);

(Continued)

(58) Field of Classification Search
CPC .... C07D 311/96; C07D 311/94; C07D 311/74
See application file for complete search history.

(56) References Cited

U.S. PATENT DOCUMENTS

| | | |
|---|---|---|
| 6,242,493 B1 | 6/2001 | Gareau et al. |
| 2004/0152755 A1 | 8/2004 | He et al. |

(Continued)

FOREIGN PATENT DOCUMENTS

| | | |
|---|---|---|
| CN | 1653046 A | 8/2005 |
| CN | 102015639 A | 4/2011 |

(Continued)

OTHER PUBLICATIONS

Registry [STN online], Mar. 18, 2014, RN:1569670-12-7 Registry [STN online], Mar. 21, 2014, RN:1571324-24-8.

(Continued)

*Primary Examiner* — Samira J Jean-Louis
(74) *Attorney, Agent, or Firm* — Sughrue Mion, PLLC

(57) ABSTRACT

A medicinal agent for the prevention and/or treatment of diseases caused by $EP_4$ receptor activation. A compound having antagonistic activity against the $EP_4$ receptor is contained as an active ingredient in the medicinal agent. The compound represented by the following general formula (I) as defined in the specification, a salt, an N-oxide, or a solvate thereof, or a prodrug of these is useful as a medicinal component having antagonistic activity against the $EP_4$ receptor for the prevention and/or treatment of diseases caused by $EP_4$ receptor activation.

2 Claims, 1 Drawing Sheet

(51) Int. Cl.

| | |
|---|---|
| *A61K 31/415* | (2006.01) |
| *A61K 31/4155* | (2006.01) |
| *A61K 31/4192* | (2006.01) |
| *A61K 31/422* | (2006.01) |
| *A61K 31/4245* | (2006.01) |
| *A61K 31/427* | (2006.01) |
| *A61K 31/437* | (2006.01) |
| *A61K 31/4406* | (2006.01) |
| *A61K 31/4433* | (2006.01) |
| *A61K 31/4439* | (2006.01) |
| *A61K 31/453* | (2006.01) |
| *A61K 31/497* | (2006.01) |
| *A61K 31/501* | (2006.01) |
| *A61K 31/506* | (2006.01) |
| *A61K 31/5383* | (2006.01) |
| *A61K 33/24* | (2006.01) |
| *C07C 255/63* | (2006.01) |
| *C07D 307/94* | (2006.01) |
| *C07D 231/12* | (2006.01) |
| *C07D 405/12* | (2006.01) |
| *C07D 407/12* | (2006.01) |
| *C07D 409/12* | (2006.01) |
| *C07D 413/12* | (2006.01) |
| *C07D 417/12* | (2006.01) |
| *C07D 471/04* | (2006.01) |
| *C07D 498/04* | (2006.01) |
| *C07D 213/56* | (2006.01) |
| *A61K 9/20* | (2006.01) |
| *A61K 31/4427* | (2006.01) |
| *A61K 31/496* | (2006.01) |
| *A61K 45/06* | (2006.01) |
| *C07C 255/60* | (2006.01) |
| *C07D 213/40* | (2006.01) |
| *C07D 231/40* | (2006.01) |
| *C07D 401/04* | (2006.01) |
| *C07D 405/04* | (2006.01) |
| *C07D 409/04* | (2006.01) |
| *C07D 413/04* | (2006.01) |
| *C07D 417/04* | (2006.01) |

(52) U.S. Cl.
CPC ......... *C07D 409/04* (2013.01); *C07D 409/12* (2013.01); *C07D 413/04* (2013.01); *C07D 413/12* (2013.01); *C07D 417/04* (2013.01); *C07D 417/12* (2013.01); *C07D 471/04* (2013.01); *C07D 498/04* (2013.01); *C07C 2603/94* (2017.05)

(56) References Cited

U.S. PATENT DOCUMENTS

| | | |
|---|---|---|
| 2005/0124577 A1 | 6/2005 | Tani et al. |
| 2011/0059953 A1 | 3/2011 | Boeckler et al. |

FOREIGN PATENT DOCUMENTS

| | | |
|---|---|---|
| EP | 0544287 A1 | 6/1993 |
| EP | 1312601 A1 | 5/2003 |
| EP | 1431267 A1 | 6/2004 |
| JP | H 5-222049 A | 8/1993 |
| JP | 2002506851 A | 3/2002 |
| JP | 2002526517 A | 8/2002 |
| JP | 2004517099 A | 6/2004 |
| WO | 199947497 A2 | 9/1999 |
| WO | 200020371 A1 | 4/2000 |
| WO | 200216311 A1 | 2/2002 |
| WO | 200250032 A1 | 6/2002 |
| WO | 2003016254 A1 | 2/2003 |
| WO | 2004037247 A1 | 5/2004 |
| WO | 2013004290 A1 | 1/2013 |
| WO | 2015/000949 A1 | 1/2015 |

OTHER PUBLICATIONS

Manabu Negishi, et al., "Prostaglandin E receptors", Journal of Lipid Mediators and Cell Signalling, vol. 12, (1995), pp. 379-391.

Utako Yokoyama, et al., "The Prostanoid EP4 Receptor and Its Signaling Pathway", Pharmacological Reviews, vol. 65, Jul. 2013, pp. 1010-1052 URL: http://dx.doi.org/10.1124/pr.112.007195.

Kohanbash Gary, et al., "Abstract: LB-265, Title of Presentation: ONO-AE3-208 Inhibits Myeloid Derived Suppressor Cells and Glioma Growth", 105th Annual Meeting of American Association for Cancer Research (AACR), Date of Presentation: Apr. 8, 2014, Total 1 page.

Nobuhiro Nishigaki, et al., "Identification of prostaglandin E receptor 'EP2' cloned from mastocytoma cells as EP4 subtype", FEBS Letters, vol. 364, 15493 (1995), pp. 339-341.

Mousumi Majumder, et al.,"Prostaglandin E2 receptor EP4 as the common target on cancer cells and macrophages to abolish angiogenesis, lymphangiogenesis, metastasis, and stem-like cell fun", Cancer Science, vol. 105, 2014, pp. 1142-1151.

Naoki Terada, et al., "Identification of EP4 as a Potential Target for the Treatment of Castration-Resistant Prostate Cancer Using a Novel Xenograft Model", Cancer Research, vol. 70, No. 4, Feb. 15, 2010, pp. 1606-1615.

Michihiro Mutoh, et al., "Involvement of Prostaglandin E Receptor Subtype EP4 in Colon Carcinogenesis", Cancer Research, vol. 62, Jan. 1, 2002, pp. 28-32.

International Search Report dated Feb. 23, 2016, issued by the International Searching Authority in counterpart International Application No. PCT/JP2016/050446 (PCT/ISA/210).

Written Opinion dated Feb. 23, 2016, issued by the International Searching Authority in counterpart International Application No. PCT/JP2016/050446 (PCT/ISA/237).

Communication dated Nov. 24, 2017, from the European Patent Office in counterpart European Application No. 16735086.7.

Communication dated Jul. 13, 2018, from the State Intellectual Property Office of People's Republic of China in counterpart Application No. 201680005227.2.

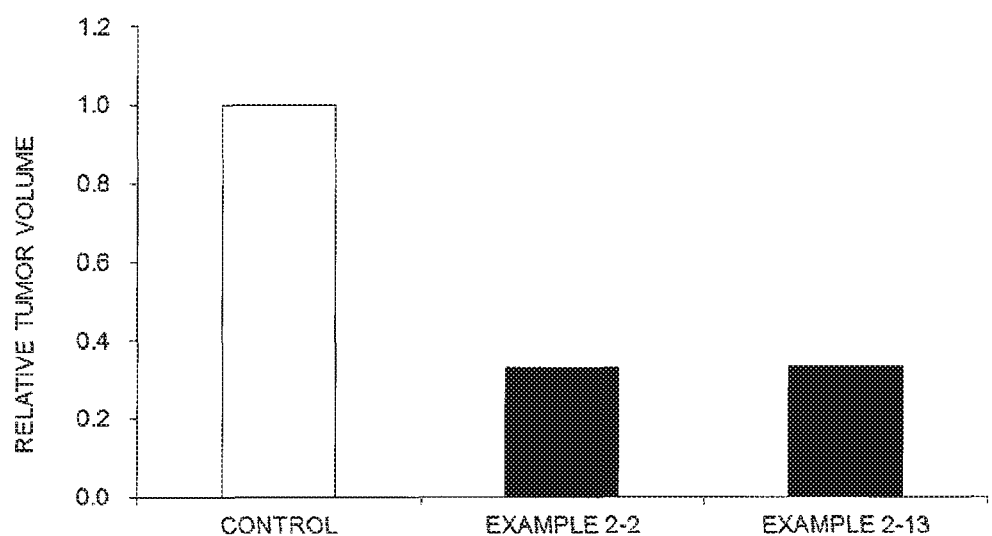

TRICYCLIC SPIRO COMPOUND

TECHNICAL FIELD

The present invention relates to an $EP_4$ receptor antagonist tricyclic spiro compound or a salt thereof, and to a medicament containing such a compound as an active ingredient. Specifically, the invention relates to a tricyclic spiro compound represented by the following general formula (I), a salt, an N-oxide, or a solvate thereof, or a prodrug of these (hereinafter, these will be referred to as "present compounds"), and to a medicament containing such a compound as an active ingredient.

(I)

The symbols used in general formula (I) are as defined below.

BACKGROUND ART

The prostaglandin $E_2$ ($PGE_2$) a known metabolite of the arachidonic acid cascade, is known to have a range of effects including cytoprotection, uterine contraction, lowering of the threshold of pain, promotion of peristalsis in the digestive tract, wakefulness, inhibition of stomach acid secretion, hypotensive effect, and diuretic effect.

Recent studies have found that there are subtypes of $PGE_2$ receptors with different roles. To date, four broad subtypes are known, and these are called $EP_1$, $EP_2$, $EP_3$, and $EP_4$ (Journal of Lipid Mediators and Cell Signalling, Vol. 12, p. 379-391, 1995).

In these subtypes, the $EP_4$ receptor is thought to be involved in inhibition of MCP-1 production from macrophages, inhibition of TNF-α, IL-2, and IFN-γ production from lymphocytes. This subtype is also believed to have involvement in anti-inflammation by enhanced IL-10 production, vasodilatation, angiogenesis, inhibition of elastic fiber formation, and regulation of MMP-9 expression. Other possible involvement of the $EP_4$ receptor includes immune control in cancer via myeloid derived suppressor cells, regulatory T cells, and natural killer cells.

It is therefore thought that compounds that strongly bind to the $EP_4$ receptor, and show antagonistic activity are useful for the prevention and/or treatment of diseases caused by $EP_4$ receptor activation, including, for example, a bone disease, a cancer, a systemic granulomatous disease, an immune disease, allergy, atopy, asthma, alveolar pyorrhea, gingivitis, periodontitis, Alzheimer's, Kawasaki disease, burn, multiple organ failure, chronic headache, pain, vasculitis, venous incompetence, varicose veins, aneurysm, aortic aneurysm, anal fistula, diabetes insipidus, stress, endometriosis, uterine adenomyosis, patent ductus arteriosus in neonates, and cholelithiasis (Pharmacological Reviews, Vol. 65, p. 1010-1052, July, 2013; 105th Annual Meeting of American Association for Cancer Research (AACR), Abstract: LB-265, Title of Presentation: ONO-AE3-208 inhibits Myeloid Derived Suppressor Cells and Glioma Growth, Date of Presentation: Apr. 8, 2014; FEBS Letters, Vol. 364, p. 339-341, 1995; Cancer Science, Vol. 105, p. 1142-1151, 2014; Cancer Research, Vol. 70, p. 1606-1615, 2010; and Cancer Research, Vol. 62, p. 28-32, 2002).

WO2000/020371 describes a compound of the following general formula (A) used for the treatment of diseases involving prostaglandin E receptors, for example, such as pain, inflammation, and cancer.

(A)

In the general formula (A), $Ar^{1a}$ is an aryl or a heteroaryl group optionally substituted with $R^{1a}$ or $R^{3a}$, wherein $R^{1a}$ is CN, $NO_2$, $CON(R^{5a})_2$, or the like;

$W^a$ represents a three- to six-membered linking group containing 0 to 2 heteroatoms selected from O, N, and S, wherein the linking group optionally contains CO, $S(O)_{na}$, C=C, or an acetylene group;

$Ar^{2a}$ is an aryl or a heteroaryl group optionally substituted with $R^{3a}$, wherein $R^{3a}$ is halogen, CN, or the like;

$X^a$ is a linker attached to $Ar^{2a}$ at the position ortho to the bonding site for $W^a$; and $Q^a$ is COOH or the like (These are only a part of the definitions of the groups.)

WO2003/016254 describes a compound of the following general formula (B) that binds to the $PGE_2$ receptor, particularly $EP_3$ and/or $EP_4$, and has antagonistic activity, useful for the prevention and/or treatment of diseases such as pain, and cancer.

(B)

In the general formula (B), $R^{1b}$ represents —COOH or the like;

$A^b$ represents (i) a single bond, (ii) C1-6 alkylene, (iii) C2-6 alkenylene, (iv) C2-6 alkynylene, or the like;

the ring $B^b$ represents a C3-12 monocyclic or bicyclic carbon ring, or a three- to twelve-membered monocyclic or bicyclic heterocyclic ring;

$R^{2b}$ represents nitro, cyano, or the like;

$Q^b$ represents C2-6 alkenyl, C2-6 alkynyl, C1-6 alkyl substituted with 1 to 3 halogen atoms, cyano, nitro, or the like;

$D^b$ is a one- or two-membered linking chain of atoms selected from a carbon atom, a nitrogen atom, an oxygen atom, and a sulfur atom, wherein the linking chain may contain a double bond or a triple bond, and may be substituted with one to four $R^{40b}$, wherein $R^{40b}$ represents an oxo, halogen, or the like; and $R^{3b}$ represents (1) C1-6 alkyl, or (2) a C3-15 monocyclic, bicyclic, or tricyclic carbon ring that is substituted with one to five $R^{42b}$, or that is unsubstituted, or a three- to fifteen-membered monocyclic, bicyclic, or tricyclic heterocyclic ring, wherein $R^{42b}$ represents C1-6 alkyl, C1-6 alkoxy, halogen, cyano, $-NR^{46b}COR^{47b}$, or $Cyc10^b$.

(These are only a part of the definitions of the groups.)

WO1999/047497 describes a compound of the following general formula (C) used for the treatment of diseases involving prostaglandin E receptors, for example, such as pain, inflammation, and cancer.

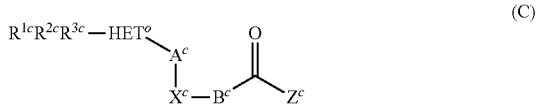

In the general formula (C), $HET^c$ represents a five- to twelve-membered monocyclic or bicyclic aromatic ring system having 0 to 3 heteroatoms selected from O, $S(O)_{nc}$, and $N(O)_{mc}$, wherein me is 0 or 1, and nc is 0, 1, or 2;

$A^c$ is one- or two-atom moiety and is selected from the group including $-W^c-$ and $-C(O)-$, wherein $W^c$ is O, $S(O)_{nc}$, or $NR^{17c}$;

$X^c$ represents a five- to ten-membered monocyclic or bicyclic aryl or heteroaryl group having 1 to 3 heteroatoms selected from O, $S(O)_{nc}$ and $N(O)_{mc}$, $Y^c$ represents O, $S(O)_{nc}$, $NR^{17c}$, a bond, or the like;

$B^c$ is $-(C(R^{18c})_2)_{pc}-Y^c-(C(R^{18c})_2)_{qc}-$, wherein pc and qc are independently 0 to 3;

$Z^c$ is OH, or the like; and $R^{1c}$, $R^{2c}$ and $R^{3c}$ independently represent halogen, $-CO_2R^{9c}$, $-CON(R^{6c})_2$, or the like.

(These are only a part of the definitions of the groups.)

None of these related art documents describe or suggest the present compound, specifically, the tricyclic spiro compound.

CITED REFERENCES

Patent Documents

PATENT DOCUMENT 1: WO2000/020371
PATENT DOCUMENT 2: WO2003/016254
PATENT DOCUMENT 3: WO1999/047497

Non-Patent Documents

NON-PATENT DOCUMENT 1: Journal of Lipid Mediators and Cell Signalling, Vol. 12, p. 379-391, 1995
NON-PATENT DOCUMENT 2: Pharmacological Reviews, Vol. 65, p. 1010-1052, July, 2013
NON-PATENT DOCUMENT 3: 105th Annual Meeting of American Association for Cancer Research (AACR), Abstract: LE-265, Title of Presentation: ONO-AE3-208 Inhibits Myeloid Derived Suppressor Cells and Glioma Growth, Date of Presentation: Apr. 8, 2014
NON-PATENT DOCUMENT 4: FEES Letters, Vol. 364, p. 339-341, 1995
NON-PATENT DOCUMENT 5: Cancer Science, Vol. 105, p. 1142-1151, 2014
NON-PATENT DOCUMENT 6: Cancer Research, Vol. 70, p. 1606-1615, 2010
NON-PATENT DOCUMENT 7: Cancer Research, Vol. 62, p. 28-32, 2002

DISCLOSURE OF THE INVENTION

Problems to be Solved by the Invention

The present invention is intended to create compounds that have a strong antagonistic activity against the $EP_4$ receptor, and show desirable pharmacokinetics, and to find a compound that is useful as a preventive and/or a therapeutic drug for diseases caused by $EP_4$ receptor activation.

Means for Solving the Problems

In order to achieve the foregoing object, the present inventors conducted intensive studies to find a compound that has a strong antagonistic activity against the $EP_4$ receptor, and shows desirable pharmacokinetics, and found that compounds represented by the general formula (I) below are a strong antagonist of the $EP_4$ receptor. The present invention was completed on the basis of this finding.

Specifically, an aspect of the present invention is as follows.

[1] A compound represented by the following general formula (I), or a salt, an N-oxide, or a solvate thereof, or a prodrug of these.

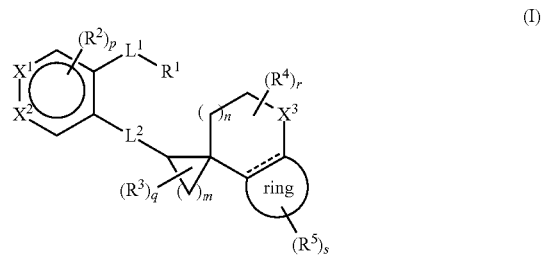

In the general formula (I), $R^1$ represents $COOR^8$, tetrazole, $SO_3H$, $SO_2NH_2$, $SO_2NHR^{8-1}$, $CONHSO_2R^{8-1}$, $SO_2NHCOR^{8-1}$, or hydroxamic acid, wherein $R^8$ represents a hydrogen atom, C1-4 alkyl, or benzyl, $R^{8-1}$ represents C1-4 alkyl, C1-4 haloalkyl, a C3-10 carbon ring, or a three- to ten-membered heterocyclic ring, wherein the C3-10 carbon ring, and the three- to ten-membered heterocyclic ring each may be substituted with C1-4 alkyl, C1-4 haloalkyl, C1-4 alkoxy, $-O(C1-4$ haloalkyl), C1-4 alkylthio, $-S(C1-4$ haloalkyl), halogen, or nitrile (here and below, "—CN"), $L^1$ represents C1-5 alkylene, C2-5 alkenylene, or C2-5 alkynylene, $R^2$ represents halogen, C1-4 alkyl, C1-4 alkoxy, C1-4 alkylthio, C2-4 alkenyl, C2-4 alkynyl, $-O(C1-4$ haloalkyl), $-S(C1-4$ haloalkyl), $-C(O)$ (C1-4 alkyl), $-SO_2(C1-4$ alkyl), $-CONH(C1-4$ alkyl), $-CON(C1-4$ alkyl)$_2$, $-NHC(O)(C1-4$ alkyl), $-N(C1-4$ alkyl)$C(O)$ (C1-4 alkyl), $-NHSO_2(C1-4$ alkyl), $-N(C1-4$ alkyl)$SO_2(C1-4$ alkyl), $-SO_2NH(C1-4$ alkyl), $-SO_2N(C1-4$ alkyl)$_2$, $-NR^{17}R^{17}$, nitro, nitrile, a hydroxyl group, aldehyde, or carboxyl, wherein the C1-4 alkyl each may be substituted with halogen, and wherein the (C1-4 alkyl)$_2$ represented by $R^2$ represents two independent C1-4 alkyl groups which may be the same or different, $X^1$ represents $CR^6$, or a nitrogen atom, wherein $R^6$ represents a hydrogen atom, or $R^2$, $X^2$ represents $CR^7$, or a nitrogen atom, wherein $R^7$ represents a hydrogen atom, $R^2$, or $-L^3-R^9$, wherein $L^3$ represents methylene, an oxygen atom, or a sulfur atom which may be oxidized, and $R^9$ represents a four- to ten-membered heterocyclic ring which may be substituted with a substituent selected from the group consisting of halogen, C1-4 alkyl, and C1-4 haloalkyl, $L^2$ represents —$CH_2CH_2$—, —CH=CH—, —$CH_2O$—, —$OCH_2$—, —$CH_2S$—, —$SCH_2$—, —$CH_2S(O)$—, —$S(O)CH_2$—, —$CH_2SO_2$—, —$SO_2CH_2$—, —$CH_2NH$—, —$NHCH_2$—, —NHCO—, —CONH—, —$NHSO_2$—, or —$SO_2NH$—, $R^3$ represents C1-4 alkyl, or halogen, $R^4$ represents halogen, C1-4 alkyl, or C1-4 haloalkyl, $X^3$ represents methylene, an oxygen atom, a sulfur atom which may be oxidized, or $NR^{10}$, wherein $R^{10}$ represents C1-4 alkyl, —C(O)(C1-4 alkyl), —C(O)O(C1-4 alkyl), or —$SO_2$ (C1-4 alkyl), wherein the C1-4 alkyl each may be substituted with halogen, the ring represents a benzene ring, or a five- to six-membered monocyclic aromatic heterocyclic ring, ===== represents a single bond, or a double bond, $R^5$ represents (1) halogen, (2) C1-4 alkyl, (3) carboxyl, (4) nitrile, (5) —$CONHR^{11}$, (6) —$C(O)R^{12}$, (7) —$OR^{14}$, (8) —$S(O)_rR^{15}$, (9) —$CH_2R^{16}$, (10) —$NR^{17}R^{17}$, (11) —$NHCOR^{11}$, (12) a C4-10 carbon ring, or (13) a four- to ten-membered heterocyclic ring, wherein the C4-10 carbon ring, or the four- to ten-membered heterocyclic ring may be substituted with one to three $R^{18}$, wherein, when a plurality of $R^{18}$ exists, the plurality of $R^{18}$ independently may be the same or different, $R^{11}$ represents C1-6 alkyl, C3-6 cycloalkyl, phenyl, or a four- to six-membered heterocyclic ring, and may be substituted with one to three $R^{13}$, wherein, when a plurality of $R^{13}$ exists, the plurality of $R^{13}$ independently may be the same or different, $R^{13}$ represents halogen, C1-6 alkyl, C3-6 cycloalkyl, C1-4 alkoxy, a hydroxyl group, —$NR^{20}R^{21}$, benzene, or a four- to six-membered heterocyclic ring, wherein $R^{20}$ and $R^{21}$ each independently represent a hydrogen atom, or C1-4 alkyl, $R^{12}$ represents C1-6 alkyl, C3-6 cycloalkyl, benzene, or a four- to six-membered heterocyclic ring, wherein the C3-6 cycloalkyl, the benzene, and the Lour- to six-membered heterocyclic ring each independently may be substituted with halogen, C1-4 alkyl, or C1-4 alkoxy, $R^{14}$ represents a hydrogen atom, C1-6 alkyl, C3-6 cycloalkyl, benzene, or benzyl, wherein the C1-6 alkyl may be substituted with one to three $R^{19}$, wherein, when a plurality of $R^{19}$ exists, the plurality of $R^{19}$ independently may be the same or different, $R^{19}$ represents C1-4 alkoxy, —CONH(C1-4 alkyl), —CON(C1-4 alkyl)$_2$, or a five- to six-membered monocyclic aromatic heterocyclic ring which may be substituted with a substituent selected from the group consisting of C1-4 alkyl, and C1-4 haloalkyl, wherein the (C1-4 alkyl)$_2$ represented by $R^{19}$ represents two independent C1-4 alkyl groups which may be the same or different, $R^{15}$ represents C1-6 alkyl, C3-6 cycloalkyl, benzene, or benzyl, $R^{16}$ represents a hydroxyl group, or C1-4 alkoxy, $R^{17}$ each independently represent a hydrogen atom, C1-6 alkyl, or C3-6 cycloalkyl, $R^{18}$ represents halogen, C1-6 alkyl, C3-6 cycloalkyl, C1-4 alkoxy, oxo, nitrile, a hydroxyl group, hydroxymethyl, 1-methyl-1-hydroxyethyl, (C1-4 alkyl)$SO_2$—, a four- to six-membered heterocyclic ring, (C1-4 alkyl)NH—, or (C1-4 alkyl)$_2$N—, wherein the (C1-4 alkyl)$_2$ represented by $R^{18}$ represents two independent C1-4 alkyl groups which may be the same or different, m represents an integer of 1 to 4, n represents an integer of 0 to 4, p represents an integer of 0 to 2, q represents an integer of 0 to 6, r represents an integer of 0 to 6, s represents an integer of 0 to 4, t represents an integer of 0 to 2, and $R^2$, $R^3$, $R^4$, and $R^5$ each independently may be the same or different when p, g, r, and s are each an integer of 2 or more.

[2] The compound according to item [1], which is represented by the following general formula (I-1),

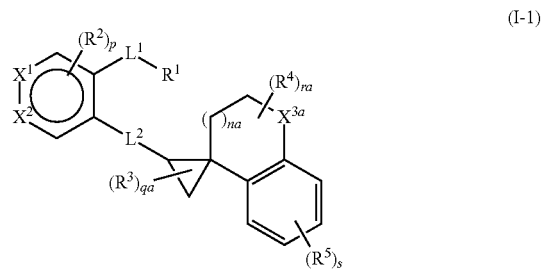

(I-1)

wherein na represents an integer of 0 to 1, qa represents an integer of 0 to 3, ra represents an integer of 0 to 4, $X^{3a}$ represents methylene, or an oxygen atom, and the other symbols are as defined in item [1].

[3] The compound according to item [1] or [2], wherein at least one $R^5$ is —$CONHR^{11}$.

[4] The compound according to any one of items [1] to [3], wherein $L^2$ is —NHCO—, —CONH—.

[5] The compound according to any one of items [1] to [4], which is represented by the following general formula (I-2),

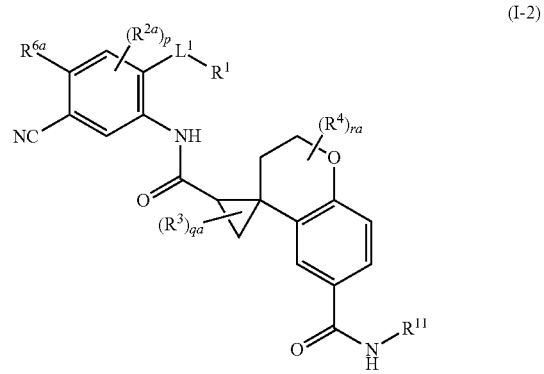

(I-2)

wherein $R^{2a}$ represents halogen, represents a hydrogen atom, or halogen, and the other symbols are as defined in items [1] and [2].

[6] The compound according to item [1], which is anyone of the following:

(1) 4-[4-cyano-2-({[(2'R,4S)-6-(methylcarbamoyl)-2,3-dihydrospiro[chromene-4,1'-cyclopropan]-2'-yl]carbonyl}amino)phenyl]butanoic acid, (2) 4-{4-cyano-2-[({(2'R,4S)-6-[(cyclopropylmethyl)carbamoyl]-2,3-dihydrospiro[chromene-4,1'-cyclopropan]-2'-yl}carbonyl)amino]phenyl}butanoic acid, (3) 4-{4-cyano-2-[({(2'R,4S)-6-[(2-methoxyethyl)carbamoyl]-2,3-dihydrospiro[chromene-4,1'-cyclopropan]-2'-yl}carbonyl)amino]phenyl}butanoic acid, (4) 4-{4 cyano-2-[({(2'R,4S)-6-[(2-methyl-2-propanyl)carbamoyl]-2,3-dihydrospiro[chromene-4,1'-cyclopropan]-2'-yl}carbonyl)amino]phenyl}butanoic acid, (5) 4-[4-cyano-2-({[(2'R,4S)-6-{[(2S)-1-methoxy-2-propanyl]carbamoyl}-2,3-dihydrospiro[chromene-4,1'-cyclopropan]-2'-yl]carbonyl}amino)phenyl]butanoic acid, (6) 4-{4-cyano-2-[({(2'R,4S)-6-[(1-methyl-1H-pyrazol-3-yl)carbamoyl]-2,3-dihydrospiro[chromene-4,1'-cyclopropan]-2'-yl}carbonyl)amino]phenyl}butanoic acid, (7) 4-[4-cyano-2-({[(2'R,4S)-6-(cyclopropylcarbamoyl)-2,3-dihydrospiro[chromene-4,1'-cyclopropan]-2'-yl]carbonyl}amino)phenyl]butanoic acid, (8) 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, (9) 4-[4-cyano-2-({[(2'R,4S) (cyclopentylcarbamoyl)-2,3-dihydrospiro[chromene-4,1'-cyclopropan]-2'-yl]carbonyl}amino)phenyl]butanoic acid,

(10) 4-{2-[({(2'R,4S)-6-[(2S)-2-butanylcarbamoyl]-2,3-dihydrospiro[chromene-4,1'-cyclopropan]-2'-yl}carbonyl)amino]-4-cyanophenyl}butanoic acid,

(11) 4-{4-cyano-2-[({(2'R,4S)-6-[(trans-4-hydroxycyclohexyl)carbamoyl]-2,3-dihydrospiro[chromene-4,1'-cyplopropan]-2'-yl}carbonyl)amino]phenyl}butanoic acid,

(12) 4-{4-cyano-2-[({(2°R,4S)-6-[(cis-4-hydroxycyclohexyl)carbamoyl]-2,3-dihydrospiro[chromene-4,1'-cyclopropan]-2'-yl}carbonyl)amino]phenyl}butanoic acid,

(13) 4-[4-cyano-2-({[(2'R,4S)-6-(2-pyridinylcarbamoyl)-2,3-dihydrospiro[chromene-4,1'-cyclopropan]-2'-yl]carbonyl}amino)phenyl]butanoic acid,

(14) 4-[4-cyano-2-({[(2'R,4S)-6-(3-pyridazinylcarbamoyl)-2,3-dihydrospiro[chromene-4,1'-cyclopropan]-2'-yl]carbonyl}amino)phenyl]butanoic acid,

(15) 4-[4-cyano-2-({[(2'R,4S)-6-(cyclobutylcarbamoyl)-2,3-dihydrospiro[chromene-4,1'-cyclopropan]-2'-yl]carbonyl}amino)phenyl]butanoic acid,

(16) 4-[4-cyano-2-({[(2'R,4S)-6-{[1-(2-methyl-2-propanyl)-1H-pyrazol-4-yl]carbamoyl}-2,3-dihydrospiro[chromene-4,1'-cyclopropan]-2'-yl]carbonyl}amino)phenyl]butanoic acid,

(17) 4-[4-cyano-2-({[(2'R,4S)-6-(tetrahydro-2H-pyran-4-ylcarbamoyl)-2,3-dihydrospiro[chromene-4,1'-cyclopropan]-2'-yl]carbonyl}amino)phenyl]butanoic acid,

(18) 4-[4-cyano-2-({[(2'R,4S)-6-(propylcarbamoyl)-2,3-dihydrospiro[chromene-4,1'-cyclopropan]-2'-yl]carbonyl}amino)phenyl]butanoic acid,

(19) 4-{4-cyano-2-[({(2'R,4S)-6-[(2-ethoxyethyl) carbamoyl]-2,3-dihydrospiro[chromene-4,1'-cyclopropan]-2'-yl}carbonyl)amino]phenyl}butanoic acid,

(20) 4-[4-cyano-2-({[(2'R,4S)-6-(ethylcarbamoyl)-2,3-dihydrospiro[chromene-4,1'-cyclopropan]-2'-yl]carbonyl}amino)phenyl]butanoic acid,

(21) 4-[4-cyano-2-({[(1R,2R)-6'-(methylcarbamoyl)-2',3'-dihydrospiro[cyclopropane-1,1'-inden]-2-yl]carbonyl}amino)phenyl]butanoic acid,

(22) 4-{4-cyano-2-[({(1R,2R)-6'-[(2-methoxyethyl)carbamoyl]-2',3'-dihydrospiro[cyclopropane-1,1'-inden]-2-yl}carbonyl)amino]phenyl}butanoic acid,

(23) 4-{4-cyano-2-[({(1R,2R)-6'-[(1-methyl-1H-pyrazol-4-yl)carbamoyl]-2',3'-dihydrospiro[cyclopropane-1,1'-inden]-2-yl}carbonyl)amino]phenyl}butanoic acid,

(24) 4-[4-cyano-2-({[(2'R,4S)-7-fluoro-6-(methylcarbamoyl)-2,3-dihydrospiro[chromene-4,1'-cyclopropan]-2'-yl]carbonyl}amino)phenyl]butanoic acid,

(25) 4-{4-cyano-2-[({(2'R,4S)-7-fluoro-6-[(2-methoxyethyl)carbamoyl]-2,3-dihydrospiro[chromene-4,1'-Cyclopropan]-2'-yl}carbonyl)amino]phenyl}butanoic acid,

(26) 4-[4-cyano-2-({[(2'R,4S)-7-fluoro-6-(isopropylcarbamoyl)-2,3-dihydrospiro[chromene-4,1'-cyclopropan]-2'-yl]carbonyl}amino)phenyl]butanoic acid,

(27) 4-[4-cyano-2-({[(2'R,4S)-7-(methylcarbamoyl)-2,3-dihydrospiro[chromene-4,1'-cyclopropan]-2'-yl]carbonyl}amino)phenyl]butanoic acid,

(28) 4-{4-cyano-2-[({(2'R,4S)-7-[(2-methoxyethyl)carbamoyl]-2,3-dihydrospiro[chromene-4,1'-cyclopropan]-2'-yl}carbonyl)amino]phenyl}butanoic acid,

(29) 4-[4-cyano-2-({[(2'R,4S)-7-methoxy-6-methylcarbamoyl)-2,3-dihydrospiro[chromene-4,1'-cyclopropan]-2'-yl]carbonyl}amino)phenyl]butanoic acid,

(30) 4-{4-cyano-2-[({(2'R,4S)-7-methoxy-6-[(2-methoxyethyl)carbamoyl]-2,3-dihydrospiro[chromene-4,1'-cyclopropan]-2'-yl}carbonyl)amino]phenyl}butanoic acid,

(31) 4-[4-cyano-2-({[(2'R,3S)-5-(methylcarbamoyl)spiro[1-benzofuran-3,1'-cyclopropan]-2'-yl]carbonyl}amino)phenyl]butanoic acid,

(32) 4-{4-cyano-2-[({(2'R,3S)-5-[(2-methoxyethyl)carbamoyl]spiro[1-benzofuran-3,1'-cyclopropan]-2'-yl}carbonyl)amino]phenyl}butanoic acid,

(33) 4-[4-cyano-2-({[(1S,2R)-6'-[(2-methoxyethyl)carbamoyl]-3,3'-dimethyl-2',3'-dihydrospiro[cyclopropane-1,1'-inden]-2-yl]carbonyl}amino)phenyl]butanoic acid, and

(34) 4-[4-cyano-2-({[(1S,2R)-3',3'-dimethyl-6'-(methylcarbamoyl)-2',3'-dihydrospiro[cyclopropane-1,1'-inden]-2-yl]carbonyl}amino)phenyl]butanoic acid.

[7] The compound according to item [1] or [2], wherein at least one $R^5$ is a C4-10 carbon ring which may be substituted with one to three $R^{18}$, or a four- to ten-membered heterocyclic ring which may be substituted with one to three $R^{18}$, wherein, when a plurality of $R^{18}$ exists, the plurality of $R^{18}$ each independently may be the same or different.

[8] The compound according to item [7], wherein $L^2$ is —NHCO—, or —CONH—.

[9] The compound according to any one of items [1], [2], [7], and [8], which is represented by the following general formula (I-3),

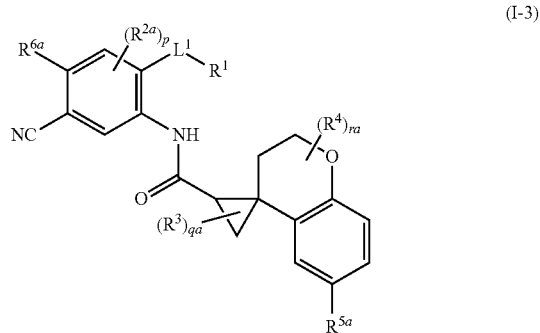

wherein $R^{5a}$ is a C4-10 carbon ring which may be substituted with one to three $R^{18}$, or a four- to ten-membered heterocyclic ring which may be substituted with one to three $R^{18}$, wherein, when a plurality of $R^{18}$ exists, the plurality of $R^{18}$ each independently may be the same or different, and the other symbols are as defined in items [I], [2], and [5].

[10] The compound according to item [1], which is any one of the following:

(1) 4-[4-cyano-2-({[(2'R,4S)-6-(5-methyl-1,3,4-oxadiazol-2-yl)-2,3-dihydrospiro[chromene-4,1'-cyclopropan]-2'-yl]carbonyl}amino)phenyl]butanoic acid,
(2) 4-[4-cyano-2-({[(2'R,4S)-6-(5-cyclopropyl-1,3,4-oxadiazol-2-yl)-2,3-dihydrospiro[chromene-4,1'-cyclopropan]-2'-yl]carbonyl}amino)phenyl]butanoic acid,
(3) 4-[4-cyano-2-({[(2'R,4S)-6-(3-methyl-1,2,4-oxadiazol-5-yl)-2,3-dihydrospiro[chromene-4,1'-cyclopropan]-2'-yl]carbonyl}amino)phenyl]butanoic acid,
(4) 4-[4-cyano-2-({[(2'R,4S)-6-(3-pyridinyl)-2,3-dihydrospiro[chromene-4,1'-cyclopropan]-2'-yl]carbonyl}amino)phenyl]butanoic acid,
(5) 4-[4-cyano-2-({[(2'R,4S)-6-(1H-pyrazol-1-yl)-2,3-dihydrospiro[chromene-4,1'-cyclopropan]-2'-yl]carbonyl}amino)phenyl]butanoic acid,
(6) 4-[4-cyano-2-({[(2'R,4S)-6-(1H-pyrazol-5-yl)-2,3-dihydrospiro[chromene-4,1'-cyclopropan]-2'-yl]carbonyl}amino)phenyl]butanoic acid,
(7) 4-[4-cyano-2-({[(2'R,4S)-6-(4-pyridazinyl)-2,3-dihydrospiro[chromene-4,1'-cyclopropan]-2'-yl]carbonyl}amino)phenyl]butanoic acid,
(8) 4-[4-cyano-2-({[(2'R,4S)-6-(2-oxo-1-pyrrolidinyl)-2,3-dihydrospiro[chromene-4,1'-cyclopropan]-2'-yl]carbonyl}amino)phenyl]butanoic acid,
(9) 4-[4-cyano-2-({[(2'R,4S)-6-(6-methoxy-3-pyridinyl)-2,3-dihydrospiro[chromene-4,1'-cyclopropan]-2'-yl]carbonyl}amino)phenyl]butanoic acid,
(10) 4-{4-cyano-2-[({(2'R,4S)-6-[6-(1H-pyrazol-1-yl)-3-pyridinyl]-2,3-dihydrospiro[chromene-4,1'-cyclopropan]-2'-yl}carbonyl)amino]phenyl}butanoic acid,
(11) 4-{4-cyano-2-[({(2'R,4S)-6-[6-(dimethylamino)-3-pyridinyl]-2,3-dihydrospiro[chromene-4,1'-cyclopropan]-2'-yl}carbonyl)amino]phenyl}butanoic acid,
(12) 4-[4-cyano-2-({[(2'R,4S)-6-(6-methyl-3-pyridinyl)-2,3-dihydrospiro[chromene-4,1'-cyclopropan]-2'-yl]carbonyl}amino)phenyl]butanoic acid,
(13) 4-{4-cyano-2-[({(2'R,4S)-6-[6-(methylamino)-3-pyridinyl]-2,3-dihydrospiro[chromene-4,1'-cyclopropan]-2'-yl}carbonyl)amino]phenyl}butanoic acid,
(14) 4-[4-cyano-2-({[(2'R,4S)-6-(2-pyridinyl)-2,3-dihydrospiro[chromene-4,1'-cyclopropan]-2'-yl]carbonyl}amino)phenyl]butanoic acid,
(15) 4-[4-cyano-2-({[(2'R,4S)-6-(1,3-thiazol-2-yl)-2,3-dihydrospiro[chromene-4,1'-cyclopropan]-2'-yl]carbonyl}amino)phenyl]butanoic acid,
(16) 4-[4-cyano-2-({[(2'R,4S)-6-(1,3-oxazol-2-yl)-2,3-dihydrospiro[chromene-4,1'-cyclopropan]-2'-yl]carbonyl}amino)phenyl]butanoic acid,
(17) 4-[4-cyano-2-({[(2'R,4S)-6-(1-methyl-1H-1,2,3-triazol-4-yl)-2,3-dihydrospiro[chromene-4,1'-cyclopropan]-2'-yl]carbonyl}amino)phenyl]butanoic acid,
(18) 4-[4-cyano-2-({[(2'R,4S)-6-(3-pyridazinyl)-2,3-dihydrospiro[chromene-4,1'-cyclopropan]-2?-yl]carbonyl}amino)phenyl]butanoic acid,
(19) 4-[4-cyano-2-({[(2'R,3S)-5-(3-pyridinyl)spiro[1-benzofuran-3,1'-cyclopropan]-2'-yl]carbonyl}amino)phenyl]butanoic acid, and
(20) 4-[4-cyano-2-({[(1S,2R)-3',3'-dimethyl-6'-(3-pyridinyl)-2',3'-dihydrospiro[cyclopropane-1,1'-inden]-2-yl]carbonyl}amino)phenyl]butanoic acid.

[11] pharmaceutical composition comprising the compound of general formula (I) according to item [1], a salt, an N-oxide, or a solvate thereof, or a prodrug of these as an active ingredient.

[12] The composition according to item [11], which is an $EP_4$ receptor antagonist.

[13] The composition according to item [11], which is a preventive and/or a therapeutic agent against a disease caused by $EP_4$ receptor activation.

[14] The composition according to item [13], wherein the disease caused by $EP_4$ receptor activation is a bone disease, a cancer, a systemic granulomatous disease, an immune disease, alveolar pyorrhea, gingivitis, periodontitis, Kawasaki disease, multiple organ failure, chronic headache, pain, vasculitis, venous incompetence, varicose veins, aneurysm, aortic aneurysm, anal fistula, diabetes insipidus, patent ductus arteriosus in neonates, or cholelithiasis.

[15] The composition according to item [14], wherein the cancer is breast cancer, ovarian cancer, colorectal cancer, lung cancer, prostate cancer, head and neck cancer, lymphoma, uveal melanoma, thymoma, mesothelioma, esophageal cancer; stomach cancer, duodenal cancer, hepatocellular carcinoma, cholangiocarcinoma, gallbladder cancer, pancreatic cancer, renal cell carcinoma, renal pelvis and ureter cancer, bladder cancer, penile cancer, testicular cancer, uterus cancer, vaginal cancer, vulvar cancer, skin cancer, malignant bone tumor, soft tissue sarcoma, chondrosarcoma, leukemia, myelodysplastic syndrome, or multiple myeloma.

[16] A medicament comprising the compound of general formula (I) according to item [1], a salt, an N-oxide, or a solvate thereof, or a prodrug of these with at least one selected from an alkylating agent, an antimetabolite, an anti-cancer antibiotic, a plant-based preparation, a hormonal agent, a platinum compound, a topoisomerase inhibitor, a kinase inhibitor, an anti-C120 antibody, an anti-HER2 antibody, an anti-EGFR antibody, an anti-VEGF antibody, a proteasome inhibitor, an HDAC inhibitor, and an immunomodulator.

[17] A medicament comprising the compound of general formula (I) according to item [1], a salt, an N-oxide, or a solvate thereof, or a prodrug of these with at least one selected from an HMG-CoA reductase inhibitor, an antihypertensive, and a tetracycline antibiotic.

[18] A medicament comprising the compound of general formula (I) according to item [1], a salt, an N-oxide, or a solvate thereof, or a prodrug of these with at least one selected from an N-type calcium channel inhibitor, a Nitric oxide synthetase (NOS) inhibitor, and a cannabinoid-2 receptor stimulating reagent.

[19] A method for preventing and/or treating a disease caused by $EP_4$ receptor activation,
the method comprising administering an effective amount of the compound of general formula (I) according to item [1], a salt, an N-oxide, or a solvate thereof, or a prodrug of these to a patient in need of prevention and/or treatment of a disease caused by $EP_4$ receptor activation.

[20] The compound of general formula (I) according to item [1], a salt, an N-oxide, or a solvate thereof, or a prodrug of these for prevention and/or treatment of a disease caused by $EP_4$ receptor activation.

[21] Use of the compound of general formula (I) according to item [1], a salt, an N-oxide, or a solvate thereof for production of a preventive and/or a therapeutic agent against a disease caused by $EP_4$ receptor activation.

Effect of the Invention

The present compound has a strong antagonistic activity against the $EP_4$ receptor, and shows desirable pharmacokinetics. The present compound has use as a preventive and/or a therapeutic drug against diseases caused by $EP_4$ receptor activation.

BRIEF DESCRIPTION OF THE DRAWING

FIG. 1 is a diagram representing the anti-tumor effect of the present compounds in an allograft model of mouse colorectal cancer cell line CT26.

EMBODIMENTS FOR CARRYING OUT THE INVENTION

The present invention is described below in detail.

In the present invention, "C1-4 alkyl" is, for example, methyl, ethyl, n-propyl, isopropyl, n-butyl, sec-butyl, tert-butyl, or isobutyl.

In the present invention, "C1-3 alkyl" is, for example, methyl, ethyl, n-propyl, or isopropyl.

In the present invention, "C1-5 alkylene" is, for example, methylene, ethylene, propylene, butylene, or pentylene.

In the present invention, "C2-5 alkenylene" is, for example, ethenylene, 1-propenylene, 2-propenylene, 1-butenylene, 2-butenylene, 3-butenylene, 1-pentenylene, 2-pentenylene, 3-pentenylene, or 4-pentenylene.

In the present invention, "C2-5 alkynylene" is, for example, ethynylene, 1-propynylene, 2-propynylene, 1-butynylene, 2-butynylene, 3-butynylene, 1-pentynylene, 2-pentynylene, 3-pentynylene, or 4-pentynylene.

In the present invention, "halogen" is fluorine, chlorine, bromine, or iodine.

In the present invention, "C1-4 alkoxy" is, for example, methoxy, ethoxy, propoxy, isopropoxy, butoxy, 1-methylpropoxy, tert-butoxy, or isobutoxy.

In the present invention, "C1-4 alkylthio" is, for example, methylthio, ethylthio, propylthio, isopropylthio, butylthio, 1-methylpropylthio, tert-butylthio, or isobutylthio.

In the present invention, "C2-4 alkenyl" is, for example, ethenyl, 1-propenyl, 2-propenyl, 1-butenyl, 2-butenyl, or 3-butenyl.

In the present invention, "C2-4 alkynyl" is, for example, ethynyl, 1-propynyl, 2-propynyl, 1-butynyl, 2-butynyl, or 3-butynyl.

In the present invention, "C1-4 haloalkyl" represents halogen-substituted C1-4 alkyl, and is, for example, monofluoromethyl, difluoromethyl, trifluoromethyl, 2-fluoroethyl, 1-fluoroethyl, 2,2-difluoroethyl, 1,2-difluoroethyl, 1,1-difluoroethyl, 2,2,2-trifluoroethyl, 1,2,2-trifluoroethyl, 1,1,2-trifluoroethyl, 1,2,2,2-tetrafluoroethyl, 1,1,2,2-tetrafluoroethyl, pentafluoroethyl, 1,2-dibromo-1,2,2-trifluoroethyl, 1-chloro-1,2,2,2-tetrafluoroethyl, 3-fluoropropyl, 3-chloropropyl, 2-fluoropropyl, 2-chloropropyl, 1-fluoropropyl, 1-chloropropyl, 3,3-difluoropropyl, 2,3-difluoropropyl, 1,3-difluoropropyl, 1,2-difluoropropyl, 2,2-difluoropropyl, 1,1-difluoropropyl, 3,3,3-trifluoropropyl, 2,3,3-trifluoropropyl, 1,3,3-trifluoropropyl, 1,2,2-trifluoropropyl, 1,1,2-trifluoropropyl, 1,1,3-trifluoropropyl, 1,1,2,2-tetrafluoropropyl, 2,2,3,3,3-pentafluoropropyl, 4-fluorobutyl, 4-chlorobutyl, 3-fluorobutyl, 3-chlorobutyl, 2-fluorobutyl, 2-chlorobutyl, 1-fluorobutyl, 1-chlorobutyl, 3,3-difluorobutyl, 2,3-difluorobutyl, 1,3-difluorobutyl, 1,2-difluorobutyl, 2,2-difluorobutyl, 1,1-difluorobutyl, 3,3,3-trifluorobutyl, 2,3,3-trifluorobutyl, 1,3,3-trifluorobutyl, 1,2,2-trifluorobutyl, 1,1,2-trifluorobutyl, 1,1,3-trifluorobutyl, 1,1,2,2-tetrafluorobutyl, or 2,2,3,3,3-pentafluorobutyl.

In the present invention, "sulfur that may be oxidized" represents sulfur (S), sulfoxide (S(O)), or sulfone (SO$_2$).

In the present invention, "four- to ten-membered heterocyclic ring" means a four- to ten-membered monocyclic or bicyclic heterocyclic ring containing 1 to 5 heteroatoms selected from an oxygen atom; a nitrogen atom, and a sulfur atom, and is, for example, an oxetane, azetidine, pyrrolidine, pyrrole, imidazole, triazole, tetrazole, pyrazole, pyridine, piperidine, piperazine, pyrazine, pyrimidine, pyridazine, azepine, diazepine, furan, pyran, oxepin, thiophene, thiopyran, thiepine, oxazole, isoxazole, isooxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, iso benzofuran, benzothiophene, isobenzothiophene, indazole, quinoline, isoquinoline, quinolizine, purine, phthalazine, pteridin, naphthyridine, quinoxaline, quinazoline, cinnoline, benzooxazole, benzothiazole, benzoimidazole, benzodioxole, benzooxathiol, chromene, benzofurazan, benzothiadiazole, benzotriazole, pyrroline, pyrrolidine, imidazoline, imidazolidine, triazoline, triazolidine, tetrazoline, tetrazolidine, pyrazoline, pyrazolidine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisooxazole, tetrahydroisooxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, tetrahydrotriazolopyrazine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzooxathiane, dihydrobenzooxazine, dihydrobenzothiazine, pyrazinomorpholine, dihydrobenzooxazole, perhydrobenzooxazole, ddhydrobenzothiazole, perhydrobenzothiazole, dihydrobenzoimidazole, perhydrobenzoimidazole, dioxolan, dioxane, dioxaindan, benzodioxane, thiochromane, dihydrobenzodioxine, dihydrobenzoxathiin, chromane, pyrazolopyrimidine, imidazopyridazine, imidazopyridine, imidazopyrimidine, pyrrolopyridine, pyrrolopyrimidine, pyrrolopyridazine, imidazopyrazine, pyrazolopyridine, pyrazolopyrimidine, triazcicpyridine, or dihydropyridcoxazine ring.

In the present invention, "three- to ten-membered heterocyclic ring" means a three- to ten-membered monocyclic or bicyclic heterocyclic ring containing 1 to 5 heteroatoms selected from an oxygen atom, a nitrogen atom, and a sulfur atom, and is, for example, aziridine, oxirane, thiirane, or any of the heterocyclic rings exemplified above for the "four- to ten-membered heterocyclic ring."

In the present invention, "five- to ten-membered aromatic heterocyclic ring" means a five- to ten-membered monocyclic or bicyclic aromatic heterocyclic ring containing 1 to 4 heteroatoms selected from an oxygen atom, a nitrogen atom, and a sulfur atom, and is, for example, a pyrrole, imidazole, triazole, tetrazole, pyrazole, furan, thiophene, oxazole, isooxazole, thiazole, isothiazole, furazan, oxadiazole, thiadiazole, pyridine, pyrazine, pyrimidine, pyridazine, indole, isoindole, benzofuran, isobenzofuran, benzothiophene, isobenzothiophene, indazole, purine, benzooxazole, benzothiazole, benzoimidazole, benzofurazan, benzothiadiazole, benzotriazole, quinoline, isoquinoline, phthalazine, pteridin, naphthyridine, quinoxaline, quinazoline, or cinnoline ring.

In the present invention, "five- to six-membered monocyclic aromatic heterocyclic ring" is, for example, a pyrrole, imidazole, triazole, tetrazole, pyrazole, pyridine, pyrazine, pyrimidine, pyridazine, furan, thiophene, oxazole, isooxazole, thiazole, isothiazole, furazan, oxadiazole, or thiadiazole ring.

In the present invention, "C4-10 carbon ring" means a C4 to 10 monocyclic or bicyclic carbon ring, and is, for example, a cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, or perhydronaphthalene ring.

In the present invention, "C3-10 carbon ring" means a C3 to 10 monocyclic or bicyclic carbon ring, and is, for example, cyclopropane, or any of the carbon rings exemplified above for the "C4-10 carbon ring."

In the present invention, "C1-6 alkyl" is, for example, methyl, ethyl, n-propyl, isopropyl, n-butyl, sec-butyl, tert-butyl, isobutyl, pentyl, 1-methylbutyl, 2-methylbutyl, 3-methylbutyl, 1,1-dimethylpropyl, 1,2-dimethylpropyl, 2,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 1-methyl-1-ethylpropyl, 2-methyl-2-ethylpropyl, 1-ethylbutyl, 2-ethylbutyl, or 1,1-dimethylpentyl.

In the present invention, "C3-6 cycloalkyl" cyclopropyl, cyclobutyl, cyclopentyl, or cyclohexyl.

In the present invention, "four- to six-membered heterocyclic ring" means a four- to six-membered monocyclic heterocyclic ring containing 1 to 4 heteroatoms selected from an oxygen atom, a nitrogen atom, and a sulfur atom, and is, for example, an oxetane, azetidine, pyrrolidine, piperidine, pyrazine, pyran, thiopyran, oxazine, oxadiazine, thiazine, thiadiazine, pyrrole, imidazole, triazole, tetrazole, pyrazole, pyridine, pyrimidine, pyridazine, furan, thiophene, oxazole, isooxazole, thiazole, isothiazole, furazan, oxadiazole, or thiadiazole ring.

In the present invention, $R^1$ is preferably $COOR^8$.

In the present invention, $R^8$ is preferably a hydrogen atom, or C1-4 alkyl, more preferably a hydrogen atom.

In the present invention, $R^{8-1}$ is preferably C1-4 alkyl, benzene, or pyridine. The benzene and the pyridine may be substituted with C1-4 alkyl, C1-4 haloalkyl, C1-4 alkoxy, —O(C1-4 haloalkyl), C1-4 alkylthio, —S(C1-4 haloalkyl), halogen, or nitrile, In the present invention, $L^1$ is preferably C1-5 alkylene, or C2-5 alkenylene, more preferably C1-5 alkylene, particularly preferably propylene.

In the present invention, $R^2$ is preferably fluorine.

In the present invention, $X^1$ is preferably $CR^6$.

In the present invention, $R^6$ is preferably a hydrogen atom, or fluorine, more preferably a hydrogen atom.

In the present invention, $X^2$ is preferably $CR^7$.

In the present invention, $R^7$ is preferably fluorine, nitrile, —$CH_2R^9$, or —$OR^9$, more preferably nitrile.

In the present invention, $R^9$ is preferably a four- to ten-membered heterocyclic ring which may be substituted with methyl or trifluoromethyl. The four- to ten-membered heterocyclic ring is preferably a five- to ten-membered aromatic heterocyclic ring, more preferably a five- to ten-membered nitrogen-containing aromatic heterocyclic ring (for example, pyrazole, imidazole, triazole, pyrrolopyridine, pyrrolopyrimidine, pyrrolopyridazine, imidazopyridazine, imidazopyridine, imidazopyrimidine, imidazopyrazine, pyrazolopyridine, or pyrazolopyrimidine).

In the present invention, $L^2$ is preferably —CH═CH—, —NHCO—, —CONH—, —NHSO$_2$—, or —SO$_2$NH—, more preferably —NHCO—, or —CONH—, particularly preferably —NHCO—.

In the present invention, $R^3$ is preferably fluorine.

In the present invention, $R^4$ is preferably methyl, ethyl, or trifluoromethyl, more preferably methyl.

In the present invention, $X^3$ is preferably methylene, or an oxygen atom, more preferably an oxygen atom.

In the present invention, $R^{10}$ is preferably methyl, ethyl, methylcarbonyl, ethylcarbonyl, methylsulfonyl, ethylsulfonyl, or tert-butoxycarbonyl.

In the present invention, the ring is preferably a benzene, thiophene, or pyrazole ring, more preferably a benzene ring.

In the present invention, $R^5$ is preferably —$CONHR^{11}$, fluorine, methoxy, a benzene ring, or a four- to ten-membered heterocyclic ring. The four- to ten-membered heterocyclic ring is preferably an azetidine, pyrrolidine, piperidine, oxazolidine, oxadiazole, triazole, thiophene, furan, pyrazole, thiazole, oxazole, imidazole, pyridine, pyrazine, pyridazine, pyrimidine, pyrazolopyrimidine, pyrrolopyrimidine, pyrazolopyridine, pyrrolopyridine, or dihydropyridooxazine ring.

In the present invention, $R^{11}$ is preferably C1-6 alkyl, C3-6 cycloalkyl, or a pyran, pyrrolidine, piperidine, pyrazole, triazole, oxazole, isooxazole, pyridine, pyridazine, or pyrimidine ring, more preferably C1-6 alkyl.

In the present invention, $R^{13}$ is preferably halogen, C1-6 alkyl, C3-6 cycloalkyl, C1-4 alkoxy, a hydroxyl group, —$NR^{20}R^{21}$, or a benzene, oxetane, pyridine, pyrazole, or oxazole ring, more preferably fluorine, methyl, ethyl, n-propyl, isopropyl, n-butyl, sec-butyl, tert-butyl, isobutyl, cyclopentyl, cyclobutane, oxetane, a hydroxyl group, methoxy, ethoxy, propoxy, isopropoxy, dimethylamino, or a benzene, pyridine, pyrazole, or oxazole ring.

In the present invention, $R^{20}$ is preferably a hydrogen atom, or methyl.

In the present invention, $R^{21}$ is preferably a hydrogen atom, or methyl.

In the present invention, $R^{12}$ is preferably C1-3 alkyl, C3-6 cycloalkyl, benzene, or a four- to six-membered heterocyclic ring. The four- to six-membered heterocyclic ring is preferably an oxetane, azetidine, pyrrolidine, piperidine, pyrazine, pyran, thiopyran, oxazine, oxadiazine, tetrazole, pyrazole, pyridine, pyrazine, pyrimidine, pyridazine, furan, thiophene, oxazole, isooxazole, thiazole, isothiazole, furazan, oxadiazole, or thiadiazole ring. The four- to six-membered heterocyclic ring may be substituted with C1-4 alkoxy.

In the present invention, $R^{14}$ is preferably a hydrogen atom, methyl, ethyl, benzene, or benzyl.

In the present invention, $R^{19}$ is preferably methoxy, —CONHCH$_3$, —CON(CH$_3$)$_2$, or an oxazole, thiazole, pyrazole, or pyridine ring.

In the present invention, $R^{15}$ is preferably methyl, cyclopropyl, or benzene.

In the present invention, $R^{16}$ is preferably a hydroxyl group.

In the present invention, $R^{17}$ is preferably methyl, ethyl, cyclopropyl, or benzene, more preferably methyl.

In the present invention, $R^{18}$ is preferably fluorine, methyl, ethyl, n-propyl, isopropyl, n-butyl, sec-butyl, tert-butyl, isobutyl, cyclopropyl, methoxy, ethoxy, n-propoxy, isopropoxy, oxo, nitrile, a hydroxyl group, hydroxymethyl, 1-methyl-1-hydroxyethyl, methylsulfonyl, pyridine, or dimethylamino.

In the present invention, m is preferably an integer of 1 to 2, more preferably 1.

In the present invention, n is preferably an integer of 0 to 1, more preferably 1.

In the present invention, p is preferably 0.

In the present invention, q is preferably 0.

In the present invention, r is preferably an integer of 0 to 4, more preferably an integer of 0 to 2.

In the present invention, s is preferably an integer of 0 to 2, more preferably 1 or 2.

In the present invention, t is preferably an integer of 0 to 2.

In the present invention, $X^{3a}$ is preferably an oxygen atom.

In the present invention, na is preferably an integer of 0 to 1.

In the present invention, qa is preferably 0,

In the present invention, ra is preferably an integer of 0 to 2.

In the present invention, preferred as the compound of general formula (I) is a combination of the preferred definitions of the ring, $R^1$, $R^2$, $R^3$, $R^4$, $R^5$, $R^6$, $R^7$, $R^8$, $R^{8-1}$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $L^1$, $L^2$, $L^3$, $X^1$, $X^2$, $X^3$, $X^{3a}$, m, n, na, p, q, qa, r, ra, s, and t.

In the present invention, the compound represented by general formula (I) is preferably a compound represented by the following general formula (I-a), a salt, an N-oxide, or a solvate thereof, or a prodrug of these.

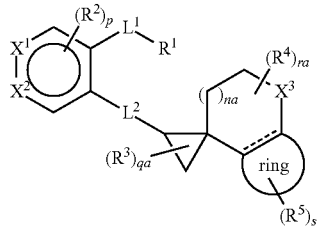

In the general formula (I-a), all symbols are as defined for the symbols in [1] and [2] above.

More preferably, the compound represented by general formula (I) is a compound represented by the following general formula (I-1), a salt, an N-oxide, or a solvate thereof, or a prodrug of these.

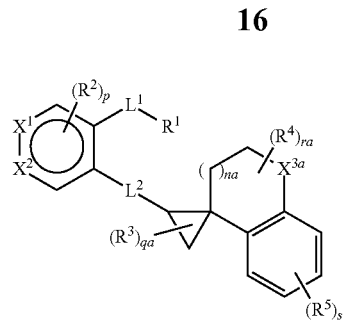

In the general formula (I-1), all symbols are as defined for the symbols in [1] and [2] above.

In the present invention, a more preferred aspect of the compound represented by general formula (I) is a compound represented by the following general formula (I-b), a salt, an N-oxide, or a solvate thereof, or a prodrug of these.

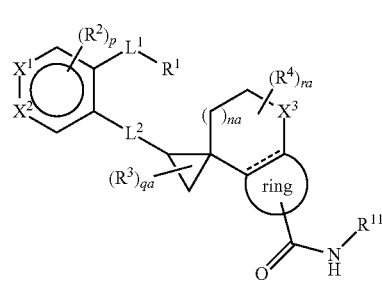

In the general formula (I-b), all symbols are as defined for the symbols in [1] and [2] above.

An even more preferred aspect of the compound represented by general formula (I) is a compound represented by the following general formula (I-c), a salt, an N-oxide, or a solvate thereof, or a prodrug of these.

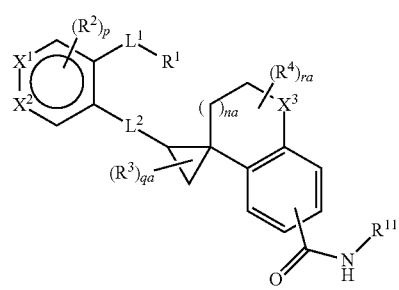

In the general formula (I-c), all symbols are as defined for the symbols in [1] and [2] above.

Preferred is a compound represented by the following general formula (I-d), a salt, an N-oxide, or a solvate thereof, or a prodrug of these.

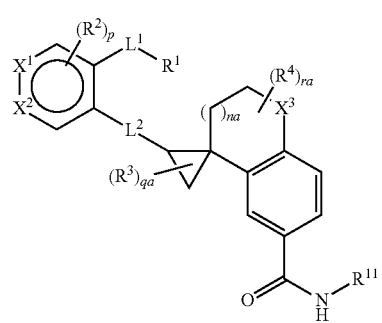

In the general formula (I-d), all symbols are as defined for the symbols in [1] and [2] above.

Further preferred is a compound represented by the following general formula (I-e), a salt, an N-oxide, or a solvate thereof, or a prodrug of these.

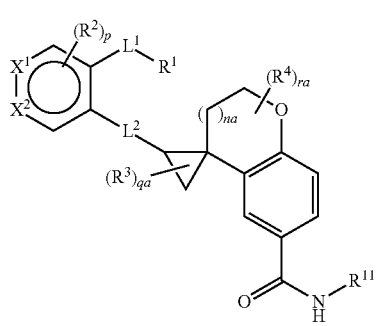
(I-e)

In the general formula (I-e), all symbols are as defined for the symbols in [1] and [2] above.

Particularly preferred is a compound represented by the following general formula (I-2), a salt, an N-oxide, or a solvate thereof, or a prodrug of these.

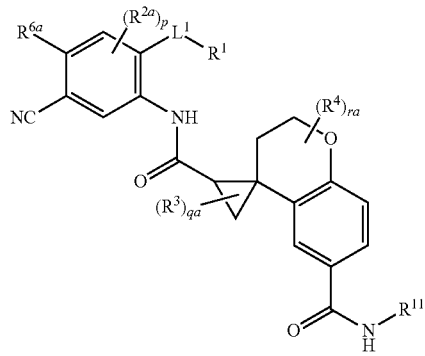
(I-2)

In the general formula (I-2), all symbols are as defined for the symbols in [1], [2], and [5] above.

Most preferred is a compound represented by the following general formula (I-4), a salt, an N-oxide, or a solvate thereof, or a prodrug of these.

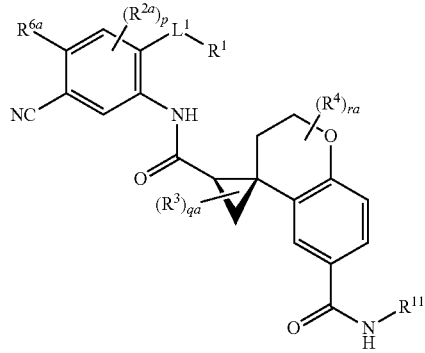
(I-4)

In the general formula (I-4), all symbols are as defined for the symbols in [1], [2], and [5] above.

In the present invention, a further preferred aspect of the compound represented by general formula (I) is a compound represented by the following general formula (I-f), a salt, an N-oxide, or a solvate thereof, or a prodrug of these.

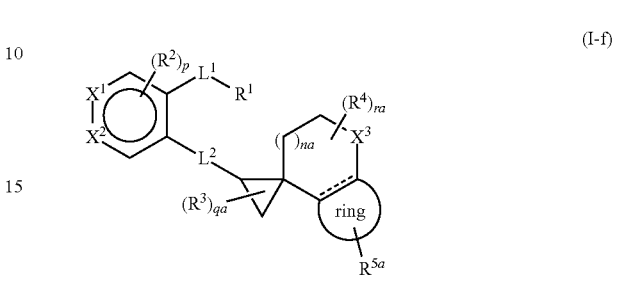
(I-f)

In the general formula (I-f), all symbols are as defined for the symbols in [1], [2], and [9] above.

Further preferred is a compound represented by the following general formula (I-g), a salt, an N-oxide, or a solvate thereof, or a prodrug of these.

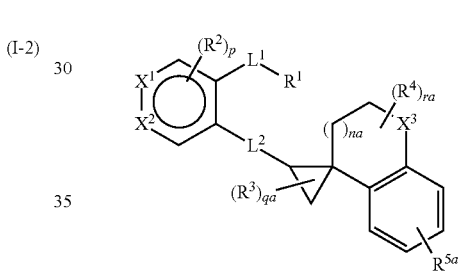
(I-g)

In the general formula (I-g), all symbols are as defined for the symbols in [1], [2], and [9] above.

Preferred is a compound represented by the following general formula (I-h), a salt, an N-oxide, ore solvate thereof, or a prodrug of these.

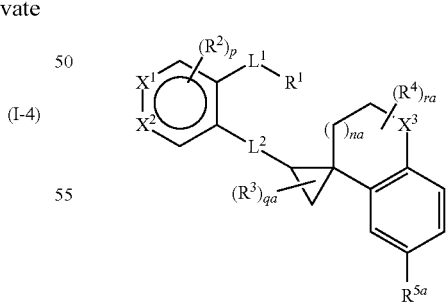
(I-h)

In the general formula (I-h), all symbols are as defined for the symbols in [1], [2], and [9] above.

Further preferred is a compound represented by the following general formula (I-i), a salt, an N-oxide, or a solvate thereof, or a prodrug of these.

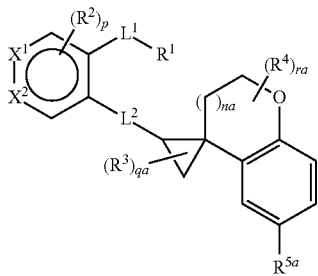

(I-i)

In the general formula (I-i), all symbols are as defined for the symbols in [1], [2], and [9] above.

Particularly preferred is a compound represented by the following general formula (I-3), a salt, an N-oxide, or a solvate thereof, or a prodrug of these.

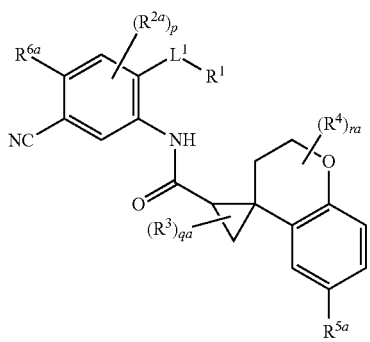

(I-3)

In the general formula (I-3), all symbols are as defined for the symbols in [1], [2], and [9] above.

Most preferred is a compound represented by the following general formula (I-5), a salt, an N-oxide, or a solvate thereof, or a prodrug of these.

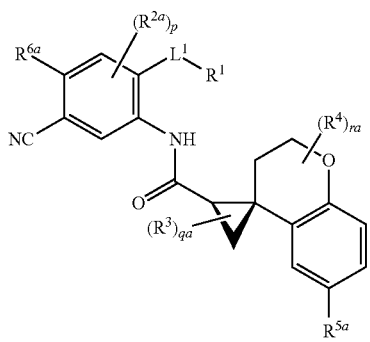

(I-5)

In the general formula (I-5), all symbols are as defined for the symbols in [1], [2], and [9] above.

In the present invention, $L^1$ is independently preferably propylene, and $L^2$ is independently preferably —CH=CH—, —NHCO—, —CONH—, —NHSO$_2$—, or —SO$_2$NH— in a group of general formulae selected from the general formulae (I-a), (I-b), (I-c), (I-d), (I-e), (I-f), (I-g), (I-h), (I-i), and (I-1). More preferably, $L^1$ is propylene, and $L^2$ is —NHCO—, or —CONH—. Further preferably, $L^1$ is propylene, and $L^2$ is —NHCO—.

In the present invention, $L^1$ is independently preferably propylene in a group of general formulae selected from the general formulae (I-2), (I-3), (I-4), and (I-5).

In the present invention, the most preferred aspect of the general formula (I) includes the present compound of Example 1, the present compounds of Examples 2-1 to 2-47, the present compound of Example 3, the present compounds of Examples 4-1 to 4-3, the present compounds of Examples 5 to 6, the present compounds of Examples 7-1 to 7-28, the present compounds of Examples 8 to 9, the present compounds of Examples 10-1 to 10-12, the present compound of Example 11, the present compounds of Examples 12-1 to 12-3, the present compounds of Examples 13 to 17, the present compounds of Examples 18-1 to 18-3, the present compound of Example 19, the present compounds of Examples 20-1 to 20-5, the present compounds of Examples 21 to 22, the present compounds of Examples 23-1 to 23-2, the present compounds of Examples 24 to 27, the present compounds of Examples 28-1 to 28-2, the present compounds of Examples 29 to 30, the present compounds of Examples 31-1 to 31-2, the present compound of Example 32, the present compounds of Examples 33-1 to 33-5, the present compounds of Examples 34 to 36, the present compounds of Examples 37-1 to 37-2, the present compounds of Examples 38-1 to 38-2, the present compound of Example 39, a salt, an N-oxide, or a solvate thereof, or a prodrug of these.

It is to be understood that all isomeric forms of the compounds fall within the scope of the present invention, unless otherwise specifically stated. For example, the alkyl, alkoxy, and alkylene include linear and branched alkyl, alkoxy, and alkylene. The present invention also includes all of the following: isomers due to a double bond, a ring, and a fused ring (E, Z, cis, and trans isomers), isomers due to the presence of an asymmetric carbon (R and S isomers, α and β isomers, enantiomers, diastereomers), optical isomers involving optical rotation (D, L, d, l isomers), polar compounds separated by chromatography (high-polarity, and low-polarity compounds), equilibrium compounds, rotational isomers, mixtures of any proportions of these compounds, and racemic mixtures. The present invention also includes all isomers due to tautomerism.

As is clear for a skilled person, the following symbols as used herein have the following meaning, unless otherwise specifically stated.

represents a bond into the plane of the paper (i.e., the α configuration).

represents a bond out of the plane of the paper (i.e., the β configuration).

represents a mix of α and β configurations.

Salts

The compound represented by general formula (I) is converted into a salt using a known method.

The salt is preferably a pharmaceutically acceptable salt.

Preferably, the salt is water soluble.

Examples of the pharmaceutically acceptable salt include acid addition salts, alkali metal salts, alkali-earth metal salts, ammonium salts, and amine salts.

The acid addition salts may be inorganic acid salts, for example, such as hydrochloride, hydrobromate, hydroiodide, sulfates, phosphates, and nitrates, or organic acid salts, for example, such as acetates, lactates, tartrates, benzoates, citrates, methanesulfonate, ethanesulfonate, trifluoroacetate, benzenesulfonate, toluenesulfonate, isethionates, glucuronates, and gluconates.

Examples of the alkali metal salts include potassium, and sodium.

Examples of the alkali-earth metal salts include calcium, and magnesium.

Examples of the ammonium salts include tetramethylammonium.

Examples of the amine salts include triethylamine, methylamine, dimethylamine, cyclopentylamine, benzylamine, phenethylamine, piperidine, monoethanolamine, diethanolamine, tris(hydroxymethyl)aminomethane, lysine, arginine, and N-methyl-D-glucamine, The present compound may be transformed into an N-oxide using any method. As used herein, N-oxide refers to compounds of general formula (I) with oxidized nitrogen atoms.

The compound represented by general formula (I), and a salt thereof may be transformed into a solvate.

Preferably, the solvate is non-toxic, and water soluble. Examples of suitable solvates include solvates using water, and solvates using alcoholic solvents (for example, ethanol).

Prodrug

As used herein, a prodrug of the compound represented by general formula (I) refers to a compound that is transformed into the compound of general formula (I) in the body through reaction with, for example, an enzyme, and stomach acid. The following are examples of prodrugs of the compounds represented by general formula (I): A compound of general formula (I) with an amino group that is acylated, alkylated, or phosphorylated (for example, a compound of general formula (I) with an amino group that is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, or test-butylated); a compound of general formula (I) with a hydroxyl group that is acylated, alkylated, phosphorylated, or borated (for example, a compound of general formula (I) with a hydroxyl group that is acetylated, palmitoylated, propanoylated, pivaloylated, succinylated, fumarylated, alanylated, or dimethylaminomethylcarbonylated; and a compound of general formula (I) with a carboxy group that is esterificated or amidated (for example, a compound of general formula (I) with a carboxy group that is ethylesterificated, phenylesterificated, carboxymethylesterificated, dimethylaminomethylesterificated, pivaloyloxymethylesterificated, 1-{(ethoxycarbonyl)oxy}ethylesterificated, phthalidylesterificated, (5-methyl-2-oxo-1,3-dioxolen-4-yl)methylesterificated, 1-{[(cyclohexyloxy)carbonyl]oxy}ethylesterificated, methylamidated). These compounds may be produced by a method known per se. The prodrug of the compounds represented by general formula (I) may be a hydrate or a nonhydrate. The prodrug of the compounds represented by general formula (I) may be one that transforms into the compound of general formula (I) under physiological conditions, such as described in Development of Drugs, Vol. 7, Molecular Design, pp. 163-198, 1990, Hirokawa Publishing Company.

The atoms constituting the compounds represented by general formula (I) may be replaced with their isotopes (for example, $^2H$, $^3H$, $^{13}C$, $^{14}C$, $^{15}N$, $^{16}N$, $^{17}O$, $^{18}O$, $^{18}F$, $^{35}S$, $^{36}Cl$, $^{77}Br$, and $^{125}I$).

Method of Production of Present Compounds

The present compounds represented by general formula (I) may be produced by known methods, for example, by the methods described below, methods equivalent thereto, or the methods described in the Examples below. In the methods of production below, the feed compound may be in the form of a salt. The salt may be any of the pharmaceutically acceptable salts exemplified for the present compounds of general formula (I).

The present compound of general formula (I) of which $L^2$ is —NHCO— (general formula (IVa)), and the present compound of general formula (I) of which $L^2$ is —CONH— (general formula (IVb)) can be produced by the methods represented by the following reaction schemes (Ia) and (Ib), respectively.

Reaction scheme (Ia)

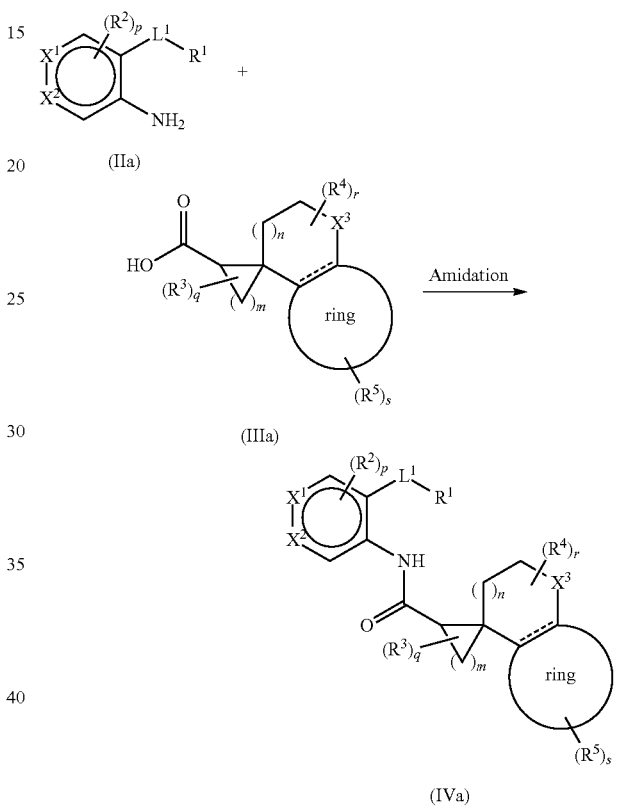

In the formula, all symbols are as defined in [1] above.

Reaction scheme (Ib)

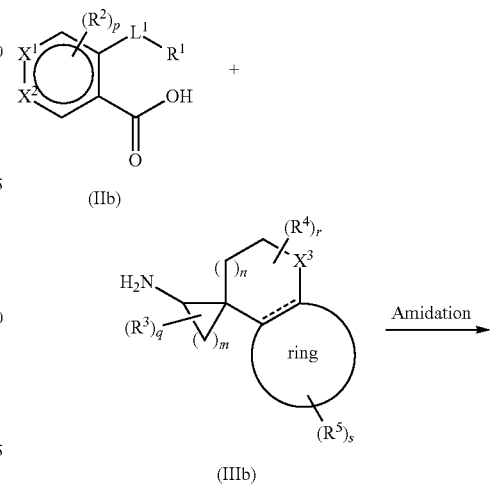

-continued

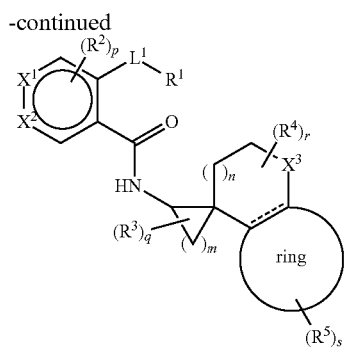

(IVb)

In the formula, all symbols are as defined in [1] above.

Specifically, the present compound represented by general formula (IVa) can be produced by amidation reaction of the compound of general formula (IIa), and the compound of general formula (IIIa). The present compound of general formula (IIIb) can be produced by amidation reaction of the compound of general formula (IIb), and the compound of general formula (IIIb).

The amidation reaction is known, and may be, for example,
(1) a method using an acid halide,
(2) a method using a mixed acid anhydride, or
(3) a method using a condensing agent.

The following describes these methods in detail.

(1) In the method using an acid halide, for example, carboxylic acid is reacted with an acid halide reagent (e.g., oxalyl chloride, or thionyl chloride) at about −20° C. to reflux temperature in an organic solvent (e.g., chloroform, dichloromethane, diethyl ether, or tetrahydrofuran), or without solvent. The resulting acid halide is then reacted with an amine in an organic solvent (e.g., chloroform, dichloromethane, diethyl ether, or tetrahydrofuran) at about 0 to 40'C in the presence of r base (e.g., pyridine, triethylamine, dimethylaniline, dimethylaminopyridine, or diisopropylethylamine). Alternatively, the acid halide may be reacted with an amine at about 0 to 40° C. in an organic solvent (e.g., dioxane, or tetrahydrofuran), using an alkaline aqueous solution (e.g., sodium bicarbonate water, or a sodium hydroxide solution).

(2) In the method using a mixed acid anhydride, for example, carboxylic acid is reacted with an acid halide (e.g., pivaloyl chloride, tosyl chloride, or methyl chloride), or with an acid derivative (e.g., ethyl chloroformate, or isobutyl chloroformate) at about 0 to 40° C. in an organic solvent (e.g., chloroform, dichloromethane, diethyl ether, or tetrahydrofuran) or without solvent, in the presence of a base (e.g., pyridine, triethylamine, dimethylaniline, dimethylaminopyridine, or diisopropylethylamine). The resulting mixed acid anhydride is then reacted with an amine at about 0 to 40° C. in an organic solvent (e.g., chloroform, dichloromethane, diethyl ether, or tetrahydrofuran).

(3) in the method using a condensing agent, for example, carboxylic acid is reacted with an amine at about 0° C. to reflux temperature in an organic solvent (e.g., chloroform, dichloromethane, dimethylformamide, dimethylacetoamide, diethyl ether, or tetrahydrofuran) or without solvent in the presence or absence of a base (e.g., pyridine, triethylamine, dimethylaniline, or dimethylaminopyridine), using a condensing agent (e.g., 1,3-dicyclohexylcarbodiimide (DCC) 1-ethyl-[3-(dimethylamino)propyl]carbodiimide (EDO), 1,1'-carbonyldiimidazole (CDI), 2-chloro-1-methylpyridiniumiodine, or 1-propanephosphonic acid cyclic anhydride (T3P)), with or without 1-hydroxybenzotriazole (HOBt).

Desirably, the reactions (1), (2), and (3) are performed under anhydrous conditions in an inert gas (e.g., argon, or nitrogen) atmosphere.

The present compound of general formula (I) of which $L^2$ is —NHSO$_2$— (general formula (IVc)), and the present compound of general formula (I) of which $L^2$ is —SO$_2$NH— (general formula (IVd)) can be produced by the methods represented by the following reaction schemes (Ic) and (Id), respectively.

Reaction scheme (Ic)

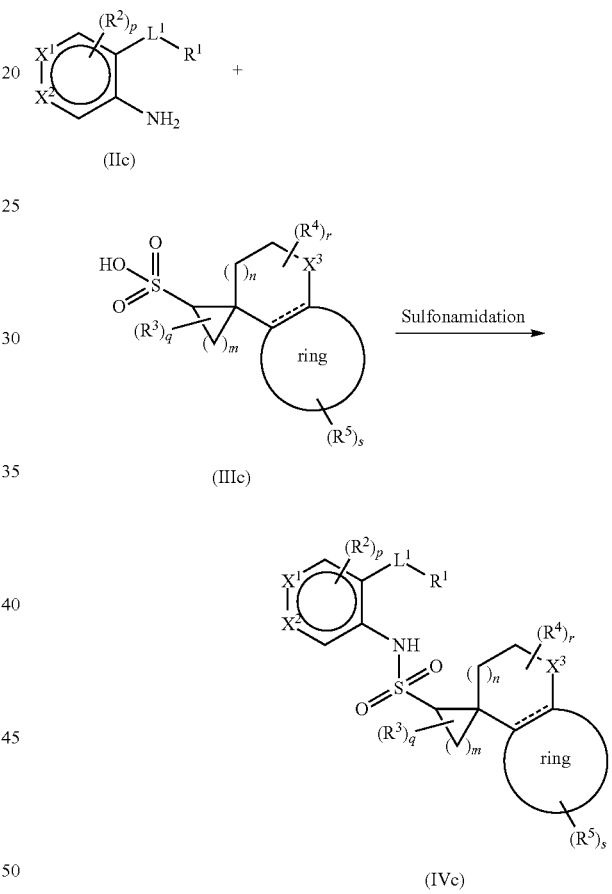

In the formula, all symbols are as defined in [1] above.

Reaction scheme (Id)

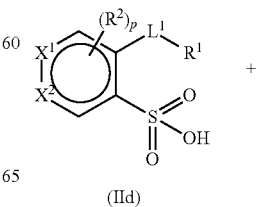

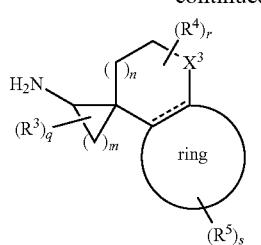

(IIId)

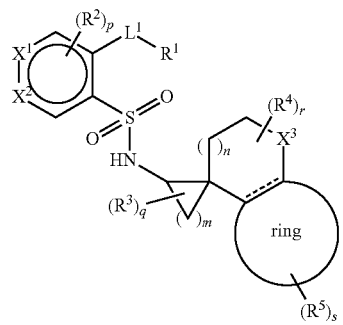

(IVd)

In the formula, all symbols are as defined in [1] above.

Specifically, the present compound represented by general formula (IVc), can be produced by Sulfonamidation reaction of the compound of general formula (IIc), and the compound of general formula (IIIc). The present compound of general formula (IVd) can be produced by Sulfonamidation reaction of the compound of general formula (IId), and the compound of general formula (IIId).

The Sulfonamidation reaction is known. For example, sulfonic acid is reacted with an acid halide (e.g., oxalyl chloride, thionyl chloride, phosphorous pentachloride, or phosphorous trichloride) at −20° C. to reflux temperature in an organic (e.g., chloroform, dichloromethane, dichloroethane, diethyl ether, tetrahydrofuran, or methyl t-butyl ether) or without solvent. The resulting sulfonyl halide is then reacted with an amine at about 0 to 40° C. in an organic solvent (e.g., chloroform, dichloromethane, dichloroethane, diethyl ether, or tetrahydrofuran) in the presence of a base (e.g., diisopropylethylamine, pyridine, triethylamine, dimethylaniline, or dimethylaminopyridine).

The present compound of general formula (I) of which $L^2$ is —NHCH$_2$— (general formula (IVe)), and the present compound of general formula (I) of which $L^2$ is —CH$_2$NH— (general formula (IVf)) can be produced by the methods represented by the following reaction schemes (Ie) and (If), respectively.

Reaction scheme (Ie)

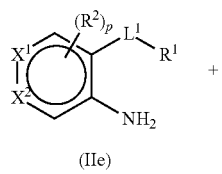

(IIe)

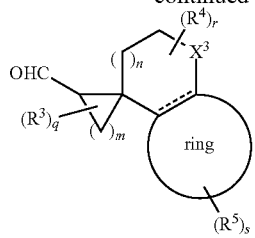

(IIIe)

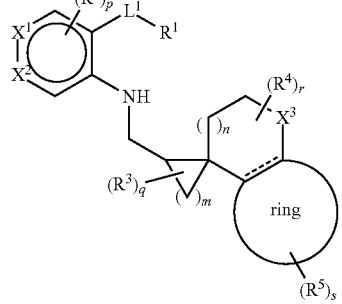

(IVe)

In the formula, all symbols are as defined in [1] above.

Reaction scheme (If)

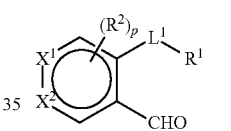

(IIf)

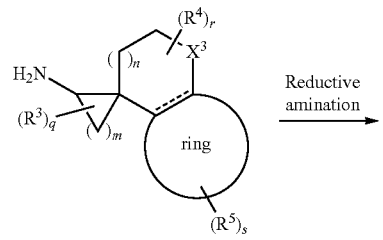

(IIIf)

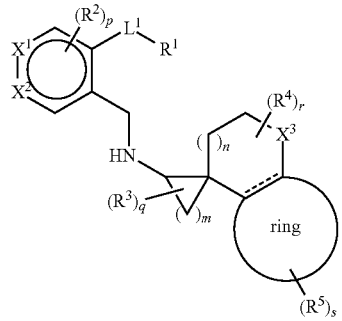

(IVf)

In the formula, all symbols are as defined in [1] above.

Specifically, the present compound represented by general formula (IVe) can be produced by reductive amination reaction of the compound of general formula (IIe), and the compound of general formula (IIIe). The present compound of general formula (IVf) can be produced by reductive amination reaction of the compound of general formula (IIf), and the compound of general formula (IIIf).

The reductive amination reaction is known. For example, the reaction is performed in an organic solvent (e.g., dichloroethane, dichloromethane, dimethylformamide, acetic acid, or a mixture of these) at about 0 to 40° C. in the presence of a reducing agent (e.g., sodium triacetoxyborohydride, sodium cyanoborohydride, or sodium borohydride).

The present compound of general formula (I) of which $L^2$ is —OCH$_2$— (general formula (IVg)), and the present compound of general formula (I) of which $L^2$ is —CH$_2$O— (general formula (IVh)) can be produced by the methods represented by the following reaction schemes (Ig) and (Ih), respectively.

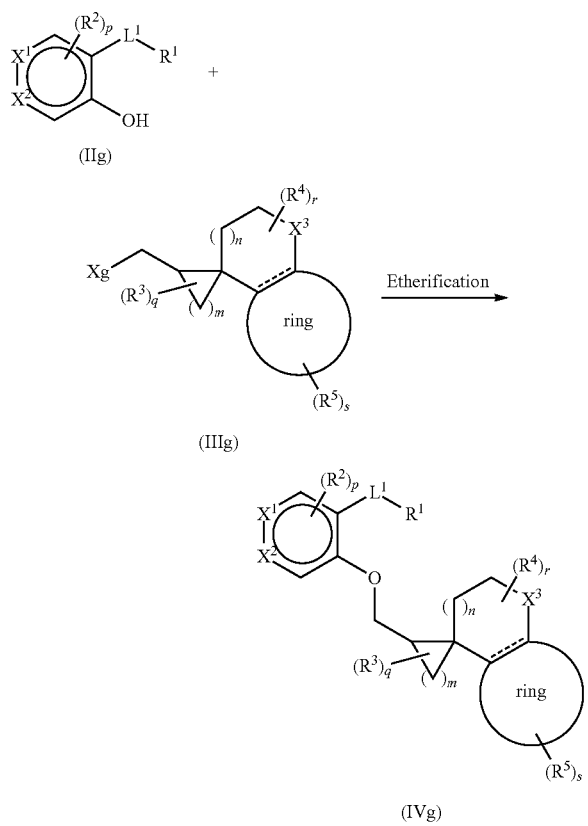

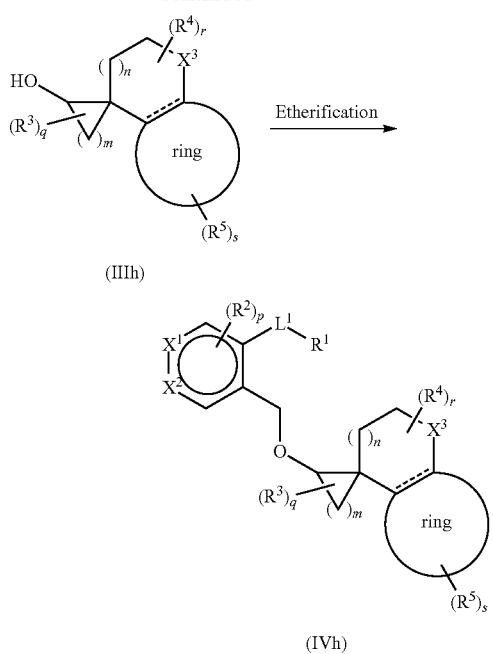

In the formula, Xg represents halogen, tosylate, or mesylate, and the other symbols are as defined in [1] above.

In the formula, Xh represents halogen, tosylate, or mesylate, and the other symbols are as defined in. [1] above.

Specifically, the present compound represented by general formula (IVg) can be produced by etherification reaction of the compound of general formula (IIg), and the compound of general formula (IIIg). The present compound of general formula (IVh) can be produced by etherification reaction of the compound of general formula (IIh), and the compound of general formula (IIIh).

The etherification reaction is known. For example, the reaction is performed in an organic solvent (e.g., dimethylformamide, dimethylsulfoxide, chloroform, dichloromethane, diethyl ether, tetrahydrofuran, or methyl t-butyl ether) at about 0 to 100° C. in the presence of an alkali metal hydroxide (e.g., sodium hydroxide, potassium hydroxide, or lithium hydroxide), an alkali earth metal hydroxide (e.g., barium hydroxide, or calcium hydroxide), a carbonate (e.g., sodium carbonate, or potassium carbonate), or an aqueous solution or a mixture of these.

The present compound of general formula (I) of which $L^2$ is —SCH$_2$— (general formula (IVj)), and the present compound of general formula (I) of which $L^2$ is —CH$_2$S— (general formula (IVk)) can be produced by the methods represented by the following reaction schemes (Ij) and (Ik), respectively.

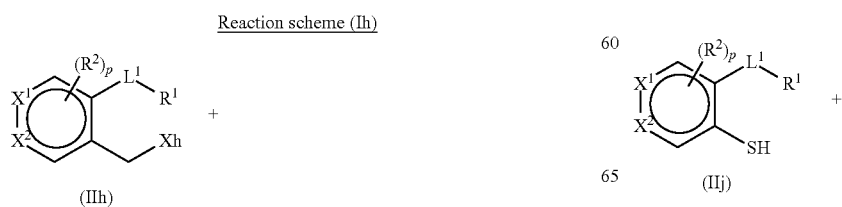

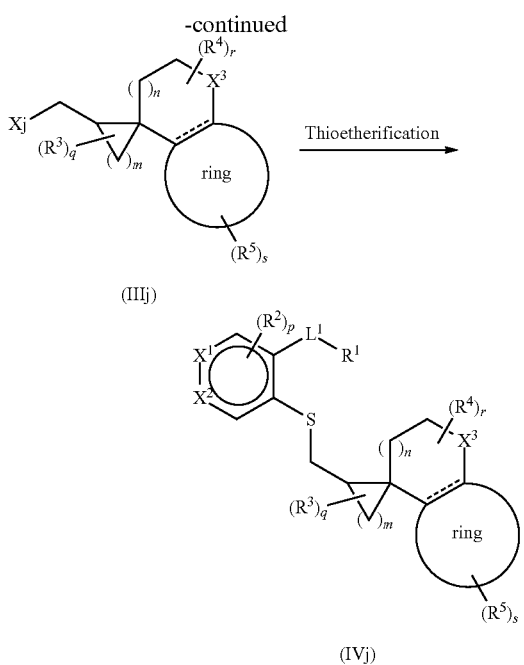

In the formula, Xj represents halogen, tosylate, or mesylate, and the other symbols are as defined in [1] above.

Reaction scheme (Ik)

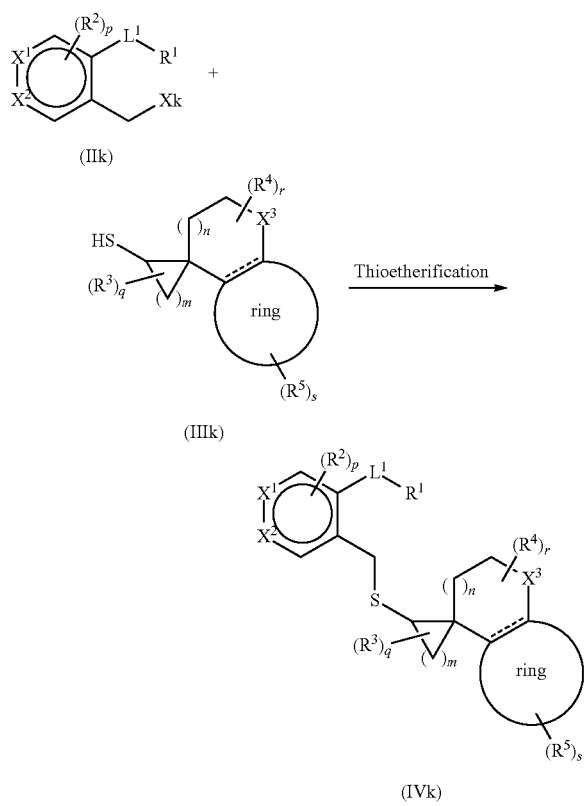

In the formula, Xk represents halogen, tosylate, or mesylate, and the other symbols are as defined in [1] above.

Specifically, the present compound represented general formula (IVj) can be produced by thioetherification reaction of the compound of general formula (IIj), and the compound of general formula (IIIj). The present compound of general formula (IVk) can be produced by thioetherification reaction of the compound of general formula (IIk), and the compound of general formula (IIIk).

The thioetherification reaction is known. For example, the reaction is performed in an organic solvent (e.g., dimethylformamide, dimethylsulfoxide, chloroform, dichloromethane, diethyl ether, tetrahydrofuran, or methyl t-butyl ether) at about 0 to 100° C. in the presence of an alkali metal hydroxide (e.g., sodium hydroxide, potassium hydroxide, or lithium hydroxide), an alkali earth metal hydroxide (e.g., barium hydroxide, or calcium hydroxide), a carbonate (e.g., sodium carbonate, or potassium carbonate), or an aqueous solution or a mixture of these.

The present compound of general formula (I) of which. $L^2$ is —S(O)CH$_2$— or —SO$_2$CH$_2$— can be produced by appropriately subjecting the sulfur atom of the present compound of the general formula (IVj) above to oxidation reaction.

The present compound of general formula (I) of which $L^2$ is —CH$_2$S(O)— or —CH$_2$SO$_2$— can be produced by appropriately subjecting the sulfur atom of the present compound of the general formula (IVk) above to oxidation reaction.

The oxidation reaction (sulfoxidation reaction: —SCH$_2$— → —S(O)CH$_2$—, or —CH$_2$— → —CH$_2$S(O)—) is known. For example, the reaction is performed in an organic solvent (e.g., dichloromethane, chloroform, benzene, hexane, methanol, t-butyl alcohol, acetone, acetonitrile, tetrahydrofuran, acetic acid, or N,N-dimethylformamide), or in water or in a mixed solvent of these at about −40 to 0° C. in the presence of 1 to 1.2 equivalents of an oxidizing agent (e.g., hydrogen peroxide, sodium periodate, acyl nitrite, sodium perborate, sodium hypochlorite, a peracid (e.g., 3-chloroperbenzoic acid, or peracetic acid), an Oxone® (potassium, peroxymonosulfate; hereinafter, simply referred to as Oxone), potassium permanganate, chromic acid, or dimethyldioxolan).

The oxidation reaction (sulfonation reaction: —SCH$_2$— → —SO$_2$CH$_2$—, or —CH$_2$S— → —CH$_2$SO$_2$—) is known. For example, the reaction is performed in a suitable organic solvent (e.g., dichloromethane, chloroform, benzene, hexane, methanol, t-butyl alcohol, acetone, acetonitrile, tetrahydrofuran, acetic acid, or N,N-dimethylformamide), or in water or in a mixed solvent of these at about 20 to 60° C. in the presence of an excess oxidizing agent (e.g., hydrogen peroxide, sodium, periodate, acyl nitrite, sodium, perborate, sodium hypochlorite, a peracid (e.g., 3-chloroperbenzoic acid, or peracetic acid), Oxone® (potassium peroxymonosulfate), potassium permanganate, chromic acid, or dimethyldioxolan).

The present compound of general formula (I) of which $L^2$ is —CH═CH— (general formula (IVm)) can be produced by the method represented by the following reaction scheme (Im).

Reaction scheme (Im)

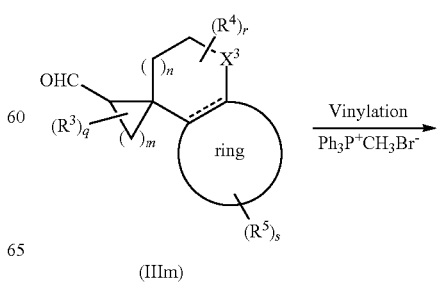

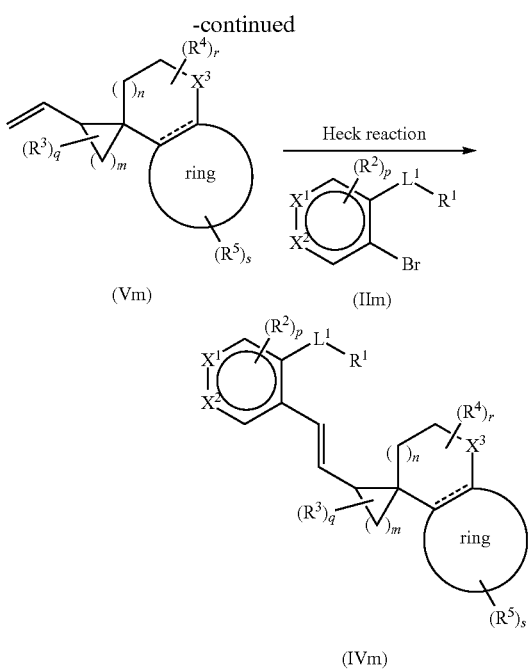

(Vm)

(IIm)

(IVm)

In the formula, all symbols are as defined in [1] above.

Specifically, the present compound represented by general formula (IVm) can be produced by the Heck reaction of the compound of general formula (IIm) with the compound of general formula (Vm) produced by vinylation reaction of the compound represented by general formula (IIIm).

The vinylation reaction is known. For example, the reaction is performed using the compound of general formula (IIIm), and methyltriphenylphosphonium bromide in an organic solvent (e.g., acetonitrile, methylene chloride, tetrahydrofuran, toluene, benzene, or an appropriate mixed solvent of these organic solvents) at about 0° C. to 120° C. in the presence of a base (for example, potassium carbonate, sodium hydride, potassium hydride, n-butyllithium, potassium tert-butoxide, or 1,8-diazabicyclo[5.4.0]undec-7-ene triethylamine (DBU)).

The Heck reaction is known. For example, the reaction is performed in an organic solvent (for example, toluene, diethyl ether, benzene, dichlorobenzene, dimethylformamide, or an appropriate mixed solvent of these organic solvents) at about 0° C. to 120° C. in the presence of a base (for example, tripotassium phosphate, sodium bicarbonate, or triethylamine) and a catalyst (for example, a palladium catalyst, for example, such as palladium chloride, palladium acetate, and tetrakis(triphenylphosphine)palladium (O); a nickel catalyst, for example, such as tetrakis(triphenylphosphine) nickel, and bis(triphenylphosphine) nickel (II); a cobalt catalyst, for example, such as cobalt chloride; a copper catalyst, for example, such as copper chloride; a zinc catalyst, for example, such as zinc; or an appropriate mixed catalyst of these catalysts), with or without a phosphorus reagent (for example, 1,3-bis(diphenylphosphino) propane (dppp), or $Ph_2P-(CH_2)_6-PPh_2$).

The present compound of general formula (I) of which $L^2$ is $-CH_2CH_2-$ can be produced by appropriately subjecting the $-CH=CH-$ of the present compound of the general formula (IVm) above to reduction reaction.

The reduction reaction is known. For example, the reaction is performed in an organic solvent (for example, tetrahydrofuran, dioxane, dimethoxyethane, diethyl ether, methanol, ethanol, benzene, toluene, acetone, methyl ethyl ketone, acetonitrile, dimethylformamide, water, ethyl acetate, acetic acid, or an appropriate mixed solvent of these organic solvents) in a hydrogen atmosphere under ordinary pressure or increased pressure, in the presence of ammonium formate or in the presence of hydrazine at about 0 to 200° C., in the presence of a hydrogenation catalyst (e.g., palladium-carbon, palladium black, palladium, palladium hydroxide, platinum dioxide, platinum-carbon, nickel, Raney nickel, or ruthenium chloride), with or without an acid (e.g., hydrochloric acid, sulfuric acid, hypochlorous acid, boric acid, tetrafluoroboric acid, acetic acid, p-toluenesulfonic acid, oxalic acid, trifluoroacetic acid, or formic acid).

The compound of general formula (IIIa) in reaction scheme (Ia) of which q is 0, and m is 1 (general formula (IIIaa)) can be produced by the method represented by the following reaction scheme (Iaa).

Reaction scheme (Iaa)

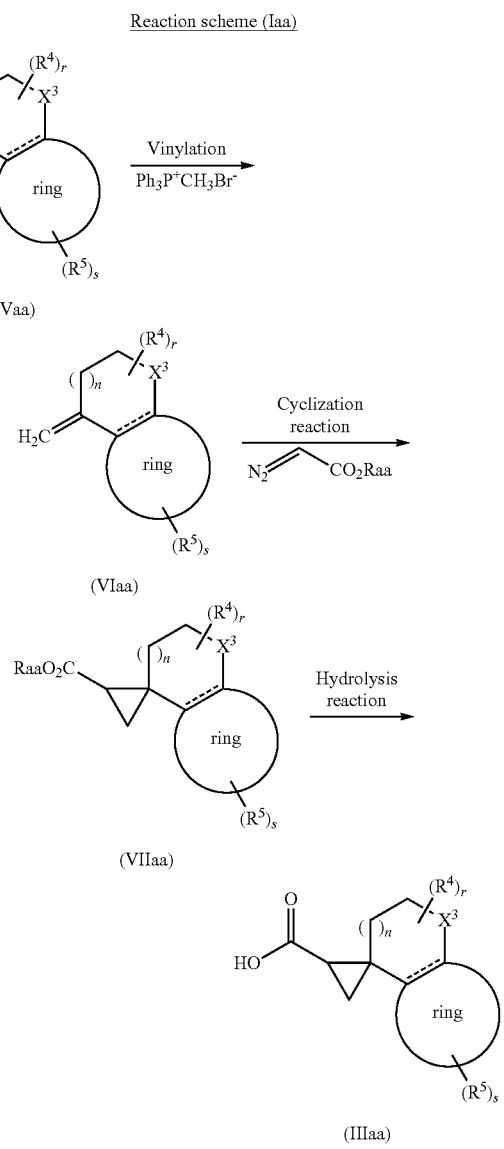

In the formula, Raa is C1-4 alkyl, an the other symbols are as defined in [1] and [2] above.

Specifically, the compound represented by general formula (IIIaa) can be produced by subjecting the compound of general formula (VIaa) produced by vinylation reaction of the compound of general formula (Vaa) to cyclization reaction, and to hydrolysis reaction.

The vinylation reaction is known. For example, the reaction is performed using the compound of general formula (Vaa), and methyltriphenylphosphonium bromide in an organic solvent (for example, acetonitrile, methylene chloride, tetrahydrofuran, toluene, benzene, or an appropriate mixed solvent of these organic solvents) at about 0° C. to 120° C. in the presence of a base (for example, potassium carbonate, sodium hydride, potassium hydride, n-butyllithium, potassium tert-butoxide, 1,8-diazabicyclo[5.4.0]undec-7-ene triethylamine (DBU)).

The cyclization reaction is known. For example, the reaction is performed using the compound of general formula (VIaa), and a diazo compound in an organic solvent (for example, toluene, benzene, methylene chloride, dichloroethane, methanol, ethanol, hexane, tetrahydrofuran, water, or an appropriate mixed solvent of these organic solvents) at about −78° C. to 120° C. in the presence of a catalyst (e.g., a ruthenium catalyst, for example, such as a dichloro(cymene)ruthenium dimer ([Ru (p-cymene)$Cl_2]_2$) $RuCl_2$ $(PPh_3)_3$, and $RuCl(Cp)(PPh_3)_2$; a rhodium catalyst, for example, such as $Rh_2$(O—CO-heptyl)$_4$, $Rh_2$(O—CO-t$Bu)_4$, $Rh_2(OAC)_4$, $Rh_2$(O-Piv)$_4$, $Rh_2$((S)-PTTL)$_4$, $Rh_2$((S)-DOSP)$_4$, $Rh_2(esp)_2$ and $Rh_2$ ((S)-NTTL)$_4$; a silver catalyst, for example, such as silver (I) tetrafluoroborate; a copper catalyst, for example, such as CuOTf, $Cu(OAc)_2$, and [Cu $(MeCN)_4]PF_6$; a tin catalyst, for example, such as Sn(tpp) $(OTf)_2$; an iron catalyst, for example, such as [Fe(Cp)(CO)$_2$ $(thf)]BF_4$; a cobalt catalyst, 2,6-bis(4-isopropyl-4,5-dihydrooxazol-2-yl)pyridine, 2,6-bis((S)-4-isopropyl-4,5-dihydrooxazol-2-yl)pyridine, or 2,6-bis((R)-4-isopropyl-4,5-dihydrooxazol-2-yl)pyridine). In the cyclization reaction, an optically active tricyclic Spiro compound (an optical isomer of the compound represented by general formula (VIIaa)) can be produced by using a known optically active asymmetric catalyst.

The hydrolysis reaction (deprotection reaction of the carboxyl group) is known. Alkali hydrolysis is an example of the hydrolysis reaction. For example, the deprotection reaction by alkali hydrolysis is performed in an organic solvent (e.g., methanol, tetrahydrofuran, or dioxane) at a temperature of 0 to 100° C. using an alkali metal hydroxide (e.g., sodium hydroxide, potassium hydroxide, or lithium hydroxide), an alkali earth metal hydroxide (e.g., barium hydroxide, or calcium hydroxide), a carbonate (e.g., sodium carbonate, or potassium carbonate), or an aqueous solution or a mixture of these.

The compound of general formula (IIIb) in reaction scheme (Ib), the compound of general formula (IIId) in reaction scheme (Id), or the compound of general formula (IIIf) in reaction scheme (If) of which m is 1 can be produced from the compound of general formula (IIIaa) in reaction scheme (Iaa) using a known method, for example, such as described in Comprehensive Organic Transformations: A Guide to Functional Group Preparations, 2nd Edition (Richard C. Larock, John Wiley & Sons Inc., 1999).

The compound of general formula (IIIc) in reaction scheme (Ic) of which m of an integer of 1 can be produced from the compound of general formula (IIIaa) in reaction scheme (Iaa) using a known method, for example, such as described in Comprehensive Organic Transformations: A Guide to Functional Group Preparations, 2nd Edition (Richard C. Larock, John Wiley Sons Inc., 1999).

The compound of general formula (IIIe) in reaction scheme (Ie), or the compound of general formula (IIIm) in reaction scheme (Im) of which m is 1 can be produced from the compound of general formula (IIIaa; in reaction scheme (Iaa) using a known method, for example, such as described in Comprehensive Organic Transformations: A Guide to Functional Group Preparations, 2nd Edition (Richard C. Larock, John Wiley & Sons Inc., 1999).

The compound of general formula (IIIg) in reaction scheme (Ig), or the compound of general formula (IIIj) in reaction scheme (Ij) of which m is 1 can be produced from, the compound of general formula (IIIaa) in reaction scheme (Iaa) by reducing the carboxylic acid to produce a primary alcohol derivative, and transforming the alcohol derivative into a halogen derivative, a tosylate derivative, or a mesylate derivative, using a known method, for example, such as described in Comprehensive Organic Transformations: A Guide to Functional Group Preparations, 2nd Edition (Richard C. Larock, John Wiley & Sons Inc., 1999).

The compound of general formula (IIIh) in reaction scheme (Ih) of which m is 1 can be produced from the compound of general formula (IIIaa) in reaction scheme (Iaa) using a known method, for example, such as described in Comprehensive Organic Transformations: A Guide to Functional Group Preparations, 2nd Edition (Richard C. Larock, John Wiley & Sons Inc., 1999), or in Tetrahedron Letter, Vol. 28, pp. 4489-4492, 1987.

The compound of general formula (IIIk) in reaction scheme (Ik) of which m is 1 can be produced by producing a secondary alcohol derivative from the compound of general formula (IIIaa) in reaction scheme (Iaa), and transforming the alcohol derivative into a thiol derivative, using a known method, for example, such as described in Comprehensive Organic Transformations: A Guide to Functional Croup Preparations, 2nd. Edition (Richard C. Larock, John Wiley & Sons Inc., 1999), or in Tetrahedron Letter, Vol. 28, pp. 4489-4492, 1987.

In the compounds of general formulae (IIIa), (IIIb), (IIIc), (IIId), (IIIe), (IIIf), (IIIg), (IIIh), (IIIj), (IIIk), and (IIIm) used as starting materials in the reaction schemes, the compounds with an m of 1, and a q of 1 to 3, or the compounds with an m of 2 to 4, and a q of 1 to 3 are known, or can be produced with ease using a known method, for example, such as described in Comprehensive Organic Transformations: A. Guide to Functional Group Preparations, 2nd Edition (Richard C. Larock, John Wiley & Sons Inc., 1999).

The compounds of general formulae (IIa), (IIb), (IIc), (IId), (IIe), (IIf), (IIg), (IIh), (IIj), (IIk), (IIm), and (Vaa) used as starting materials in the reaction schemes are known, or can be produced with ease using a known method, for example, such as described in Comprehensive Organic Transformations: A Guide to Functional Group Preparations, 2nd Edition (Richard. C. Larock, John Wiley & Sons Inc., 1999).

The present compound having an amino group, a carboxyl group, or a hydroxyl group can be produced using a compound that has been protected, as required, by a protecting group commonly used for such groups, for example, such as described in Comprehensive Organic Transformations: A Guide to Functional Group Preparations, 2nd Edition (Richard C. Larock, John Wiley & Sons Inc., 1999) The present compound can be obtained by performing a known deprotection reaction, for example, the deprotection reaction described in Comprehensive Organic Transformations: A Guide to Functional Group Preparations, 2nd Edition (Richard C. Larock, John Wiley & Sons Inc., 1999) after the completion of the amidation reaction of reaction scheme (Ia) or (Ib), the Sulfonamidation reaction of reaction scheme (Ic) or (Id), the reductive amination reaction of reaction scheme (Ie) or (If), the etherification reaction of reaction scheme (Ig) or (Ih), the thioetherification reaction of reaction scheme (Ij) or (Ik), or the Heck reaction of reaction scheme (Im) or after a suitable reaction process.

The present compounds of general formula (I) other than the compounds described above may be produced by combining the methods described in the Examples described in this specification, or by combining known methods, for example, such as described in Comprehensive Organic Transformations: A Guide to Functional Group Preparations, 2nd Edition (Richard C. Larock, John Wiley & Sons Inc., 1999).

When the present compound is an optically active compound, the compound also can be produced using a starting material or a reagent having optical activity, or by optically separating a racemic intermediate and deriving the present compound therefrom, or optically separating a racemic form of the present compound.

The optical separation method is known. For example, a salt or a complex is formed with other optically active compound, and the compound of interest is isolated after recrystallization, or the compound is directly separated using, for example, a chiral column.

In the reactions used herein, reactions involving heat may be performed using a water bath, an oil bath, a sand bath, or a microwave, as is evident to a skilled person.

In the reactions used herein, a reagent may be used that is supported on a solid-phase polymer (for example, polystyrene, polyacrylamide, polypropylene, or polyethylene glycol), as appropriate.

In the reactions used herein, the reaction product may be purified by using ordinary purification means, for example, such as distillation under ordinary pressure or reduced pressure, high-performance liquid chromatography using silica gel or magnesium silicate, thin-layer chromatography, methods using an ion-exchange resin or a scavenger resin, column chromatography, washing, and recrystallization. The purification may be performed after each reaction, or after several reactions.

Toxicity

The present compound has low toxicity, and is safe to use as a drug.

Drug Applications

The present invention is intended to create compounds having a strong antagonistic activity against the $EP_4$ receptor, and that show desirable pharmacokinetics, and to find a compound that is useful as a preventive and/or a therapeutic drug against diseases caused by $EP_4$ receptor activation.

The present compound shows antagonistic activity against the $EP_4$ receptor, and is useful as a preventive and/or a therapeutic agent against diseases caused by $EP_4$ receptor activation, for example, such as a bone disease, a cancer, a systemic granulomatous disease, an immune disease, an allergic disease, asthma, alveolar pyorrhea, gingivitis, periodontitis, Alzheimer's, Kawasaki disease, burn, multiple organ failure, chronic headache, pain, vasculitis, venous incompetence, varicose veins, aneurysm, aortic aneurysm, anal fistula, diabetes insipidus, stress, endometriosis, uterine adenomyosis, patent ductus arteriosus in neonates, and cholelithiasis.

Specific examples of the bone disease include osteoporosis, rheumatoid arthritis, osteoarthritis, and skeletal dysplasias. Examples of the cancer include breast cancer, ovarian cancer, colorectal cancer (for example, colon cancer), lung cancer (for example, non-small cell cancer), prostate cancer, head and neck cancer (for example, oral squamous cell carcinoma, head and neck squamous cell carcinoma, pharyngeal cancer, laryngeal cancer, tongue cancer, thyroid cancer, acoustic neuroma), lymphoma (for example, B cell lymphoma, T cell lymphoma), uveal melanoma, thymoma, mesothelioma, esophageal cancer, stomach cancer, duodenal cancer, hepatocellular carcinoma, cholangiocarcinoma, gallbladder cancer, pancreatic cancer, renal cell carcinoma, renal pelvis and ureter cancer, bladder cancer, penile cancer, testicular cancer, uterus cancer, vaginal cancer, vulvar cancer, skin cancer (for example, malignant melanoma), malignant bone tumor, soft tissue sarcoma, chondrosarcoma, leukemia (for example, acute myelogenous leukemia, acute lymphoblastic leukemia, chronic myelogenous leukemia, chronic lymphocytic leukemia), myelodysplastic syndrome, and multiple myeloma. Examples of the immune disease include amyotrophic lateral sclerosis (ALS), multiple sclerosis, Sjogren's syndrome, systemic lupus erythematosus, and AIDS. Examples of the allergic disease include allergic conjunctivitis, allergic rhinitis, contact dermatitis, and psoriasis. Examples of the chronic headache include migraine, tension headache, a combination of these, and cluster headache.

The present compound may be administered as a concomitant drug with other medicinal agent to:

1) complement and/or enhance the preventive and/or therapeutic effect of the compound, 2) improve the kinetics and absorption of the compound, and reduce the dose of the compound, and/or 3) reduce the side effects of the compound.

The concomitant drug using the present compound with other medicinal agent may be administered in the form of a compounding agent containing the both components in the same preparation, or in the form of separate preparations. When administered as separate preparations, the preparations may be administered at the same or different times. When administered at different times, the present compound may be administered before other medicinal agent, or other medicinal agent may be administered before the present compound. These may be administered using the same or different method.

The disease for which the concomitant drug shows a preventive and/or therapeutic effect is not particularly limited, provided that the disease is one in which the preventive and/or therapeutic effect of the present compound is complemented and/or enhanced.

Examples of medicinal agents that complement and/or enhance the preventive and/or therapeutic effect of the present compound in aortic aneurysm include HMG-CoA reductase inhibitors, antihypertensives, and tetracycline antibiotics.

Examples of the HMG-CoA reductase inhibitors include pravastatin (sodium), simvastatin, fluvastatin (sodium), cerivastatin (sodium), itavastatin, atorvastatin (calcium hydrate), lovastatin, and pitavastatin (calcium).

Examples of the antihypertensives include calcium antagonists, angiotensin II antagonists, angiotensin converting enzyme inhibitors, phosphodiesterase 4 inhibitors, diuretics, prostaglandins, aldosterone antagonists, and sympathetic blocking agents.

Examples of the calcium antagonists include nifedipine, benidipine hydrochloride, diltiazem hydrochloride, verapamil hydrochloride, nisoldipine, nitrendipine, bepridil hydrochloride, amlodipine besilate, lomerizine hydrochloride, and efonidipine hydrochloride.

Examples of the angiotensin II antagonists include losartan (potassium), candesartan (cilexetil), valsartan, irbesartan, olmesartan (medoxomil), and telmisartan.

Examples of the angiotensin converting enzyme inhibitors include alacepril, imidapril hydrochloride, quinapril hydrochloride, temocapril hydrochloride, delapril hydrochloride, benazepril hydrochloride, captopril, trandolapril, perindopril erbumine, enalapril maleate, and lisinopril.

Examples of the phosphodiesterase 4 inhibitors include cilomilast, roflumilast, arofyiline, atizoram, cipamfylline, and rolipram.

Examples of the diuretics include acetazolamide, aminophylline, isosorbide, dichlorphenamide, spironolactone, trichlormethiazide, furosemide, mannitol, methazolamide, and mefruside.

Examples of the aldosterone antagonists include drospirenone, metyrapone, potassium canrenoate, canrenone, and eplerenone.

Examples of the tetracycline antibiotics include doxycycline.

Examples of the medicinal agents that complement and/or enhance the preventive and/or therapeutic effect of the present compound in cancer include alkylating agents, antimetabolites, anti-cancer antibiotics, plant-based preparations, hormonal agents, platinum compounds, topoisomerase inhibitors, kinase inhibitors, anti-CD20 antibodies, anti-HER2 antibodies, anti-EGFR antibodies, anti-VEGF antibodies, proteasome inhibitors, HDAC inhibitors, and immunomodulators.

Examples of the alkylating agents include cyclophosphamide, ifosfamide, dacarbazine, temozolomide, nimustine hydrochloride, ranimustine, bendamustine, thiotepa, and carboquone.

Examples of the antimetabolites include methotrexate, pemetrexed, fluorouracil, tegafur, tegafur uracil, tegafur gimestat otastat potassium, doxifluridine, capecitabine, cytarabine, gemcitabine hydrochloride, fludarabine, nelarabine, carmofur, and procarbazine hydrochloride.

Examples of the anti-cancer antibiotics include mitomycin C, doxorubicin hydrochloride, aclarubicin hydrochloride, pirarubicin hydrochloride, epirubicin, chromomycin A3, bleomycin, peplomycin sulfate, and therarubicin.

Examples of the plant-based preparations include irinotecan hydrochloride, etoposide, vincristine sulfate, vinblastine sulfate, vindesine sulfate, vinorelbine tartrate, docetaxelhydrate, eribulin mesylate, and paclitaxel.

Examples of the hormonal agents include estramustine sodium phosphate, flutamide, bicalutamide, goserelin acetate, leuprorelin acetate, tamoxifen citrate, toremifene citrate, anastrozole, letrozole, exemestane, mepitiostane, medroxyprogesterone acetate, epitiostanol, fosfestrol, fadrozole hydrochloride hydrate, abiraterone, fulvestrant, and aminoglutethdmide.

Examples of the platinum compounds include carboplatin, cisplatin nedaplatin, and oxaliplatin.

Examples of the topoisomerase inhibitors include topotecan, and sobuzoxane.

Examples of the kinase inhibitors include EGFR inhibitors such as erlotinib, gefitinib, and afatinib; HER2 inhibitors such as lapatinib; BCR-ABL inhibitors such as imatinib; ALK inhibitors such as crizotinib; and multi-kinase inhibitors such as regorafenib, and dasatinib.

Examples of the anti-CD20 antibodies include rituximab, ibritumomab, ibritumomab tiuxetan, and ocrelizumab.

Examples of the anti-HER2 antibodies include trastuzumab, trastuzumab emtansine, and pertuzumab.

Examples of the anti-EGFR antibodies include cetuximab, and panitumumab.

Examples of the anti-VEGF antibodies include bevacizumab.

Examples of the proteasome inhibitors include bortezomib.

Examples of the HDAC inhibitors include vorinostat.

Examples of the immunomodulators include thalidomide, lenalidomide, and pomalidomide.

Examples of the medicinal agents that complement and/or enhance the preventive and/or therapeutic effect of the present compound in pain include N-type calcium channel inhibitors, nitrogen oxide synthetase (NOS) inhibitors, and cannabinoid-2 receptor stimulating reagents.

Examples of the N-type calcium channel inhibitors include cilnidipine.

Examples of the nitrogen oxide synthetase (NOS) inhibitors include D-arginine, and $N^G$-monomethyl-L-arginine.

The mass ratio of the present compound and other medicinal agent is not particularly limited.

The medicinal agents may be administered in any combination of two or more.

The medicinal agents that complement and/or enhance the preventive and/or therapeutic effect of the present compound are not limited to the compounds that are currently available with the mechanisms above, but include compounds that will by available in the future.

To use the present invention compounds as a single drug or a companion drug with other drugs for the prevention and/or treatment of said diseases, preparations are usually formed in active substances and various additives or pharmaceutically acceptable excipients, and are administered as oral or parenteral preparation systemically or locally. The pharmaceutically acceptable excipients mean materials except active substances which are generally used for preparations. The pharmaceutically acceptable excipients are preferably excipients which are harmlessness, and do not show any pharmacological effect and inhibit treatment effect of the active substances at the dosage of the drug products. In addition, the pharmaceutically acceptable excipients can be used to enhance effectiveness of the active substances, make production of the drugs easy, stabilize quality and improve usability. Specifically, the material described in "Iyakuhintenkabutujiten" (yakujinippousha, 2000), (edited by nihonniyakuhinntennkazai kyokai)", etc. may be selected according to intentions.

Dosage forms for administration includes, for example, oral preparation (e.g. tablets, capsules, granules, powders, oral solutions, syrups, oral jelly agents, etc.), oro-mucosal preparation (e.g.: tablets for oro-mucosal application, sprays for oro-mucosal application, semi-solid preparations for oro-mucosal application, gargles, etc.), preparations for injection (e.g.: injections, etc.), preparations for dialysis (e.g.: dialysis agents, etc.), preparation for inhalation (e.g.: inhalations, etc.), preparation for ophthalmic application (e.g.: ophthalmic liquids and solutions, ophthalmic ointments, etc.), preparation for otic application (e.g.: ear preparation, etc.), preparations for nasal application (nasal preparations, etc.), preparation for rectal (e.g.: suppositories, semi-solid preparations for rectal application, enemas for rectal application, etc.), preparations for vaginal application (e.g.: tablets for vaginal use, suppositories for vaginal use, etc.) and preparation for cutaneous application (e.g.: solid preparations for cutaneous application, liquids and solutions for cutaneous application, sprays, ointment, creams, gels, patches, etc.).

[Oral Preparation]

Oral preparation include, for example, tablets, capsules, granules, powders, liquids and solution for oral administration, syrups, Jellies for oral administration, etc. As oral preparation, there are Immediate-release dosage forms showing a release pattern of active substances that is not intentionally modified and modified-release dosage forms are preparations showing modified pattern of active substances that is suitably modified for the desired purpose by means of a specific formulation design and/or manufacturing methods. Modified-release dosage forms include enteric-coated and extended-release preparations. Enteric-coated (delayed-release) preparations release the bulk of the active substances not in stomach but mainly in small intestine, in order to prevent degradation or decomposition of the active substances in stomach or to decrease the irritation of the active substances on stomach. Enteric-coated preparations are generally coated with an acid-insoluble enteric film. Extended-release preparations are designed to control the release rate and release period of active substances and to restrict the release to appropriate sites in the gastrointestinal tracts in order to decrease the dosing frequency and/or to reduce adverse or side effects. Extended-release preparations are generally prepared by using suitable agents that prolong the release of the active substances. Oral dosage forms such as capsules, granules and tablets can be coated with appropriate coating agents, such as sugars, sugar alcohols, or polymers, for the purpose of enabling the ingestion easy or of preventing degradation of the active substances.

(1) Tablets

Tablets are solid preparation having a desired shape and size, intended for oral administration, and include orally disintegrating tablets, chewable tablets, effervescent tablets, dispersible tablets, soluble tablets besides generally called tablets such as plain tablets, film-coated tablets, sugar-coated tablets, multi-layered tablets and pressure-coated tablets, etc. Plain tables are usually prepared according to the following methods (a), (b) and (c):

(a) Mix homogeneously active substances and excipients such as diluents, binders and disintegrators, granulate with water or a binder solution by suitable methods, mix with a lubricant, and then compress into a desired shape and size;
(b) Mix homogeneously active substances and excipients such as diluents, binders,
and disintegrators, and then directly compress, or compress after adding active substances and lubricant to granules previously prepared from excipients and then mixing homogeneously;
(c) Mix homogeneously active substances and excipients such as diluents and binders, moisten with a solvent, form into a certain shape and size, and then dry by a suitable methods; Film-coated tablets can be prepared, usually, by coating plain tablets using suitable coating agents such as polymers. Sugar-coated tablets can be prepared, usually, by coating plain tablets using suitable coating agents including sugars and sugar alcohols Multiple-layer tablets can be prepared by compressing granules of different compositions to form layered tablets by a suitable method. Pressure-coated tablets can be prepared by compressing granules to cover inner core tablets with different compositions. In addition, tablets can be prepared as enteric coated tablets or timed-release tablet by suitable well-known methods. Orally disintegrating tablets, chewable tablets, effervescent tablets, dispersible tablets, soluble tablets are tablets which are added distinct role by selecting suitable excipients, and can be prepared according to said methods. Orally disintegrating tablets are tablets which are quickly dissolved or disintegrated in the oral cavity; Chewable tablets are tablets which are administered by chewing; Effervescent tablets are tablets which are quickly dissolved or dispersed with bubbles in water; Dispersible tablets are tablets which are administered after having been dispersed in water; Soluble tablets are tablets which are administered after having been dissolved in water. Effervescent tablets can be prepared using suitable acidic substances and carbonates or hydrogen carbonates as excipients.

(2) Capsules

Capsules are preparations enclosed in capsules or wrapped with capsule bases, intended for oral administration. Capsules are classified into hard capsules and soft capsules. Hard capsules can be prepared by a method where a homogeneous mixture of active substances with diluents and other suitable excipients, or granules or formed masses prepared by a suitable methods, are filled into capsule shells as they are or after slight compression. Soft capsules can be prepared by a method where active substances and suitable excipients are mixed, enclosed by a suitable capsule base such as gelation plasticized by addition of glycerin, D-sorbitol, etc, and molded in a suitable shape and size. Capsules can be prepared as enteric-coated or extended-release capsules by a suitable well-known method. Coloring agents and preservatives, etc, may be added to the capsule bases.

(3) Granules

Granules are preparations prepared by granulation, and include effervescent granules besides generally called granules. Granules can be prepared by the following methods (a), (b), and (c);
(a) To powdery active substances add diluents, binders, disintegrators, or other suitable excipients, mix to homogenize, and granulate by a suitable method;
(b) To previously granulated active substances add excipients such as diluents, and mix to homogenize;
(c) To previously granulated active substances add excipients such as diluents, and granulate by a suitable method; Granules can be coated if necessary, and can be prepared as enteric-coated or extended-release granules. Effervescent granules can be prepared using suitable acidic substances and carbonates or hydrogen carbonates. Effervescent granules are granules which are quickly dissolved or dispersed with bubbles in water. Granules can be prepared as fine grain agents by adjusting particle size.

(4) Powders

Powders are preparations in powder form, and are usually prepared by homogeneously mixing active substances with diluents or other suitable excipients.

(5) Liquids and Solution for Oral Administration

Liquids and solution for oral administration are preparations in liquid form or flow able and viscous gelatinous state, and elixirs, suspensions, emulsions and lemonades are included in this category besides generally called Liquids and solution for oral administration. Liquids and solution for oral administration are usually prepared by dissolving, emulsifying or suspending active substances in purified water together with excipients, and by filtering if necessary. Elixirs are clear, sweetened and aromatic liquid preparations, containing ethanol, and are usually prepared by dissolving solid active substances or their extractives in ethanol and purified water, adding aromatic agents and sucrose, other sugars or sweetening agents, and clarifying by filtration or other procedure. Suspensions are liquid preparations of active substances suspended finely and homogeneously in a vehicle, and are usually prepared by adding suspending agent or other suitable excipients and purified water or oil to solid active substances, and suspending homogeneously as the whole by a suitable method. Emulsions are liquid preparations of active substances emulsified finely and homogeneously in a liquid vehicle, and are usually prepared by adding emulsifying agents and purified, water to liquid active substances, and emulsifying finely and homogeneously by a suitable method. In addition, Lemonades are sweet and sour, clear liquid preparations, intended for oral administration.

(6) Syrups

Syrups are viscous liquid or solid preparations containing sugars or sweetening agents, and include preparation for syrups. Syrups are usually prepared by dissolving, mixing, suspending or emulsifying active substances in a solution of sucrose, other sugars or sweetening agents, or in simple syrup. Where necessary, the mixture is boiled, and filtered while hot. Preparations for syrups are preparations in form of granules or powders, which becomes syrups by adding water. They may be termed "dry syrups". Preparations for syrups are usually prepared with, sugars or sweetening agents according to said preparation method of granules or powders.

(7) Jellies for Oral Administration

Jellies for oral administration are non-flowable gelatinous preparations having a certain shape and size, and usually prepared by mixing active substances with suitable excipients and polymer gel base, gelatinizing and forming into a certain shape and size by a suitable method.

[Preparation for Oro-Mucosal Application]

(1) Tablets for Oro-Mucosal Application

Tablets for oro-mucosal application are solid preparations having certain form, and include troches/lozenges, sublingual tablets, buccal tablets, mucoadhesive tablets and medicated chewing gums. Preparations for oro-mucosal application are usually prepared according to said method of tablets. Troches/lozenges are tablets for oro-mucosal application, which are gradually dissolved or disintegrated in the mouth; Sublingual tablets are tablets for oro-mucosal application, from which active substances are quickly dissolved sublingually and absorbed via the oral mucosa; Buccal tablets are tablets for oro-mucosal applications, from which the active substances are dissolved gradually between the cheek and teeth, and absorbed via the oral mucosa; Mucoadhesive tablets are tablets for oro-mucosal application that are applied by adhesion to the oral mucosa; Medicated chewing gams are tablets for oro-mucosal application, releasing active substances by chewing.

(2) Spray for Oro-Mucosal Application

Spray for oro-mucosal application are preparation that are applied active substances by spraying into the oral cavity in mist, powder, foam or paste forms, and are usually prepared by dissolving or suspending active substances and suitable excipients in a solvent, filter, where necessary, and fill into a container together with liquefied or compressed gas, or dissolving or suspending active substances and suitable excipients in a solvent, and fill into a container, and fit with a pump for spraying.

(3) Semi-Solid Preparations for Oro-Mucosal Application

Semi-solid preparations for oro-mucosal application are preparation in cream, gel or ointment forms, intended for application to the oral mucosa. Semi-solid preparations for oro-mucosal application are usually prepared by emulsifying active substances together with excipients using purified water and Oil component such as petrolatum, or by homogenizing active substances together with suitable excipients using polymer gel or oil and fats as the base. Creams are semi-solid preparations, which are in the form of oil-in-water or water-in-oil emulsions. Hydrophobic preparations in the form of water-in-oil emulsions may be termed "Oily creams". Creams are usually prepared by mixing homogeneously and emulsifying an oil-phase component and a water-phase component, both warmed, of which either one contains the active substances. There components have the following constituents. Oil-phase component: Vaseline, fatty alcohols, etc., with or without emulsifying agents or other suitable excipient Water-phase component: purified water with or without emulsifying agents or other suitable excipients. Gels are gelatinous preparations. There are aqueous gels and oily gels. Aqueous gels are usually prepared by adding polymers, other excipients and purified water to active substances, dissolving or suspending, and gelatinizing by warming and cooling or by adding gelatinizing agents. Oily gels are usually prepared by adding liquid oily bases such as glycols, fatty alcohols and other excipients to active substances and mixing. Ointments are semi-solid preparations, which dissolve or disperse active substances in a base. There are two types, hydrophobic ointments and hydrophilic ointments. Hydrophobic ointments are usually prepared by warming to melt hydrophobic bases such as fatty oils, waxes or paraffin, adding and mixing active substances in the base to be dissolved or dispersed, and kneading the whole to make homogeneous. Hydrophilic ointments are usually prepared by warming to melt hydrophilic bases such as macrogol, adding and mixing active substances in the bases, and kneading the whole to make homogenous.

(4) Preparations for Gargle

Preparations for gargle are liquid preparations intended to apply locally to the oral and throat cavities. Solid type preparations to be dissolved in water before use are also included in this category. Preparations for gargle are usually prepared by dissolving active substances in a solvent together with suitable excipients, and filtering where necessary. Solid preparations are prepared according to said method of tablets or granules.

[Preparation for Injection]

(1) Injections

Injections are sterile preparations to be administered directly into the body through skin, muscle or blood vessel, usually in form of a solution, a suspension or an emulsion of active substances, or of a solid that contains active substances to be dissolved or suspended before use, and include freeze-dried injections, powders, prefilled syringes, cartridges, parenteral infusions, implants/pellets and prolonged-release injections besides generally called injections. Injections are prepared by the following method (a) and (b):
(a) Dissolve, suspend or emulsify active substances with or without excipients in water for injection or an aqueous or non-aqueous vehicle homogeneously, fill into containers for injection, seal, and sterilize.
(b) Dissolve, suspend or emulsify active substances with or without excipients in water for injection or an aqueous or non-aqueous vehicle, and filtrate aseptically, or prepare aseptically a homogeneous liquid, fill into containers for injection, and seal;
Freeze-dried injections are usually prepared by dissolving active substances with or without excipients such as diluents in water for injection, sterilizing the solution by aseptic filtration, filling the filtrate directly into individual containers for injection and being freeze-dried, or dividing the filtrate in special containers, being freeze-dried and transferred into individual containers for injection. Powder for injections are usually prepared by filtrating aseptically a solution of active substances, obtaining powders by crystallization from the solution or mixing additionally the powders with sterilized excipients, and filling the powders into individual containers for injections. Prefilled syringes for injections are usually prepared by dissolving, suspending or emulsifying active substances with or without excipients in a vehicle, and filling into syringes. Cartridges are used by fixing in an injection device for exclusive use. Cartridges for injection are usually prepared by dissolving, suspending or emulsifying active substances with or without excipients in a vehicle, and filling into cartridges. Parenteral infusions are usually injections of not less than 100 mL, intended for intravenous administration. Implants/Pellets are solid or gel-like form injections, intended for subcutaneous or intramuscular administration by means of an implant device or operative treatment, for the purpose of releasing active substances for a long period of time. Implants/Pellets are usually prepared in a form of pellet, microsphere or gel using biodegradable polymers. Prolonged release injections are injections to be used four intramuscular administration, for the purpose of releasing active substances for a long period of time, and usually prepared by dissolving or suspending active substances in a non-aqueous vehicle such as vegetable oil, or by suspending microspheres prepared with biodegradable polymers.

[Preparations for Dialysis]

(1) Dialysis Agents

Dialysis agents are preparations in liquid, or in solid which are to be dissolved before use, intended for peritoneal dialysis or hemodialysis, and include peritoneal dialysis agents and hemodialysis agents. Peritoneal dialysis agents are sterile dialysis agents, intended to be used for peritoneal dialysis, and are usually prepared by dissolving active substances with suitable excipients in a vehicle to make a certain volume, or by filling active substances combined with suitable excipients in a container, and sealing it. Sterilize if necessary. In the case of solid preparations to be dissolved before use, it can be prepared according to said preparation method of tablets or granules. Hemodialysis agents are dialysis agents to be used for hemodialysis, and are usually prepared by dissolving active substances with excipients in a vehicle to make a certain volume, or by filling active substances with excipients in a container. In the case of the solid preparations to be dissolved before use, it can be prepared according to said preparation method of tablets or granules.

[Preparation for Inhalation]

(1) Inhalations

Inhalations are preparations intended for administration as aerosols to the bronchial tubes or lung. Inhalations are classified to dry powder inhalers, inhalation liquid preparations and metered-dose inhalers. Dry powder inhalers are preparations which deliver a constant respiratory intake, intended for administration as solid particle aerosols, and are usually prepared by pulverizing active substances into fine particles. Where necessary, lactose or other suitable excipients are added to make homogeneous mixture. Inhalation Liquid preparations are liquid inhalations which are administered by an inhalation device such as operating nebulizer. Inhalation liquid preparations are usually prepared by mixing active substances with a vehicle and suitable isotonic agents and/or pH adjusting agents to make a solution or suspension, and by filtering where necessary. Metered-dose inhalers are preparations which deliver a constant dose of active substances from the container together with propellant filled in. Metered-dose inhalers are usually prepared by dissolving active substances with a suitable dispersing agents and stabilizers in a vehicle to make a solution or suspension, and by filling in pressure-resistant containers together with liquid propellant, and setting metering valves.

[Preparation for Ophthalmic Application]

(1) Ophthalmic Liquids and Solutions

Ophthalmic liquids and solutions are sterile preparations of liquid, or solid to be dissolved or suspended before use, intended for application to the conjunctival sac or other ocular tissues. Ophthalmic liquids and solutions are usually prepared by dissolving, suspending active substances in a vehicle after adding excipients to make a constant volume, or mixing active substances and excipients, and filling into containers.

(2) Ophthalmic Ointments

Ophthalmic ointments are sterile preparations semi-solid, intended for application to the conjunctival sac and other ocular tissues. Ophthalmic ointments are usually prepared by mixing homogeneously solution of or finely powdered active substances with petrolatum or other bases, and filling into containers.

[Preparation for Otic Application]

(1) Ear Preparation

Ear preparations are liquid, semi-solid, or solid preparations which are to be dissolved or suspended before use, intended for application to the external or internal ear. Ear preparations are usually prepared by filling in containers with Liquids in which active substances and excipients are dissolved or suspended in a vehicle to make a constant volume, or with powders in which active substances and excipients are mixed.

[Preparations for Nasal Application]

(1) Nasal Preparations

Nasal preparations are preparations intended for application to the nasal cavities or nasal mucous membrane. Nasal preparations are classified into Nasal dry powder inhalers and Nasal liquid preparations. Nasal dry powder inhalers are fine powdered preparations, intended for application to the nasal cavities. Nasal dry powder inhalers are usually prepared by pulverizing active substances into moderately fine particles, or by mixing homogeneously with excipients where necessary. Nasal liquids and solutions are liquid preparations, or solid preparations to be dissolved or suspended before use, intended for application to the nasal cavities. Nasal liquids and solutions are usually prepared by dissolving or suspending active substances in a vehicle together with excipients, and filtering where necessary. Isotonic agents and/or pH adjusting agents may be used.

[Preparations for Rectal Application]

(1) Suppositories for Rectal Application

Suppositories for rectal application are semi-solid preparations of a desired shape and size, intended for intrarectal application, which release active substances by melting at body temperature or dissolving or dispersing gradually in the secretions. Suppositories for rectal application are usually prepared by mixing homogeneously active substances and excipients such as dispersing agents and emulsifying agents, dissolving or suspending uniformly in a base which is liquefied by warming, filling a constant volume of the resultant material into containers, and molding it into a shape and size. Lipophilic bases or hydrophilic bases are usually used.

(2) Semi-Solid Preparations for Rectal Application

Semi-solid preparations for rectal application are preparations which are in a form of cream, gel or ointment intended for application to around or inside of the anus. Semi-solid preparations for rectal application are usually prepared by emulsifying active substances with excipients in purified water and oil component such as Vaseline, or by homogeneously mixing active substances and excipients in a base of polymer gel or grease. Creams for rectal application are usually prepared by mixing homogeneously and emulsifying an oil-phase component (such as vaseline, fatty alcohols, etc.) and a water phase component (such as purified water with or without emulsifying agents or other suitable excipients), both warmed, of which either one contains the active substances. Gels for rectal application are gelatinous preparation. There are aqueous gels and oily gels. Aqueous gels are prepared adding polymers, other excipients and purified water to active substances, and dissolving or suspending, and gelatinizing by warming and cooling or by adding gelatinizing agents. Oily gels are prepared by adding liquid oily bases such as glycols, fatty alcohols and other excipients to active substances and mixing. Ointments for rectal application are semi-solid preparations, which dissolve or disperse active substances in a base. There are two types, hydrophobic ointment and hydrophilic ointments. Hydrophobic ointments are usually prepared by warming to melt hydrophobic bases such as fatty oils, waxes or paraffin, adding and mixing active substances in the bases to be dissolved or dispersed, and kneading the whole to make homogeneous. Hydrophilic ointments are usually prepared by warming to melt hydrophilic bases such as macrogol, adding and mixing active substances in the bases, and kneading the whole to make homogeneous.

(3) Enemas for Rectal Application

Enemas for rectal application are preparations in liquid form or viscous and gelatinous state, intended for applications via anus. Enemas for rectal application are preparations are usually prepared by dissolving or suspending active substances in purified water or suitable aqueous vehicle: to make a given volume, and filling in containers. Dispersing agents, stabilizers and/or pH adjusting agents may be used.

[Preparations for Vaginal Application]

(1) Tablets for Vaginal Use

Tablets for vaginal use are solid applications of a desired shapes and size, intended for application to the vagina, which release active substances by dissolving or dispersing gradually in the secretions. Tablets for vaginal use are usually prepared according to said preparation method of tablets.

(2) Suppositories for Vaginal Use

Suppositories for vaginal use are semi-solid preparations of a desired shapes and size, intended for application to the vagina, which release active substances by melting at body temperature or by dissolving or dispersing gradually in the secretions. Suppositories for vaginal use are usually prepared according to said preparation method of suppositories for rectal applications.

[Preparation for Cutaneous Application]

(1) Solid Preparations for Cutaneous Application

Solid preparations for cutaneous application are solid preparations intended for application to the skin (including scalp) or nails. Powders for cutaneous application are included in this category. Powders for cutaneous application are powdery solid preparations intended for external application. Powders for cutaneous application are usually prepared by mixing homogeneously active substances and excipients such as diluents and pulverizing the mixture.

(2) Liquids and Solutions for Cutaneous Application

Liquids and solutions for cutaneous application are liquid preparations intended for application to the skin (including scalp) or nails. Liniments and lotions are included in this category. Liquids and solutions for cutaneous application are usually prepared by mixing active substances and excipients in a vehicle, and filtering if necessary. Liniments are liquid or muddy preparations intended for external application to the skin by rubbing. Lotions are external liquids in which active substances are dissolved, emulsified or finely dispersed in an aqueous vehicle. Lotions are usually prepared by dissolving, suspending or emulsifying active substances in purified water with excipients and making homogeneous as a whole.

(3) Spray for Cutaneous Application

Spray for cutaneous application are preparations intended for spraying active substances onto the skin in mists, powders, forms or paste state. Spray for cutaneous application are classified into aerosols for cutaneous application and pump sprays for cutaneous application. Spray for cutaneous applications are usually prepared by dissolving or suspending active substances in a vehicle, filtering where necessary, and filling in containers. Aerosols for cutaneous application are sprays which atomize active substances together with liquefied or compressed gas filled in containers. Aerosols for cutaneous application are usually prepared by dissolving or suspending active substances in a vehicle, filling with liquefied propellants in pressure-resistant containers, and setting a continuous spray valve. If necessary, dispersing agents and stabilizer may be used. Pump sprays for cutaneous application are sprays which atomize active substances in containers by pumping. Pump sprays for cutaneous application are usually prepared by dissolving or suspending active substances with excipients in a vehicle, filling in containers and setting pumps to the containers.

(4) Ointments

Ointments are semi-solid preparations to be applied to the skin, which dissolve or disperse active substances in a base. There are two types, hydrophobic ointments and hydrophilic ointments. Hydrophobic ointments are usually prepared by warming to melt hydrophobic bases such as fatty oils, waxes or paraffin, adding and mixing active substances in the base to be dissolved or dispersed, and Kneading the whole to make homogeneous. Hydrophilic ointments are usually prepared by warming to melt hydrophilic bases such as macrogol, adding and mixing active substances in the bases, and kneading the whole to make homogenous.

(5) Creams

Creams are semi-solid preparations to be applied to the skin, which are in the form of oil-in-water or water-in-oil emulsions. Hydrophobic preparations in the form of water-in-oil emulsions may be termed "Oily creams". Creams are usually prepared by mixing homogeneously and emulsifying an oil-phase component and a water-phase component, both warmed, of which either one contains the active substances. There components have the following constituents. Oil-phase component: Vaseline, fatty alcohols, etc., with or without emulsifying agents or other suitable excipients. Water-phase component: purified water with or without emulsifying agents or other suitable excipients.

(6) Gels

Gels are gelatinous preparations intended for application to the skin. There are aqueous gels and oily gels. Aqueous gels are usually prepared by adding polymers, other excipients and purified water to active substances, dissolving or suspending, and gelatinizing by warming and cooling or by adding gelatinizing agents. Oily gels are usually prepared by adding liquid oily bases such as glycols, fatty alcohols and other excipients to active substances and mixing.

(7) Patches

Patches are preparations intended to the attached on the skin. Patches are classified into Tapes/Plasters and Cataplasms/Gel patches. Patches are usually prepared by mixing active substances homogeneously with a base such as a polymer or a mixture of polymers, spreading on a backing layer or liner, and cutting into a given size. Percutaneous absorption type preparations may be prepared by using a release rate-controlling membrane. Where necessary, adhesive agents or penetration enhancers may be used. Tapes/Plasters are patches which are prepared with bases of practically no water contain. Tapes/Plasters are usually prepared by mixing homogeneously active substances with or without excipients and R base of non water-soluble natural or synthetic polymers such as resins, plastics or rubber, and spreading on a cloth or spreading and sealing on a cloth or plastic film, cutting into a given size. The preparations may be also prepared by filling a mixture of active substances and a base with or without other excipients in releasers composed with a release-controlling film, supporter and liner. Cataplasms/Gels are patches using water containing bases. Cataplasms/Gels patches are usually prepared by mixing active substances, purified water, and glycerin or other liquid materials, or by mixing and kneading natural or synthetic polymers, which are soluble in water or absorbent of water, with purified water, adding active substances, mixing the whole homogeneously, spreading on a cloth or film, and cutting into a given size.

Unless otherwise defined, all technical and scientific terms, and all abbreviations used in this specification have the meaning as normally understood by a skilled person in the art to which the present invention pertains.

The contents of the all patent documents and non-patent documents, and the contents of the reference documents explicitly cited herein are incorporated herein as a part of the specification.

EXAMPLES

The present invention is described below in Greater detail by way of Examples. It is to be noted that the present invention is not limited by the following descriptions.

The solvents in parentheses shown in connection with the separation positions in chromatography and with TLC represent the eluting solvents or developing solvents used. The proportions are volume ratios.

The solvents in parentheses shown in connection with NMR represent the solvents used for measurement.

As a rule, the compound names used in this specification are based on the computer program ACD/Name® or the Chemdraw Ultra (version 12.0, Cambridge Soft), which generate chemical names according to IUPAC rules. The compound names are also based on the IUPAC nomenclature.

Reference Example 1: 4-Methylenechromane

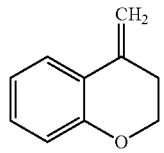

A solution of lithium bis(trimethylsilyl)amide in tetrahydrofuran (hereinafter, "THF") (1.3 mol/L, 931 mL) was dropped into a 1,500-mL THF solution of methyltriphenylphosphonium bromide (435 g) under a stream of nitrogen on ice, and the mixture was stirred at room temperature for 1 h. The mixture was further stirred at room temperature for 1 h after dropping a 180-ml, THF solution of 4-chromanone (150 g) at −5° C. After adding a saturated ammonium chloride aqueous solution to the reaction mixture on ice, the mixture was extracted with ethyl acetate. The organic layer was washed with saturated brine, dried over anhydrous sodium sulfate, and concentrated under reduced pressure. The resulting residue was then purified by silica gel column chromatography to obtain the title compound (75.9 g) having the following physical property values.

TLC: Rf 0.62 (hexane:ethyl acetate=9:1);
$^1$H-NMR (CDCl$_3$): δ 2.59-2.75, 4.18-4.31, 4.89, 5.51, 6.79-6.94, 7.12-7.20, 7.56.

Reference Example 2: Ethyl (2'R,4S)-2,3-dihydrospiro[chromene-4,1'-cyclopropane]-2'-carboxylate

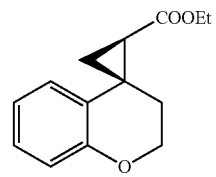 [SMILES: CCOC(=O)[C@@H]1C[C@]12CCOc1ccccc12]

Under a stream of nitrogen, a dichloro(p-cymene)ruthenium(II) dimer (15.8 g), and (S,S)-2,6-bis(4-isopropyl-2-oxazolin-2-yl)pyridine (15.6 g) were added to a dichloromethane solution (2,500 mL) of the compound (75.9 g) produced in Reference Example 1. A dichloromethane solution (150 mL) of diazoethyl acetate (containing 13% of dichloromethane, 134 g) was then slowly dropped at room temperature, and the mixture was stirred for 1 h. After adding a saturated ammonium chloride aqueous solution to the reaction mixture, the mixture was extracted with dichloromethane, and the organic layer was dried over anhydrous sodium sulfate, and concentrated under reduced pressure. The resulting residue was then purified by silica gel column chromatography to obtain the title compound (91.2 g) having the following physical property values.
$^1$H-NMR (CDCl$_3$): δ 1.26, 1.54-1.67, 2.07-2.22, 4.05-4.21, 4.27, 6.68, 6.78-6.89, 7.04-7.12.

Reference Example 3: (2'R,4S)-2,3-Dihydrospiro[chromene-4,1'-cyclopropane]-2'-carboxylic acid

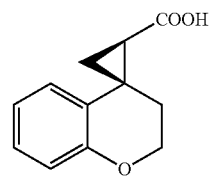 [SMILES: O=C(O)[C@@H]1C[C@]12CCOc1ccccc12]

An aqueous solution (160 mL) of lithium hydroxide monohydrate (29.6 g) was added to a methanol (400 mL) and 1,2-dimethoxyethane (400 mL) solution of the compound (91.2 g) produced in Reference Example 2, and the mixture was stirred overnight at room temperature. A 10% aqueous solution of citric acid was added to the reaction mixture, and the mixture was extracted with ethyl acetate. The organic layer was washed with saturated brine, dried over anhydrous sodium sulfate, and concentrated under reduced pressure. The resulting residue was then recrystallized with dichloromethane to obtain the title compound (55.2 g) having the following physical property values.
$^1$H-NMR (CDCl$_3$): δ 1.59-1.67, 1.68-1.76, 2.15, 2.21-2.29, 4.12-4.23, 4.25-4.36, 6.70, 6.80-6.92, 7.06-7.16;
HPLC retention time: 6.9 min (CHIRALPAK IC 4.6 mm×250 mm hexane:ethyl acetate:formic acid=97:3:1).

Reference Example 4: Methyl (2'R,4S)-2,3-dihydrospiro[chromene-4,1'-cyclopropane]-2'-carboxylate

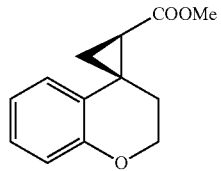 [SMILES: COC(=O)[C@@H]1C[C@]12CCOc1ccccc12]

Under a stream of nitrogen, potassium carbonate (28.5 q) was added to an N, N-dimethylformamide (hereinafter, "DMF") solution (200 mL) of the compound (40.0 g) produced in Reference Example 3. The mixture was stirred overnight at room temperature after dropping iodomethane (31.9 g). The reaction mixture was poured into ice water, and extracted with a hexane-ethyl acetate mixed solution. The organic layer was washed with water and saturated brine, dried over anhydrous sodium sulfate, and concentrated under reduced pressure to obtain the title compound (40.1 g) having the following physical property values.

TLC: Rf 0.30 (hexane:ethyl acetate=9:1);

$^1$H-NMR (CDCl$_3$): δ 1.57-1.69, 2.09-2.22, 3.71, 4.07-4.17, 4.27, 6.68, 6.18-6.90, 7.04-7.14.

Reference Example 5: Methyl (2'R,4S)-6-iodo-2,3-dihydrospiro[chromene-4,1'-cyclopropane]-2'-carboxylate

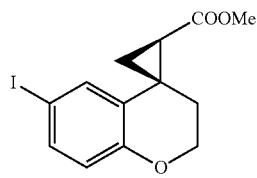 [SMILES: COC(=O)[C@@H]1C[C@]12CCOc1ccc(I)cc12]

Under a stream of nitrogen, 1,3-diiodo-5,5-dimethylhydantoin (35.6 g), and three droplets of concentrated sulfuric acid were added to a methanol solution (320 mL) of the compound (40.1 g) produced in Reference Example 4, on ice. The mixture was stirred for 1.5 h under the same condition, and for 2.5 h at room temperature. The reaction mixture was diluted with a hexane-ethyl acetate mixed solution, and washed with a saturated sodium bicarbonate aqueous solution. The aqueous layer was extracted with a hexane-ethyl acetate mixed solution. The organic layer was washed with water and saturated brine, dried over anhydrous sodium sulfate, and concentrated under reduced pressure to obtain the title compound (63.8 g) having the following physical property values.

TLC: Rf 0.33 (hexane:ethyl acetate=9:1);

$^1$H-NMR (CDCl$_3$): δ 1.60, 2.06-2.19, 3.71, 4.09, 4.20-4.31, 6.59, 0.93, 7.36.

Reference Example 6: (2'R,4S)-6-iodo-2,3-dihydrospiro[chromene-4,1'-cyclopropane]-2'-carboxylic acid

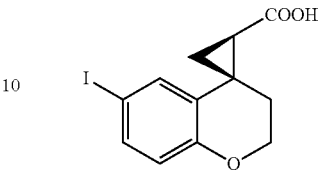

A sodium hydroxide aqueous solution (2 mol/L, 44 mL) was added to a methanol (60 mL) and 1, 2-dimethoxyethane (60 mL) solution of the compound (15.0 g) produced in Reference Example 5, and the mixture was stirred at room temperature for 1.5 h. After adding hydrochloric acid to the reaction mixture, the mixture was extracted with ethyl acetate. The organic layer was washed with water and saturated brine, dried over anhydrous sodium sulfate, and concentrated under reduced pressure to obtain the title compound (14.4 g) having the following physical property values.

TLC: Rf 0.42 (dichloromethane:methanol=9:1);

$^1$H-NMR (CDCl$_3$): δ 1.57-1.74, 2.11, 0.2.16-2.25, 4.10-4.20, 4.23-4.33, 6.59, 6.94, 7.37.

Reference Example 7: Ethyl 4-(4-formyl-2 nitrophenyl) butanoate

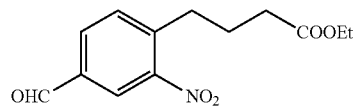 [SMILES: CCOC(=O)CCCc1ccc(C=O)cc1[N+](=O)[O-]]

Iodine (26.0 g) was added to a 700-ml, solution of a zinc powder (99.2 g) in N,N-dimethylacetamide (hereinafter, "DMA") under a stream of nitrogen, and the mixture was stirred for 10 min. After dropping ethyl 4-bromobutyrate (200 g), the mixture was stirred at 80° C. for 2 h to prepare a zinc reagent. Under a stream of nitrogen, 2-dicyclohexylphosphino-2',6'-dimethoxybiphenyl (7.14 g), and palladium acetate (1.96 g) were added to a 500-ml, THF solution of 3-nitro-4-bromobenzaldehyde (100 g), and the zinc reagent (500 rut) was dropped into the mixture on ice. This was followed by stirring at room temperature for 30 min. A saturated ammonium chloride aqueous solution, and water were added to the reaction mixture, and the mixture was extracted with ethyl acetate. The organic layer was washed with water and saturated brine, dried over anhydrous sodium sulfate, and concentrated under reduced pressure. The resulting residue was then purified by silica gel column chromatography to obtain the title compound (91.2 having the following physical property values.

TLC: Rf 0.61 (hexane e ethyl acetate=2:1);

$^1$H-NMR (CDCl$_3$): δ 1.27, 1.97-2.09, 2.42, 3.01, 4.15, 7.57, 8.04, 8.38, 10.03.

Reference Example 8: Ethyl 4-(4-cyano-2-nitrophenyl)butanoate

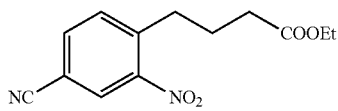 [SMILES: CCOC(=O)CCCc1ccc(C#N)cc1[N+](=O)[O-]]

Hydroxylamine hydrochloride (26.0 g) was added to a 350-mL DE solution of the compound (92.0 g) produced in Reference Example 7, and the mixture was stirred at 50° C. for 1 h. The mixture was stirred at 90° C. for 2 h after adding acetyl chloride (30 mL). Then, water was added to the reaction mixture, and the mixture was extracted with ethyl acetate. The organic layer was washed with water, a saturated sodium bicarbonate aqueous solution, and saturated brine, dried over anhydrous sodium sulfate, and concentrated under reduced pressure. The resulting residue was then purified by silica gel column chromatography to obtain the title compound (81.0 g) having the following physical property values.

TLC: Rf 0.65 (hexane:ethyl acetate=2:1);
$^1$H-NMR (CDCl$_3$): δ 1.27, L 92-2.10, 2.37-2.45, 2.91-3.06, 4.15, 7.55, 7.81, 8.21.

Reference Example 9: Ethyl 4-(2-amino-4-cyanophenyl)butanoate

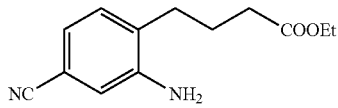

Palladium carbon (50% wet, 8.0 g) was added to an 80-mL ethanol solution of the compound (17.0 g) produced in Reference Example 8, and the mixture was stirred at room temperature for 9 h in a hydrogen atmosphere. After filtering the reaction mixture with Celite (trade name), the filtrate was concentrated to obtain the title compound (12.0 g) having the following physical property values.

TLC: Rf 0.56 (hexane:ethyl acetate=2:1);
$^1$H-NMR (CDCl$_3$): δ 1.28, 1.79-1.95, 2.38-2.45, 2.50-2.60, 4.09-4.30, 6.89, 6.93-6.98, 7.04-7.10.

Reference Example 10: Ethyl 4-[4-cyano-2-({[(2'R,4S)-6-iodo-2,3-dihydrospiro[chromene-4,1'-cyclopropan]-2'-yl]carbonyl}amino)phenyl]butanoate

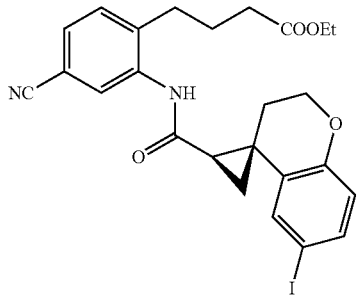 [SMILES: CCOC(=O)CCCc1ccc(C#N)cc1NC(=O)[C@@H]1C[C@]12CCOc1ccc(I)cc12]

4-methylmorpholine (24.0 mL), 4-dimethylaminopyridine (5.33 g), and a propylphosphonic acid anhydride cyclic trimer (hereinafter, "T3P"; 1.7 mol/L, 46.5 mL) were added to a 90-mL DMA solution of the compound (14.4 g) produced in Reference Example 6, and the compound (10.0 g) produced in Reference Example 9, and the mixture was stirred overnight at room temperature. Ethyl acetate, water, and a hydrochloric acid aqueous solution were added to the reaction mixture, and the mixture was extracted with ethyl acetate. The organic layer was washed with water, a saturated sodium bicarbonate aqueous solution, and saturated brine, dried over anhydrous sodium sulfate, and concentrated under reduced pressure. The resulting residue was then washed with a hexane-ethyl acetate mixed solution to obtain the title compound (19.3 g) having the following physical property values.

TLC: Rf 0.42 (hexane:ethyl acetate=2:1);
$^1$H-NMR (CDCl$_3$): δ 1.20, 1.61, 1.66-1.79, 1.83, 2.18-2.28, 2.39-2.49, 2.60, 3.66, 3.90, 4.00-4.12, 4.26, 6.58, 7.05, 7.15-7.22, 7.26-7.31, 7.33, 8.72, 9.39.

Reference Example 11: (2'R,4S)-2'-{[5-Cyano-2-(4-ethoxy-4-oxobutyl)phenyl]carbamoyl}-2,3-dihydrospiro[chromene-4,1'-cyclopropane]-6-carboxylic acid

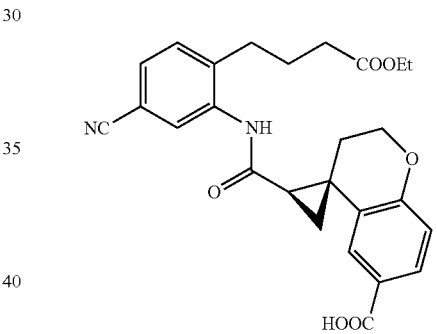

Sodium acetate (3.35 g) and [1,1'-bis(diphenylphosphino)ferrocene]palladium(II) dichloride dichloromethane complex (555 mg) were added to a 60-mL DMF solution of the compound (7.40 g) produced an Reference Example 10, and the mixture was stirred at 80° C. for 6 h in a carbon monoxide atmosphere. A potassium carbonate aqueous solution was added to the reaction mixture, and the mixture was stirred for some time. After adding tert-butyl methyl ether and water, the mixture was filtered with Celite (trade name). A hydrochloric acid aqueous solution was added to the filtrate, and the mixture was extracted with ethyl acetate. The organic layer was washed with water and saturated brine, dried ver anhydrous sodium sulfate, and concentrated under reduced pressure. The resulting residue was then purified by silica gel column chromatography (Yamazen Autopurification Device) to obtain the title compound (6.14 g) having the following physical property values.

TLC: Rf 0.48 (dichloromethane:ethyl acetate:methanol=8:4:1);
$^1$H-NMR (CDCl$_3$): δ 1.08, 1.65-1.80, 1.83-1.92, 2.25-2.36, 2.37-2.49, 2.55-2.66, 2.71, 3.55, 3.79, 4.12-4.23, 4.37, 6.88, 7.15-7.22, 7.27-7.32, 7.61, 7.83, 8.73, 9.40.

Reference Example 12: Ethyl 4-[4-cyano-2-({[(2'R,4S)-6-(methylcarbamoyl) 3-dihydrospiro[chromene-4,1'-cyclopropan]-2'-yl]carbonyl}amino)phenyl]butanoate

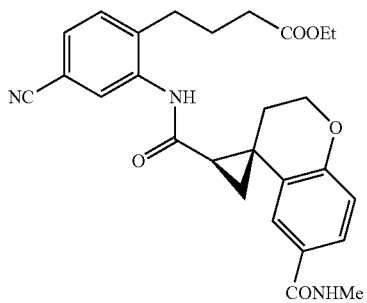

The title compound (53.0 mg) having the following physical property values was obtained by performing the procedures of Reference Example 10, except that the compound (60.0 mg) produced in Reference Example 11 was used instead of the compound produced in Reference Example 6, and that methylamine hydrochloride (87.5 mg) was used instead of the compound produced in Reference Example 9.

$^{1}$H-NMR (CDCl$_3$): δ 1.07, 1.64-1.79, 1.81-1.89, 2.20-2.35, 2.40, 2.60, 2.69, 2.98, 3.44-3.59, 3.68-3.03, 4.07-4.19, 4.27-4.38, 6.05, 6.82, 7.15-7.22, 7.27-7.32, 7.35-7.44, 0.72, 9.37.

Example 1: 4-[4-Cyano-2-({[(2'R,4S)-6-(methylcarbamoyl)-2,3-dihydrospiro[chromene-4,1'-cyclopropan]-2'-yl]carbonyl}amino)phenyl]butanoic acid

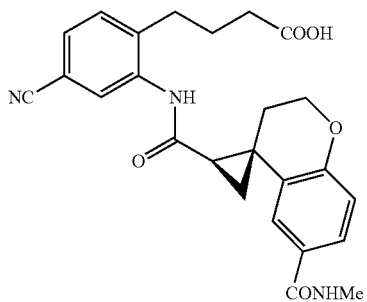

The present compound (45 mg) having the following physical property values was obtained by performing the procedures of Reference Example 6 using the compound (53 mg) produced in Reference Example 12. Ethanol was used instead of methanol.

TLC: Rf 0.45 (dichlorometnane:methanol=9:1);

$^{1}$H-NMR (CDCl$_3$): δ 1.21-1.30, 1.55, 1.65-1.82, 2.06-2.26, 2.38-2.67, 2.67-2.76, 3.02, 3.37, 4.33, 4.49-4.58, 6.25, 6.81, 7.19, 7.23-7.30, 7.94, 8.87, 9.93.

Example 2

The present compounds having the following physical property values were obtained by performing the same procedures from Reference Example 12 to Example 1, except that the methylamine hydrochloride was replaced with a corresponding amine compound.

Example 2-1: 4-{4-Cyano-2-[({(2'R,4S)-6-[(cyclopropylmethyl)carbamoyl]-2,3-dihydrospiro[chromene-4,1'-cyclopropan]-2'-yl}carbonyl)amino]phenyl}butanoic acid

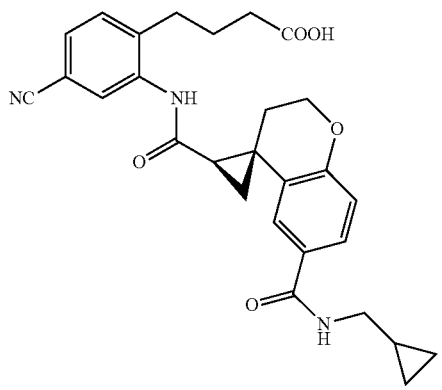 [SMILES: N#Cc1ccc(CCCC(=O)O)c(NC(=O)[C@@H]2C[C@]23CCOc2ccc(C(=O)NCC4CC4)cc23)c1]

TLC: Rf 0.45 (dichloromethane:methanol=9:1);

$^{1}$H-NMR (CDCl$_3$): δ 0.23-0.31, 0.52-0.63, 0.96-1.14, 1.22-1.30, 1.55, 1.66-1.81, 2.06-2.24, 2.38-2.66, 2.66-2.76, 3.31, 3.57, 4.34, 4.49-4.59, 6.31, 6.8:3, 7.19, 7.24-7.29, 7.32, 7.95, 8.87, 9.93.

Example 2-2: 4-{4-Cyano-2-[({(2'R,4S)-6-[(2-methoxyethyl)carbamoyl]-2,3-dihydrospiro[chromene-4,1'-cyclopropan]-2'-yl}carbonyl)amino]phenyl}butanoic acid

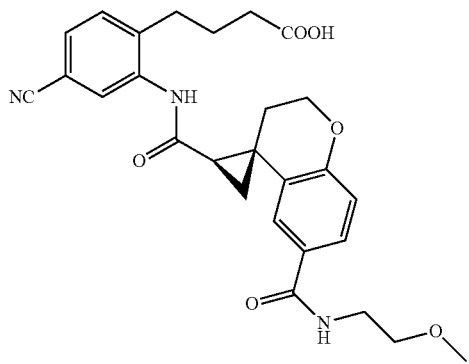 [SMILES: COCCNC(=O)c1ccc2c(c1)[C@]1(CCO2)C[C@H]1C(=O)Nc1cc(C#N)ccc1CCCC(=O)O]

Rf 0.51 (dichloromethane:methanol=9:1);

$^{1}$H-NMR (CDCl$_3$): δ 1.26, 1.55, 1.67-1.84, 2.06-2.27, 2.39-2.67, 2.67-2.78, 3.39, 3.51-3.78, 4.33, 4.49-4.59, 6.62, 6.82, 7.19, 7.24-7.29, 7.32, 7.92, 8.86, 9.88.

Example 2-3: 4-{4-Cyano-2-[({(2'R, 4S)-6-[(2-methyl-2-propanyl) carbamoyl]-2,3-dihydrospiro[chromene-4,1'-cyclopropan]-2'-yl}carbonyl)amino]phenyl}butanoic acid

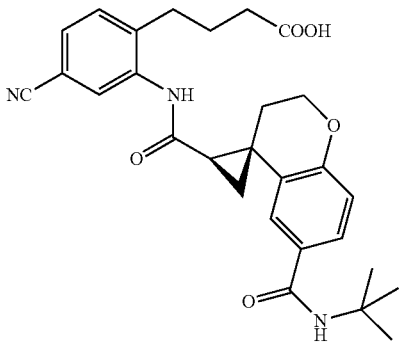 [SMILES: CC(C)(C)NC(=O)c1ccc2c(c1)[C@]1(CCO2)C[C@H]1C(=O)Nc1cc(C#N)ccc1CCCC(=O)O]

TLC: Rf 0.63 (chloroform:methanol=19:1);
¹H-NMR (DMSO-d$_6$): δ 1.37, 1.57, 1.64-1.85, 2.04-2.25, 2.42-2.48, 2.60-2.71, 4.01-4.15, 4.24-4.38, 6.80, 7.34-7.45, 7.52-7.66, 7.88, 9.89, 12.11.

Example 2-4: 4-[4-Cyano-2-({[(2'R,4S)-6-{[(2S)-1-methoxy-2-propanyl]carbamoyl}-2,3-dihydrospiro[chromene-4,1'-cyclopropan]-2'-yl]carbonyl}amino)phenyl]butanoic acid

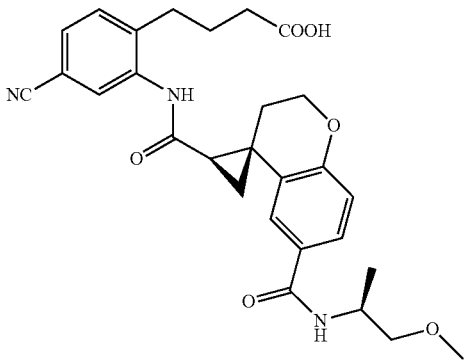 [SMILES: COC[C@H](C)NC(=O)c1ccc2c(c1)[C@]1(CCO2)C[C@H]1C(=O)Nc1cc(C#N)ccc1CCCC(=O)O]

TIC: Rf 0.62 (ethyl acetate:methanol=19:1);
¹H-NMR (CD$_3$OD): δ 1.22, 1.65-1.89, 2.12-2.26, 2.33, 2.62-2.77, 3.30-3.32, 3.37, 3.41, 3.47, 4.21-4.39, 6.82, 7.37-7.51, 7.58, 8.05.

Example 2-5: 4-{4-Cyano-2-[({2'R, 4S)-6-[(1-methyl 1H-pyrazol-4-yl)carbamoyl]-2,3-dihydrospiro[chromene-4,1'-cyclopropan]-2'-yl}carbonyl)amino]phenyl}butanoic acid TLC: Rf 0.51 (chloroform:methanol=9:1);
¹H-NMR (DMSO-d$_6$): δ 1.61, 1.66-1.87, 2.08-2.25, 2.50, 2.59-2.73, 3.81, 4.06-4.19, 4.28-4.42, 6.90, 7.41, 7.49-7.61, 7.73, 7.88, 7.99, 9.91, 10.19, 12.10.

Example 2-6: 4-{4-Cyano-2-[({(2'R, 4S)-6-[(3-methoxy-1-azetidinyl)carbamoyl]-2, 3-dihydrospiro[chromene-4, 1'-cyclopropan]-2'-yl}carbonyl)amino]phenyl}butanoic acid TLC: Rf 0.54 (ethyl acetate:methanol 19:1);
¹H-NMR (DMSO-d$_6$): δ 1.56, 1.67-1.80, 2.04-2.26, 2.45, 2.58-2.72, 3.21, 3.74-3.91, 4.06-4.27, 4.30, 4.37-4.51, 6.03, 7.10, 7.34-7.44, 7.57, 7.88, 9.89, 12.11.

Example 2-7: 4-{4-Cyano-2-[({(2'R, 4S)-6-[(1,3-oxazol-2-ylmethyl) carbamoyl]-2,3-dihydrospiro[chromene-4, 1'-cyclopropan]-2'-yl}carbonyl)amino]phenyl}butanoic acid TLC: Rf 0.64 (chloroform:methanol=9:1);
¹H-NMR (DMSO-d$_6$): δ 1.53-1.63, 1.65-1.83, 2.07-2.25, 2.48, 2.58-2.70, 4.03-4.16, 4.27-4.40, 4.47-4.64, 6.87, 7.10, 7.40, 7.48, 7.56, 7.67, 7.87, 8.04, 9.02, 9.90, 12.10.

Example 2-8: 4-[4-Cyano-2-({[(2'R,4S)-6-(1,3-oxazol-2-ylcarbamoyl)-2,3-dihydrospiro[chromene-4, 1'-cyclopropan]-2'-yl]carbonyl}amino)phenyl]butanoic acid TLC: Rf 0.40 (chloroform:methanol=9:1);
¹H-NMR (DMSO-d$_6$): δ 1.61, 1.66-1.80, 1.86, 2.11-2.25, 2.52, 2.61-2.72, 4.14, 4.38, 6.93, 7.19, 7.42, 7.54-7.65, 7.76, 7.88, 7.96, 9.92, 11.38, 12.10, Example 2-9: 4-{4-Cyano-2-[({(2'R,4S)-6-[(1-methyl-1H-pyrazol-yl)carbamoyl]-2,3-dihydrospiro[chromene-4,1'-cyclopropan]-2'-yl}carbonyl)amino]phenyl}butanoic acid

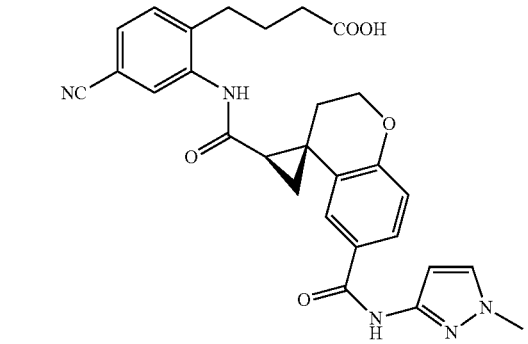 [SMILES: Cn1ccc(NC(=O)c2ccc3c(c2)[C@]2(CCO3)C[C@H]2C(=O)Nc2cc(C#N)ccc2CCCC(=O)O)n1]

TLC: Rf 0.62 (chloroform:methanol=9:1);
¹H-NMR (DMSO-d$_6$): δ 1.59, 1.67-1.81, 1.92, 2.10-2.25, 2.54, 2.60-2.72, 3.7.7, 4.12, 4.35, 6.59, 6.89, 7.42, 7.55-7.62, 7.68, 7.77, 7.88, 9.92, 10.75, 12.10.

Example 2-10: 4-[4-cyano-2-({[(2'R,4S)-6-(cyclopropylcarbamoyl)-2,3-dihydrospiro[chromene-4,1'-cyclopropan]-2'-yl]carbonyl}amino)phenyl]butanoic acid

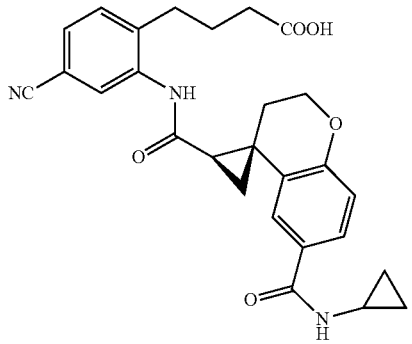 [SMILES: N#Cc1ccc(CCCC(=O)O)c(NC(=O)[C@@H]2C[C@]23CCOc2ccc(C(=O)NC4CC4)cc23)c1]

TLC: Rf 0.65 (ethyl acetate:methanol=19:1);
$^1$H-NMR (DMSO-d$_6$): δ 0.49-0.59, 0.65-0.75, 1.58, 1.66-1.82, 2.06-2.26, 2.47, 2.61-2.71, 2.81, 4.09, 4.34, 6.83, 7.36-7.45, 7.54-7.65, 7.88, 8.30, 9.89, 12.09.

Example 2-11: 4-[2-({[(2'R,4S)-6-(Butylcarbamoyl)-2,3-dihydrospiro[chromene-4,1'-cyclopropan]-2'-yl]carbonyl}amino)-4-cyanophenyl]butanoic acid TLC: Rf 0.79 (ethyl acetate:methanol=19:1);
$^1$H-NMR (CDCl$_3$): δ 0.93-1.00, 1.21-1.83, 2.06-2.25, 2.37-2.77, 3.41-3.50, 3.51-3.63, 4.33, 4.54, 6.18, 6.81, 7.15-7.31, 7.94, 8.87, 9.93.

Example 2-12: 4-[4-Cyano-2-({[(2'R,4S)-6-(cyclohexylcarbamoyl)-2,3-dihydrospiro[chromene-4,1'-cyclopropan]-2'-yl]carbonyl}amino)phenyl]butanoic acid TLC: Rf 0.86 (ethyl acetate:methanol=19:1);
$^1$H-NMR (CDCl$_3$): δ 1.10-1.87, 1.94-2.26, 2.38-2.79, 3.50-3.64, 3.85-4.04, 4.33, 4.54, 6.04, 6.81, 7.14-7.31, 7.93, 8.87, 9.93.

Example 2-13: 4-[4-Cyano-2-({[(2'R,4S)-6-(isopropylcarbamoyl)-2,3-dihydrospiro[chromene-4,1'-cyclopropan]-2'-yl]carbonyl}amino)phenyl]butanoic acid

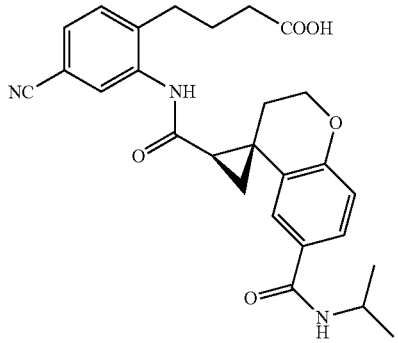 [SMILES: CC(C)NC(=O)c1ccc2c(c1)[C@]1(CCO2)C[C@H]1C(=O)Nc1cc(C#N)ccc1CCCC(=O)O]

TLC: Rf 0.74 (ethyl acetate:methanol=19:1);
$^1$H-NMR (CDCl$_3$): δ 1.27, 1.34-1.92, 2.01-2.30, 2.38-2.80, 3.50-3.61, 4.18-4.43, 4.54, 6.00, 6.81, 7.15-7.31, 7.94, 8.87, 9.93.

Example 2-14: 4-[4 Cyano 2-({[(2'R,4S)-6-(cyclopentylcarbamoyl)-2,3-dihydrospiro[chromene-4,1'-cyclopropan]-2'-yl]carbonyl}amino)phenyl]butanoic acid

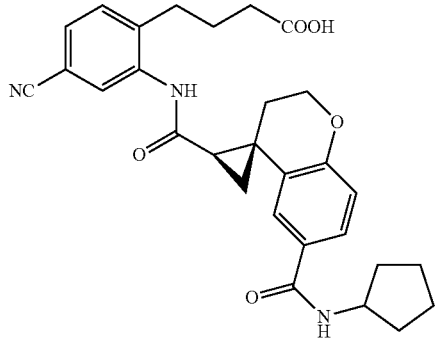 [SMILES: N#Cc1ccc(CCCC(=O)O)c(NC(=O)[C@@H]2C[C@]23CCOc2ccc(C(=O)NC4CCCC4)cc23)c1]

TLC: Rf 0.83 (ethyl acetate:methanol=19:1);
$^1$H-NMR (CDCl$_3$): δ 1.20-1.86, 2.00-2.26, 2.38-2.79, 3.50-3.64, 4.25-4.45, 4.46-4.61, 6.13, 6.81, 7.13-7.31, 7.94, 8.87, 9.93.

Example 2-15: 4-[4-Cyano-2-({[(2'R,4S)-6-(isobutylcarbamoyl)-2,3-dihydrospiro[chromene-4,1'-cyclopropan]-2'-yl]carbonyl}amino)phenyl]butanoic acid TLC: Rf 0.83 (ethyl acetate:methanol=19:1);
$^1$H-NMR (CDCl$_3$): δ 0.84-1.03, 1.21-2.01, 2.06-2.26, 2.37-2.79, 3.20-3.38, 3.51-3.62, 4.34, 4.49-4.59, 6.18-6.32, 6.82, 7.14-7.32, 7.94, 8.87, 9.93.

Example 2-16: 4-{2-[({(2'R,4S)-6-[(2S)-2-Butanylcarbamoyl]-2,3-dihydrospiro[chromene-4,1'-cyclopropan]-2'-yl}carbonyl)amino]4-cyanophenyl}butanoic acid

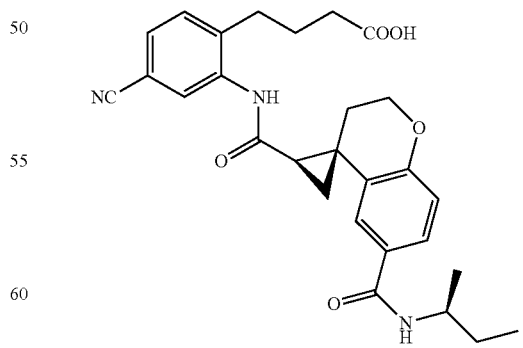

TLC: Rf 0.84 (ethyl acetate:methanol=20:1);
$^1$H-NMR (CDCl$_3$): δ 0.95, 1.18-1.91, 2.05-2.25, 2.39-2.78, 3.50-3.64, 4.03-4.20, 4.33, 4.48-4.60, 5.97, 6.81, 7.13-7.32, 7.94, 8.87, 9.93.

Example 2-17: 4-{2-[({(2'R,4S)-6-[(2R)-2-Butanylcarbamoyl]-2,3-dihydrospiro[chromene-4,1'-cyclopropan]-2'-yl}carbonyl)amino]-4-cyanophenyl}butanoic acid TLC: Rf 0.84 (ethyl acetate:methanol=20:1);

¹H-NMR (CDCl₃): δ 0.98, 1.18-1.32, 1.49-1.86, 2.05-2.25, 2.39-2.81, 3.57, 4.11, 4.33, 4.54, 5.95, 6.81, 7.13-7.33, 7.93, 8.81, 8.86, 9.93.

Example 2-18: 4-[2-({[(2'R,4S)-6-(Benzylcarbamoyl)-2,3-dihydrospiro[chromene-4,1'-cyclopropan]-2'-yl]carbonyl}amino)-4-cyanophenyl]butanoic acid TLC: Rf 0.84 (ethyl acetate:methanol=20:1);

¹H-NMR (CDCl₃): δ 1.20-1.86, 2.06-2.26, 2.40-2.79, 3.58, 4.34, 4.48-4.72, 6.47, 6.80, 7.15-7.42, 7.99, 8.87, 9.92.

Example 2-19: 4-{4-Cyano-2-[({(2'R,4S)-6-[(3R)-tetrahydro-3-furanylcarbamoyl]-2,3-dihydrospiro[chromene-4,1'-cyclopropan]-2'-yl}carbonyl)amino]phenyl}butanoic acid TLC: Rf 0.56 (ethyl acetate:methanol=19:1);

¹H-NMR (DMSO-d₆): δ 1.59, 1.67-1.83, 1.90, 2.07-2.26, 2.46, 2.61-2.71, 3.58, 3.72, 3.82-3.92, 4.10, 4.33, 4.48, 6.85, 7.38-7.48, 7.58, 7.67, 7.88, 8.39, 9.91, 12.11.

Example 2-20: 4-{4-Cyano-2-[({(2'R,4S)-6-[(trans-4-hydroxycyclohexyl)carbamoyl]-2,3-dihydrospiro[chromene-4,1'-cyclopropan]-2'-yl}carbonyl)amino]phenyl}butanoic acid

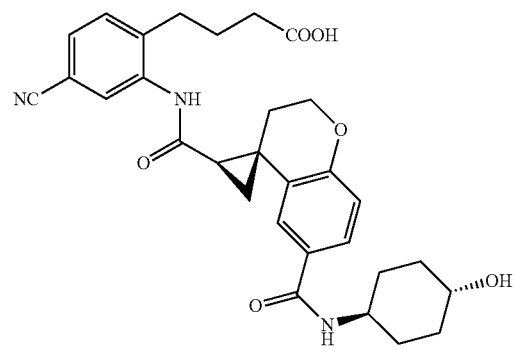 [SMILES: N#Cc1ccc(CCCC(=O)O)c(NC(=O)[C@@H]2C[C@]23CCOc2ccc(C(=O)N[C@H]4CC[C@H](O)CC4)cc23)c1]

TLC: Rf 0.57 (ethyl acetate:methanol=9:1);

¹H-NMR (CDCl₃): δ 0.77-1.85, 1.95-2.26, 2.38-2.77, 3.48-3.77, 3.83-4.04, 4.33, 4.54, 5.97, 6.81, 7.15-7.35, 7.92, 8.87, 9.92.

Example 2-21: 4-{4-Cyano-2-[({(2'R,4S)-6-[(cis-4-hydroxycyclohexyl)carbamoyl]-2,3-dihydrospiro[chromene-4,1'-cyclopropan]-2'-yl}carbonyl)amino]phenyl}butanoic acid

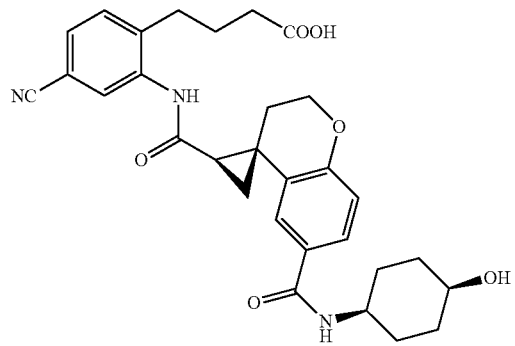 [SMILES: N#Cc1ccc(CCCC(=O)O)c(NC(=O)[C@@H]2C[C@]23CCOc2ccc(C(=O)N[C@H]4CC[C@@H](O)CC4)cc23)c1]

TLC: Rf 0.64 (ethyl acetate:methanol=9:1);

¹H-NMR (CDCl₃): δ 1.20-1.31, 1.51-1.86, 2.05-2.24, 2.38-2.79, 3.51-3.62, 3.94-4.09, 4.33, 4.54, 6.16, 6.82, 7.13-7.31, 7.92, 8.87, 9.92.

Example 2-22: 4-[4-Cyano-2-({[(2'R,4S)-6-{[2-(dimethylamino)ethyl]carbamoyl}-2,3-dihydrospiro[chromene-4,1'-cyclopropan]-2'-yl]carbonyl}amino)phenyl]butanoic acid TLC: Rf 0.17 (ethyl acetate:methanol=9:1, Chromatorex diol TLC plate (Fuji Silysia Chemical Ltd.));

¹H-NMR (CDCl₃) δ 1.19-1.34, 1.59, 1.66-1.84, 2.09-3.16, 3.38, 3.62-3.81, 4.33, 4.52, 6.85, 7.15-7.31, 7.52-7.64, 7.87, 8.80, 9.55.

Example 2-23: 4-[4-Cyano-2-({[(2'R,4S)-6-(2-pyridinylcarbamoyl)-2,3-dihydrospiro[chromene-4,1'-cyclopropan]-2'-yl]carbonyl}amino)phenyl]butanoic acid

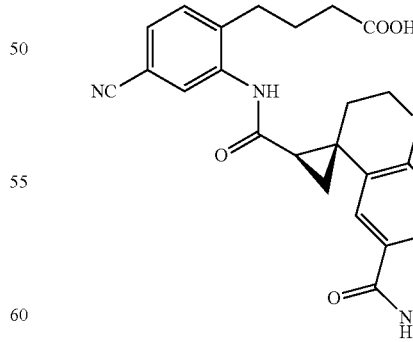

TLC: Rf 0.83 (ethyl acetate:methanol=19:1);

¹H NMR (DMSO-d₆): δ 1.58, 1.73, 1.88-1.99, 2.10-2.24, 2.60-2.70, 4.06-4.18, 4.30-4.40, 6.90, 7.14, 7.41, 7.57, 7.72, 77-7.90, 8.18, 8.38, 9.91, 10.78, 12.09.

Example 2-24: 4-{4-Cyano-2-[({(2'R,4S)-6-[(2-pyridinylmethyl)carbamoyl]-2,3-dihydrospiro[chromene-4,1'-cyclopropan]-2'-yl}carbonyl)amino]phenyl}butanoic acid TLC: Rf 0.62 (ethyl acetate:methanol=9:1);
<sup>1</sup>H-NMR (DMSO-d<sub>6</sub>): δ 1.58, 1.63-1.84, 2.01-2.24, 2.59-2.69, 4.04-4.16, 4.27-4.39, 4.55, 6.87, 7.22-7.33, 7.40, 7.55, 7.66-7.80, 7.87, 8.45-8.55, 9.01, 9.90, 12.09.

Example 2-25: 4-[4-Cyano-2-({[(2'R,4S)-6-{[(2R)-1-methoxy-2-propanyl]carbamoyl}-2,3-dihydrospiro[chromene-4, 1'-cyclopropan]-2'-yl]carbonyl}amino)phenyl]butanoic acid TLC: Rf 0.76 (ethyl acetate:methanol=19:1);
$^1$H-NMR (DMSO-d$_6$): δ 1.12, 1.59, 1.67-1.83, 2.08-2.25, 2.47, 2.61-2.70, 3.23-3.31, 3.40, 4.09, 4.20, 4.33, 6.85, 7.39-7.46, 7.58, 7.65, 7.89, 8.09, 9.90, 12.11.

Example 2-26: 4-{4-Cyano-2-[({(2'R,4S)-6-[(3-oxetanylmethyl)carbamoyl]-2, 3-dihydrospiro[chromene-4,1'-cyclopropan]-2'-yl}carbonyl)amino]phenyl}butanoic acid TLC: Rf 0.56 (chloroform:methanol=9:1);
$^1$H-NMR (DMSO-d$_6$): δ1.59, 1.66-1.80, 2.09-2.25, 2.46, 2.61-2.71, 3.15, 3.52, 4.10, 4.28-4.39, 4.63, 6.85, 7.37-7.47, 7.57-7.64, 7.89, 8.50, 9.92, 12.10.

Example 2-27: 4-{4-Cyano-2-[({(2'R,4S)-6-[(3S)-tetrahydro-3-furanylcarbamoyl]-2,3-dihydrospiro[chromene-4,1'-cyclopropan]-2'-yl}carbonyl)amino]phenyl}butanoic acid TLC: Rf 0.50 (ethyl acetate:methanol=19:1);
$^1$H-NMR (DMSO-d$_6$): δ 1.51-1.63, 1.64-1.97, 2.04-2.28, 2.41-2.47, 2.60-2.70, 3.58, 3.64-3.77, 3.80-3.92, 4.02-4.16, 4.26-4.38, 4.38-4.53, 6.84, 7.36-7.48, 7.58, 7.67, 7.87, 8.37, 9.91, 12.10.

Example 2-28: 4-{4-Cyano-2-[({(2'R,4S)-6-[(cyclobutylmethyl)carbamoyl]-2, 3-dihydrospiro[chromene-4, 1'-cyclopropan]-2'-yl}carbonyl)amino]phenyl}butanoic acid TLC: Rf 0.63 (dichloromethane:methanol=9:1);
$^1$H-NMR (DMSO-d$_6$): δ 1.52-1.62, 1.62-1.88, 1.88-2.06, 2.06-2.24, 2.60-2.70, 3.23-3.30, 4.01-4.14, 4.26-4.37, 6.83, 7.36-7.45, 7.59, 7.88, 8.31, 9.91, 12.10.

Example 2-29: 4-[4-Cyano-2-({[(2'R,4S)-6-(3-pyridazinylcarbamoyl)-2,3-dihydrospiro[chromene-4,1'-cyclopropan]-2'-yl]carbonyl}amino)phenyl]butanoic acid

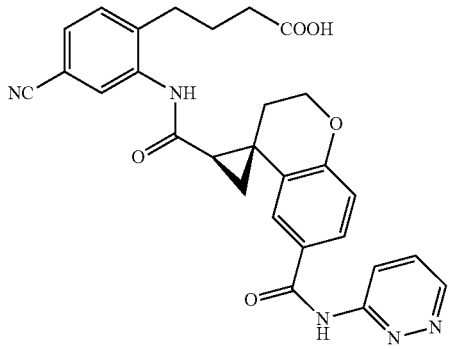 [SMILES: N#Cc1ccc(CCCC(=O)O)c(NC(=O)[C@@H]2C[C@]23CCOc2ccc(C(=O)Nc4cccnn4)cc23)c1]

TLC: Rf 0.65 (dichloromethane:methanol=9:1);
$^1$H-NMR (DMSO-d$_6$): δ 1.59, 1.72, 1.87-1.99, 2.05-2.24, 2.54-2.70, 4.05-4.23, 4.30-4.44, 6.93, 7.41, 7.57, 7.72, 7.76-7.93, 8.38, 9.00, 9.99, 11.45, 12.11.

Example 2-30: 4-{4-Cyano-2-[({(2'R,4S)-6-[(1-methyl-4-piperidinyl)carbamoyl]-2,3-dihydrospiro[chromene-4,1'-cyclopropan]-2'-yl}carbonyl)amino]phenyl}butanoic acid TLC: Rf 0.21 (dichloromethane:methanol:28% ammonia water=4:1:0.1);
$^1$H-NMR (DMSO-d$_6$): δ 1.49-1.83, 1.90-2.06, 2.06-2.24, 2.65, 2.81, 3.73, 4.02-4.15, 4.26-4.37, 6.83, 7.37-7.46, 7.56, 7.63, 7.90, 8.14, 10.01.

Example 2-31: 4-[4-Cyano-2-({[(2'R,4S)-6-(1H-pyrazol-4-ylcarbamoyl)-2,3-dihydrospiro[chromene-4,1'-cyclopropan]-2'-yl]carbonyl}amino)phenyl]butanoic acid TLC: Rf 0.45 (dichloromethane:methanol=9:1);
$^1$H-NMR (CD$_3$OD): δ 1.65-1.90, 2.24, 2.35, 2.60-2.80, 4.20-4.42, 6.89, 7.39-7.50, 7.59, 7.70, 7.89, 8.03.

Example 2-32: 4-{4-Cyano-2-[({(2'R,4S)-6-[(2,2-difluoroethyl)carbamoyl]-2,3-dihydrospiro[chromene-4,1'-cyclopropan]-2'-yl}carbonyl)amino]phenyl}butanoic acid TLC: Rf 0.76 (ethyl acetate:methanol=19:1);
$^1$H-NMR (DMSO-d$_6$): δ1.53-1.81, 2.06-2.25, 2.41-2.47, 2.58-2.71, 3.55-3.78, 4.04-4.17, 4.25-4.40, 5.84-6.36, 6.87, 7.41, 7.48, 7.55, 7.67, 7.87, 8.73, 9.91, 12.10.

Example 2-33: 4-[4-Cyano-2-({[(2'R,4S)-6-{[(3S)-1-methyl-3-pyrrolidinyl]carbamoyl}-2,3-dihydrospiro[chromene-4,1'-cyclopropan]-2'-yl]carbonyl}amino)phenyl]butanoic acid TLC: Rf 0.33 (dichloromethane:methanol=9:1);
$^1$H-NMR (DMSO-d$_6$): δ 1.50-1.59, 1.62-1.84, 2.06-2.23, 2.37, 2.64, 2.74-2.84, 4.14, 4.24-4.36, 4.45, 6.83, 7.35-7.48, 7.55, 7.63, 7.98, 8.45, 10.09.

Example 2-34: 4-[4-Cyano-2-({[(2'R,4S)-6-(1,3-thiazol-2-ylcarbamoyl)-2,3-dihydrospiro[chromene-4,1'-cyclopropan]-2'-yl]carbonyl}amino)phenyl]butanoic acid TLC: Rf 0.68 (dichloromethane:methanol=9:1);
$^1$H-NMR (DMSO-$d_6$): δ1.56-1.64, 1.65-1.81, 1.86-1.96, 2.10-2.24, 2.60-2.70, 4.07-4.19, 4.32-4.43, 6.94, 7.26, 7.41, 7.53-7.60, 7.79, 7.82-7.90, 9.92, 12.11, 12.53.

Example 2-35: 4-[4-Cyano-2-({[(2'R,4S)-6-(3-pyridinylcarbamoyl)-2,3-dihydrospiro[chromene-4,1'-cyclopropan]-2'-yl]carbonyl}amino)phenyl]butanoic acid TLC: Rf 0.53 (dichloromethane:methanol=9:1);
$^1$H-NMR (DMSO-$d_6$): δ 1.58-1.65, 1.72, 1.83, 2.08-2.24, 2.61-2.70, 4.30-4.43, 6.94, 7.35-7.45, 7.57, 7.79, 7.88, 8.11-8.18, 8.30, 8.90, 9.93, 10.24, 12.09.

Example 2-36: 4-[4-Cyano-2-({[(2'R,4S)-6-(2-pyrimidinylcarbamoyl)-2,3-dihydrospiro[chromene-4,1'-cyclopropan]-2'-yl]carbonyl}amino)phenyl]butanoic acid TLC: Rf 0.56 (dichloromethane:methanol=9:1);
$^1$H-NMR (DMSO-$d_6$): δ1.53-1.63, 1.63-1.80, 1.84-1.95, 2.07-2.24, 2.60-2.70, 4.06-4.19, 4.29-4.43, 6.90, 7.24, 7.41, 7.57, 7.64, 7.75, 7.86, 8.72, 9.91, 10.94, 12.08.

Example 2-37: 4-[4-Cyano-2-({[(2'R,4S)-6-(1,2-oxazol-3-ylcarbamoyl)-2,3-dihydrospiro[chromene-4,1'-cyclopropan]-2'-yl]carbonyl}amino)phenyl]butanoic acid TLC: Rf 0.65 (dichloromethane:methanol=9:1);
$^1$H-NMR (DMSO-$d_6$): δ 1.36-1.50, 1.62, 1.86-2.15, 2.53-2.68, 2.68-2.89, 4.19-4.37, 6.85, 6.91, 7.31-7.41, 7.41-7.49, 7.62, 7.79, 8.36, 8.75, 11.61, 12.62.

Example 2-38: 4-[4-Cyano-2-({[(2'R,4S)-6-(cyclobutylcarbamoyl)-2,3-dihydrospiro[chromene-4,1'-cyclopropan]-2'-yl]carbonyl}amino)phenyl]butanoic acid

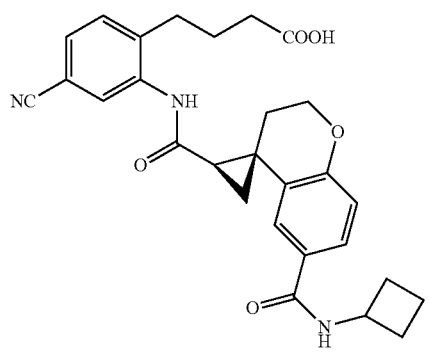 [SMILES: N#Cc1ccc(CCCC(=O)O)c(NC(=O)[C@@H]2C[C@]23CCOc2ccc(C(=O)NC4CCC4)cc23)c1]

TLC: Rf 0.72 (ethyl acetate);
$^1$H-NMR (CD$_3$OD): δ 1.62-1.90, 2.02-2.44, 2.59-2.80, 4.19-4.30, 4.33, 4.49, 6.82, 7.37-7.51, 7.58, 8.04.

Example 2-39: 4-[4-Cyano-2-({[(2'R,4S)-6-{1-(2-methyl-2-propanyl)-1H-pyrazol-4-yl]carbamoyl}-2,3-dihydrospiro[chromene-4,1'-cyclopropan]-2'-yl]carbonyl}amino)phenyl]butanoic acid

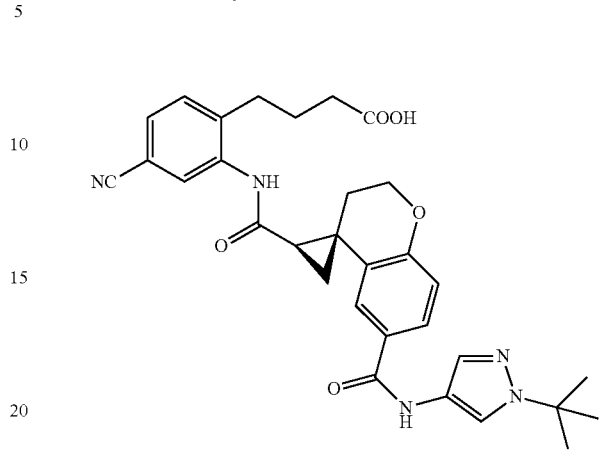

TLC: Rf 0.64 (ethyl acetate);
$^1$H-NMR (CD$_3$OD): δ 1.59, 1.67-1.92, 2.16-2.29, 2.30-2.41, 2.62-2.78, 4.21-4.32, 4.33-4.46, 6.88, 7.37-7.51, 7.58, 7.65-7.74, 8.03, 8.11.

Example 2-40: 4-[4-Cyano-2-({[(2'R,4S)-6-(tetrahydro-2H-pyran-4-ylcarbamoyl)-2,3-dihydrospiro[chromene-4,1'-cyclopropan]-2'-yl]carbonyl}amino)phenyl]butanoic acid

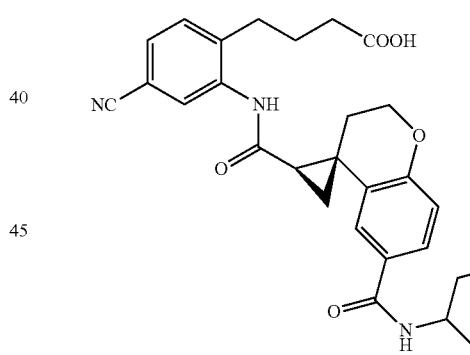

TLC: Rf 0.62 (ethyl acetate:methanol=9:1);
$^1$H-NMR (DMSO-$d_6$): δ 1.44-1.86, 2.02-2.24, 2.59-2.70, 3.35-3.44, 3.80-4.15, 4.25-4.37, 6.84, 7.37-7.46, 7.57, 7.64, 7.87, 8.13, 9.90, 12.09.

Example 2-41: 4-[4-Cyano-2-({[(2'R,4S)-6-(1,2-oxazol-5-ylcarbamoyl)-2,3-dihydrospiro[chromene-4,1'-cyclopropan]-2'-yl]carbonyl}amino)phenyl]butanoic acid TLC: Rf 0.71 (ethyl acetate:methanol=9:1);
$^1$H-NMR (DMSO-$d_6$): δ 1.56-1.66, 1.73, 1.87, 2.06-2.25, 2.60-2.70, 4.06-4.19, 4.31-4.44, 6.39, 6.94, 7.41, 7.57, 7.67, 7.81, 7.87, 8.50, 9.92, 11.90, 12.09.

Example 2-42: 4-[4-Cyano-2-({[(2'R,4S)-6-(4-pyridinylcarbamoyl)-2,3-dihydrospiro[chromene-4,1'-cyclopropan]-2'-yl]carbonyl}amino)phenyl]butanoic acid TLC: Rf 0.53 (dichloromethane:methanol=4:1);
$^1$H-NMR (DMSO-d$_6$): δ 1.57-1.66, 1.73, 1.83, 2.09-2.24, 2.60-2.70, 4.08-4.21, 4.31-4.42, 6.95, 7.41, 7.52-7.61, 7.74-7.91, 8.42-8.52, 9.91, 10.38, 12.09.

Example 2-43: 4-{4-Cyano-2-[({(2'R,4S)-6-[(1-methyl-1H-pyrazol-5-yl)carbamoyl]-2, 3-dihydrospiro[chromene-4,1'-cyclopropan]-2'-yl}carbonyl)amino]phenyl}butanoic acid TLC: Rf 0.58 (chloroform:methanol=9:1);
$^1$H-NMR (DMSO-d$_6$): δ 1.55-1.65, 1.66-1.90, 2.06-2.29, 2.50, 2.60-2.74, 3.66, 4.06-4.22, 4.30-4.46, 6.17, 6.93, 7.35-7.45, 7.52-7.61, 7.77, 7.88, 9.91, 10.15, 12.10.

Example 2-44: 4-[4-Cyano-2-({[(2'R,4S)-6-(propylcarbamoyl)-2,3-dihydrospiro[chromene-4,1'-cyclopropan]-2'-yl]carbonyl}amino)phenyl]butanoic acid

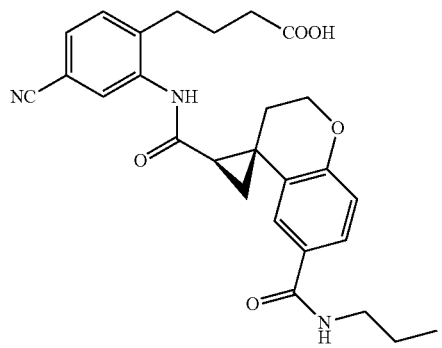 [SMILES: CCCNC(=O)c1ccc2c(c1)[C@]1(CCO2)C[C@H]1C(=O)Nc1cc(C#N)ccc1CCCC(=O)O]

TLC: Rf 0.75 (ethyl acetate);
$^1$H-NMR (DMSO-d$_6$): δ 0.88, 1.45-1.63, 1.68-1.82, 2.07-2.25, 2.45, 2.61-2.72, 3.15-3.26, 4.10, 4.32, 6.85, 7.39-7.46, 7.57-7.63, 7.88, 8.32, 9.90, 12.11.

Example 2-45: 4-{4-Cyano-2-[({(2'R,4S)-6-[(2-ethoxyethyl)carbamoyl]-2,3-dihydrospiro[chromene-4,1'-cycopropan]-2'-yl}carbonyl)amino]phenyl}butanoic acid

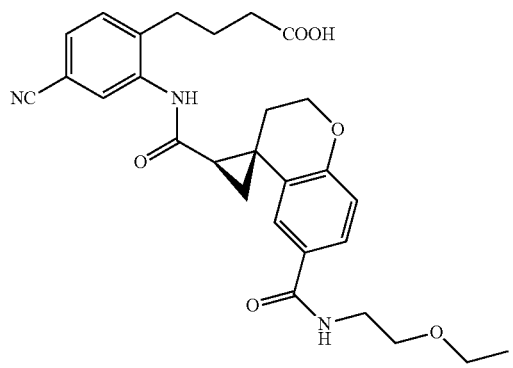 [SMILES: CCOCCNC(=O)c1ccc2c(c1)[C@]1(CCO2)C[C@H]1C(=O)Nc1cc(C#N)ccc1CCCC(=O)O]

TLC: Rf 0.51 (ethyl acetate);
$^1$H-NMR (DMSO-d$_6$): δ 1.11, 1.59, 1.67-1.83, 2.07-2.26, 2.47, 2.61-2.71, 3.35-3.52, 4.10, 4.33, 6.85, 7.38-7.48, 7.57-7.64, 7.88, 8.42, 9.90, 12.09.

Example 2-46: 4-[4-Cyano-2-({[(2'R,4S)-6-(ethylcarbamoyl)-2,3-dihydrospiro[chromene-4,1'-cyclopropan]-2'-yl]carbonyl}amino)phenyl]butanoic acid

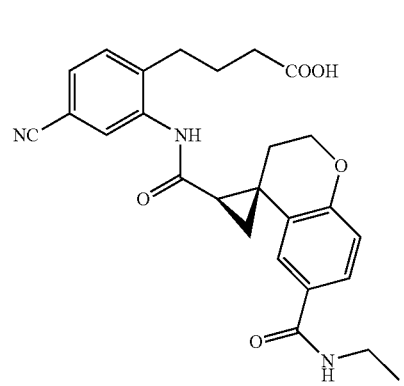

TLC: Rf 0.59 (ethyl acetate);
$^1$H-NMR (DMSO-d$_6$): δ 1.10, 1.58, 1.65-1.80, 2.07-2.24, 2.45, 2.58-2.69, 3.19-3.33, 4.09, 4.32, 6.84, 7.37-7.45, 7.57, 7.62, 7.88, 8.33, 9.89, 12.09.

Example 2-47: 4-{4-Cyano-2-[({(2'R,4S)-6-[(1-methoxy-2-methyl-2-propanyl)carbamoyl]-2, 3-dihydrospiro[chromene-4,1'-cyclopropan]-2'-yl}carbonyl)amino]phenyl}butanoic acid TLC: Rf 0.72 (hexane:ethyl acetate=1:3);
$^1$H-NMR (DMSO-d$_6$): δ 1.33, 1.57, 1.67-1.86, 2.08-2.25, 2.47, 2.62-2.71, 3.27, 3.53, 4.09, 4.32, 6.82, 7.35-7.45, 7.48, 7.57-7.62, 7.88, 9.89, 12.10.

Reference Example 13: Ethyl 4-[4-cyano-2-({[(2'R,4S)-6-(5-methyl-1,3,4-oxadiazol-2-yl)-2,3-dihydrospiro[chromene-4,1'-cyclopropan]-2'-yl]carbonyl}amino)phenyl]butanoate

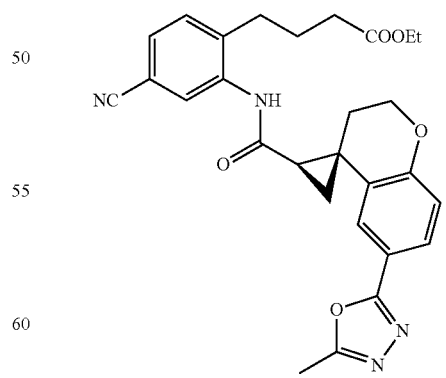

Triethylamine (60 μL), and T3P (a 1.7 mol/L ethyl acetate solution, 95 μL) were added at room temperature to a 0.5-mL dichloromethane solution of the compound (50 mg) produced in Reference Example 11, and acetylhydrazine (16 mg). The reaction mixture was stirred at room temperature for 1.5 h, and concentrated under reduced pressure. The Burgess reagent (methyl N-(triethylammoniosulfonyl)carbamate, 117 mg) was added at room temperature to a 5-mL THF solution of the compound obtained by purifying the resulting residue by silica gel column chromatography (Yamazen Autopurification Device). The mixture was stirred at 100° C. for 1 h using a microwave reactor (Biotage, Ltd.). A saturated sodium bicarbonate aqueous solution was poured into the reaction mixture, and the mixture was extracted with ethyl acetate. The organic layer was washed with saturated brine, dried over anhydrous magnesium sulfate, and concentrated under reduced pressure. The resulting residue was then purified by silica gel column chromatography (Yamazen Autopurification Device) to obtain the title compound (22 mg) having the following physical property values.

TLC: Rf 0.53 (hexane:ethyl acetate=1:3);

$^1$H-NMR (CDCl$_3$): δ 0.94, 1.65-1.93, 1.89, 2.26-2.34, 2.35-2.44, 2.56-2.63, 2.66-2.76, 3.12-3.28, 3.36-3.55, 3.58-3.74, 4.07-4.23, 4.30-4.41, 6.92, 7.18, 1.28, 7.54, 7.70, 8.72, 9.39.

Example 3: 4-[4-Cyano-2-({[(2'R,4S)-6-(5-methyl-1,3,4-oxadiazol-2-yl)-2,3-dihydrospiro[chromene-4,1'-cyclopropan]-2'-yl]carbonyl}amino)phenyl]butanoic acid

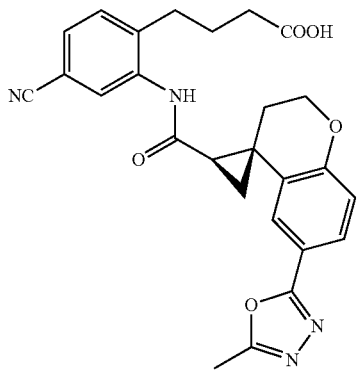 [SMILES: Cc1nnc(-c2ccc3c(c2)[C@]2(CCO3)C[C@H]2C(=O)Nc2cc(C#N)ccc2CCCC(=O)O)o1]

The present compound having the following physical property values was obtained by performing the procedures of Example 1 using the compound produced in Reference Example 13, instead of the compound produced in Reference Example 12.

TLC: Rf 0.93 (dichloromethane:methanol=9:1);

$^1$H-NMR (CDCl$_3$): δ 1.27, 1.54, 1.70-1.91, 2.17, 2.32, 2.45-2.90, 3.64, 4.35-4.48, 4.56-4.66, 6.92, 7.20, 7.28, 7.58, 8.15, 8.92, 9.91, 12.68.

Example 4

The present compounds having the following physical property values were obtained by performing the same procedures from Reference Example 13 to Example 1, except that the acetylhydrazine was replaced with a corresponding hydrazine compound.

Example 4-1: 4-[4-Cyano-2-({[(2'R,4S)-6-(5-cyclopropyl-1,3,4-oxadiazol-2-yl)-2,3-dihydrospiro[chromene-4,1'-cyclopropan]-2'-yl]carbonyl}amino)phenyl]butanoic acid

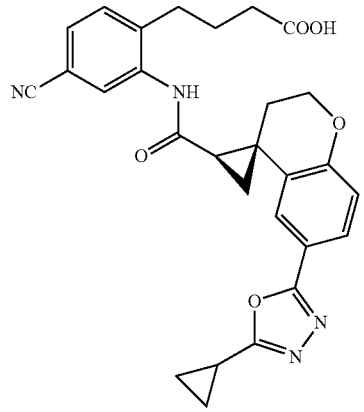 [SMILES: N#Cc1ccc(CCCC(=O)O)c(NC(=O)[C@@H]2C[C@]23CCOc2ccc(-c4nnc(C5CC5)o4)cc23)c1]

TLC: Rf 0.64 (ethyl acetate:methanol=19:1);

$^1$H-NMR (CDCl$_3$): δ 1.14-1.32, 1.78, 2.07-2.41, 2.43-2.91, 3.63, 4.33-4.49, 4.61, 6.86-6.96, 7.16-7.32, 7.54, 8.13, 8.92, 9.91.

Example 4-2: 4-{4-Cyano-2-[({(2'R,4S)-6-[5-(2-methyl-2-propanyl)-1,3,4-oxadiazol-2-yl]-2, 3-dihydrospiro[chromene-4,1'-cyclopropan]-2'-yl}carbonyl)amino]phenyl}butanoic acid TLC: Rf 0.83 (ethyl acetate:methanol=19:1);

$^1$H-NMR (CDCl$_3$): δ 1.19-1.32, 1.44-1.52, 1.64-1.87, 2.10-2.40, 2.44-2.90, 3.64, 4.35-4.49, 4.56-4.67, 6.93, 7.16-7.35, 7.60, 8.15, 8.92, 9.92.

Example 4-3: 4-[4-Cyano-2-({[(2'R,4S)-6-(5-ethyl-1,3,4-oxadiazol-2-yl)-2,3-dihydrospiro[chromene-4,1'-cyclopropan]-2'-yl]carbonyl}amino)phenyl]butanoic acid TLC: Rf 0.53 (dichloromethane:methanol=9:1);

$^1$H-NMR (DMSO-d$_6$): δ1.32, 1.60, 1.66-1.82, 2.10-2.24, 2.60-2.70, 2.92, 4.09-4.21, 4.31-4.42, 6.99, 7.41, 7.46, 7.57, 7.71, 7.88, 9.91, 12.08.

Reference Example 14: Ethyl 4-[4-cyano-2-({[(2'R,4S)-6-(3-methyl-1,2,4-oxadiazol-5-yl)-2, 3-dihydrospiro[chromene-4,1'-cyclopropan]-2'-yl]carbonyl}amino)phenyl]butanoate

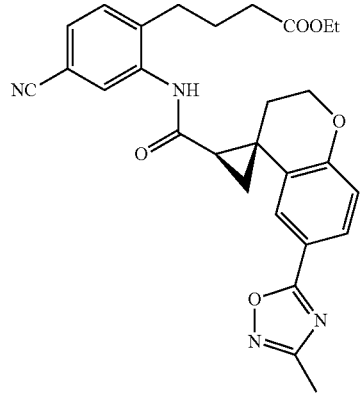 [SMILES: CCOC(=O)CCCc1ccc(C#N)cc1NC(=O)[C@@H]1C[C@]12CCOc1ccc(-c3nc(C)no3)cc12]

Triethylamine (0.144 mL), and T3P (a 1.7 mol/L ethyl acetate solution, 0.380 mL) were added at room temperature to a 0.5-mL ethyl acetate solution of the compound (80 mg) produced in Reference Example 11, and acetamideoxime (32 mg). The reaction mixture was heated under reflux for 4 days, and concentrated under reduced pressure. The resulting residue was then purified by silica gel column chromatography (Yamazen Autopurification Device) to obtain the title compound (49 mg) having the following physical property values.

TLC: Rf 0.55 (hexane:ethyl acetate=1:1);

$^1$H-NMR (CDCl$_3$): δ 0.92, 1.64-1.83, 1.86-1.95, 2.22-2.35, 2.36-2.44, 2.45, 2.54-2.65, 2.72, 3.39-3.54, 3.59-3.73, 4.10-4.23, 4.32-4.44, 6.94, 7.20, 7.28, 7.59, 7.84, 8.74, 9.39.

Example 5: 4-[4-Cyano-2-({[(2'R,4S)-6-(3-methyl-1,2,4-oxadiazol-5-yl)-2,3-dihydrospiro[chromene-4,1'-cyclopropan]-2'-yl]carbonyl}amino)phenyl]butanoic acid

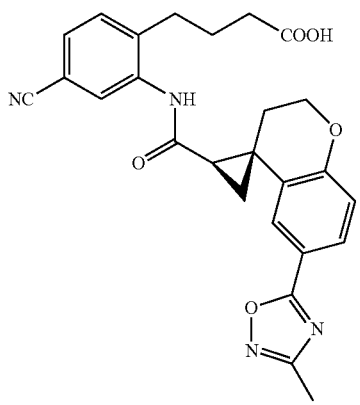 [SMILES: Cc1noc(-c2ccc3c(c2)[C@]2(CCO3)C[C@H]2C(=O)Nc2cc(C#N)ccc2CCCC(=O)O)n1]

The present compound having the following physical property values was obtained by performing the procedures of Example 1 using the compound produced in Reference Example 14, instead of the compound produced in Reference Example 12.

TLC: Rf 0.74 (ethyl acetate:methanol=20:1);

$^1$H-NMR (DMSO-d$_6$): δ 1.55-1.64, 1.67-1.83, 2.11-2.29, 2.39, 2.51-2.60, 2.61-2.73, 4.11-4.25, 4.31-4.44, 7.02, 7.41, 7.52-7.62, 7.83, 7.88, 9.90, 12.10.

Reference Example 15: Ethyl 4-[4-cyano-2-({[(2'R,4S)-6-(4-fluorophenyl)-2,3-dihydrospiro[chromene-4,1'-cyclopropan]-2'-yl]carbonyl}amino)phenyl]butanoate

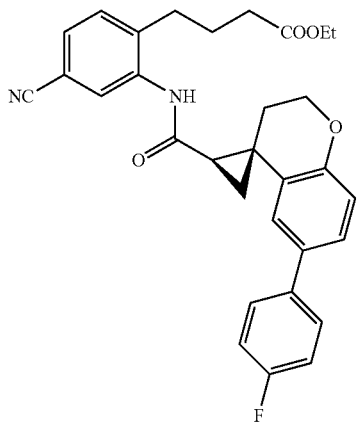 [SMILES: CCOC(=O)CCCc1ccc(C#N)cc1NC(=O)[C@@H]1C[C@]12CCOc1ccc(-c3ccc(F)cc3)cc12]

Cesium carbonate (84 mg), 4-fluorophenylboronic acid (36 mg), and purified water (0.4 mL) were added at room temperature to a 0.4-mL 1,2-dimethoxyethane solution of the compound (70 mg) produced in Reference Example 10. After replacing the atmosphere with argon, a [1,1'-bis(diphenylphosphino)ferrocene]palladium(II) dichloride dichloromethane complex (5 mg) was added, and the mixture was stirred overnight at 85° C. The reaction mixture was diluted with ethyl acetate, and extracted with ethyl acetate after adding water. The organic layer was washed with water and saturated brine, dried over anhydrous sodium sulfate, and concentrated under reduced pressure. The resulting residue was then purified by silica gel column chromatography (Yamazen Autopurification Device) to obtain the title compound (54 mg) having the following physical property values.

TLC: Rf 0.48 (hexane:ethyl acetate=2:1);

$^1$H-NMR (CDCl$_3$): δ 0.83, 1.64-1.79, 1.82-1.93, 2.29, 2.33-2.43, 2.48-2.74, 3.30, 3.49, 4.06-4.19, 4.26-4.38, 6.84-6.91, 6.97, 7.04-7.15, 7.15-7.22, 7.22-7.32, 7.39-7.51, 8.73, 9.30.

Example 6: 4-[4-Cyano-2-({[(2'R,4S)-6-(4-fluorophenyl)-2,3-dihydrospiro[chromene-4,1'-cyclopropan]-2'-yl]carbonyl}amino)phenyl]butanoic acid

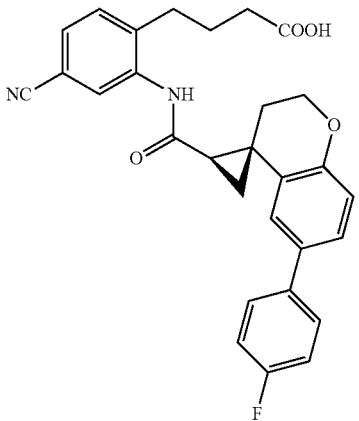 [SMILES: N#Cc1ccc(CCCC(=O)O)c(NC(=O)[C@@H]2C[C@]23CCOc2ccc(-c4ccc(F)cc4)cc23)c1]

The present compound having the following physical property values was obtained by performing the procedures of Example 1 using the compound produced in Reference Example 15, instead of the compound produced in Reference Example 12.

TLC: Rf 0.58 (dichloromethane:methanol=9:1);

$^1$H-NMR (DMSO-d$_6$): δ1.50-1.60, 1.72, 1.87, 2.06-2.24, 2.60-2.69, 4.03-4.15, 4.24-4.35, 6.87, 7.11, 7.19-7.29, 7.32-7.44, 7.56, 7.61-7.70, 7.87, 9.88, 12.09.

Example 7

The present compounds having the following physical property values were obtained by performing the same procedures from Reference Example 15 to Example 1, except that the 4-fluorophenylboronic acid was replaced with a corresponding boronic acid compound, or a corresponding heterocyclic ring.

Example 7-1: 4-[4-Cyano-2-({[(2'R,4S)-6-phenyl-2,3-dihydrospiro[chromene-4,1'-cyclopropan]-2'-yl]carbonyl}amino)phenyl]butanoic acid TLC: Rf 0.53 (dichloromethane:methanol=9:1)
$^1$H-NMR (CDCl$_3$): δ 1.58-1.81, 2.14-2.27, 2.36-2.46, 2.49-2.71, 2.78, 4.22-4.37, 6.92, 7.15, 7.16-7.22, 7.26-7.51, 7.52-7.61, 8.69, 8.95.

Example 7-2: 4-[4-Cyano-2-({[(2'R,4S)-6-(4-pyridinyl)-2,3-dihydrospiro[chromene-4,1'-cyclopropan]-2'-yl]carbonyl}amino)phenyl]butanoic acid TLC: Rf 0.36 (dichloromethane:methanol=9:1);
$^1$H-NMR (DMSO-d$_6$): δ 1.52-1.63, 1.64-1.79, 1.87-1.99, 2.08-2.30, 2.43-2.73, 3.99-4.20, 4.25-4.41, 6.93, 7.31, 7.40, 7.56, 7.66-7.71, 7.87, 8.51-8.62, 9.88, 11.90-12.18.

Example 7-3: 4-[4-Cyano-2-({[(2'R,4S)-6-(3-pyridinyl)-2,3-dihydrospiro[chromene-4,1'-cyclopropan]-2'-yl]carbonyl}amino)phenyl]butanoic acid

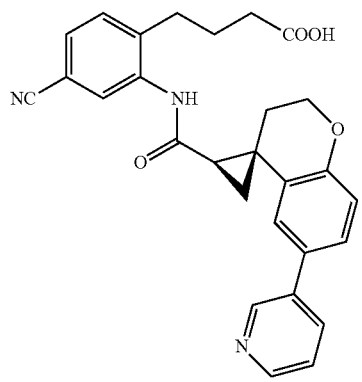 [SMILES: N#Cc1ccc(CCCC(=O)O)c(NC(=O)[C@@H]2C[C@]23CCOc2ccc(-c4cccnc4)cc23)c1]

TLC: Rf 0.36 (dichloromethane:methanol=9:1);
$^1$H-NMR (DMSO-d$_6$): δ 1.56, 1.65-1.77, 1.88-2.00, 2.06-2.30, 2.34-2.75, 4.03-4.19, 4.25-4.39, 6.92, 7.22, 7.37-7.51, 7.57, 7.87, 7.99-8.09, 8.48-8.53, 8.87, 9.87.

Example 7-4: 4-[4-Cyano-2-({[(2'R,4S)-6-(1H-pyrazol-1-yl)-2,3-dihydrospiro[chromene-4,1'-cyclopropan]-2'-yl]carbonyl}amino)phenyl]butanoic acid

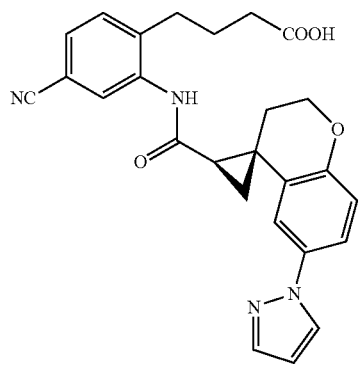 [SMILES: N#Cc1ccc(CCCC(=O)O)c(NC(=O)[C@@H]2C[C@]23CCOc2ccc(-n4cccn4)cc23)c1]

TLC: Rf 0.45 (dichloromethane:methanol=9:1);
$^1$H-NMR (CDCl$_3$): δ 1.23-1.34, 1.62, 1.66-1.83, 2.05-2.23, 2.40-2.59, 2.61-2.82, 3.37-3.47, 4.22-4.35, 4.44-4.52, 6.49, 6.88, 7.11, 7.20, 7.28, 7.41, 7.71, 8.86, 9.95.

Example 7-5: 4-[4-Cyano-2-({[(2'R,4S)-6-(1H-pyrazol-5-yl)-2,3-dihydrospiro[chromene-4,1'-cyclopropan]-2'-yl]carbonyl}amino)phenyl]butanoic acid

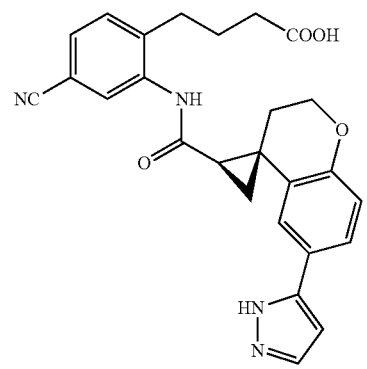 [SMILES: N#Cc1ccc(CCCC(=O)O)c(NC(=O)[C@@H]2C[C@]23CCOc2ccc(-c4ccn[nH]4)cc23)c1]

TLC: Rf 0.35 (dichloromethane:methanol=9:1);
$^1$H-NMR (DMSO-d$_6$): δ 1.51-1.62, 1.63-1.86, 2.04-2.33, 2.34-2.75, 3.98-4.14, 4.23-4.35, 6.65, 6.82, 7.29, 7.40, 7.48-7.60, 7.63, 7.87, 9.91, 12.47.

Example 7-6: 4-[4-Cyano-2-({[(2'R,4S)-6-(4-pyridazinyl)-2,3-dihydrospiro[chromene-4,1'-cyclopropan]-2'-yl]carbonyl}amino)phenyl]butanoic acid

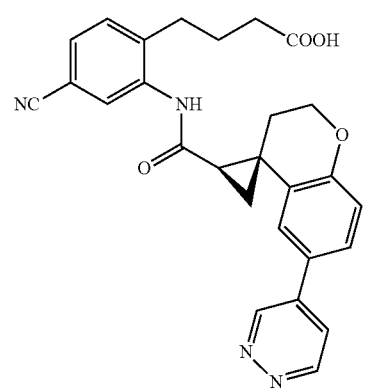 [SMILES: N#Cc1ccc(CCCC(=O)O)c(NC(=O)[C@@H]2C[C@]23CCOc2ccc(-c4ccnnc4)cc23)c1]

TLC: Rf 0.40 (dichloromethane:methanol=9:1);
$^1$H-NMR (DMSO-d$_6$): δ 1.53-1.62, 1.63-1.80, 1.95-2.06, 2.09-2.33, 2.34-2.78, 4.01-4.22, 4.28-4.42, 6.97, 7.42, 7.47, 7.57, 7.71, 7.87, 7.94-8.04, 9.20, 9.60, 9.87, 12.1.

Example 7-7: 4-[4-Cyano-2-({[(2'R,4S)-6-(1-methyl-1H-pyrazol-4-yl)-2,3-dihydrospiro[chromene-4,1'-cyclopropan]-2'-yl]carbonyl}amino)phenyl]butanoic acid TLC: Rf 0.25 (ethyl acetate:methanol=19:1);
$^1$H-NMR (CDCl$_3$): δ 1.44-1.88, 2.22-2.33, 2.48, 2.58-2.76, 3.70, 4.16-4.36, 6.81-6.95, 7.11-7.34, 7.39, 7.56, 8.73, 9.16.

Example 7-8: 4-[4-Cyano-2-(([(2'R,4S)-6-(5-pyrimidinyl)-2,3-dihydrospiro[chromene-4, 1'-cyclopropan]-2'-yl]carbonyl amino)phenyl]butanoic acid TLC: Rf 0.44 (dichloromethane:methanol=9:1);
$^1$H-NMR (DMSO-d$_6$): δ 1.57, 1.65-1.79, 1.92-2.03, 2.06-2.35, 2.36-2.77, 4.01-4.17, 4.27-4.40, 6.94, 7.33, 7.40, 7.50-7.61, 7.87, 9.12, 9.86, 12.08.

Example 7-9: 4-[4-Cyano-2-({[(2'R,4S)-6-(2-thienyl)-2,3-dihydrospiro[chromene-4,1'-cyclopropan]-2'-yl]carbonyl}amino)phenyl]butanoic acid TLC: Rf 0.44 (dichloromethane:methanol=9:1);
$^1$H-NMR (DMSO-d): δ 1.51-1.61, 1.65-1.78, 1.79-1.88, 2.05-2.31, 2.40-2.76, 3.98-4.14, 4.23-4.36, 6.83, 7.04-7.16, 7.30-7.49, 7.57, 7.86, 9.90, 12.08.

Example 7-10: 4-[4-Cyano-2-({[(2'R,4S)-6-(2-oxo-1-pyrrolidinyl)-2,3-dihydrospiro[chromene-4,1'-cyclopropan]-2'-yl]carbonyl}amino)phenyl]butanoic acid

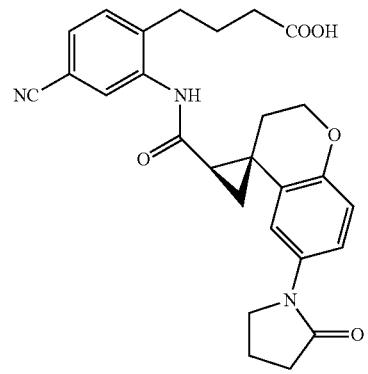 [SMILES: N#Cc1ccc(CCCC(=O)O)c(NC(=O)[C@@H]2C[C@]23CCOc2ccc(N4CCCC4=O)cc23)c1]

TLC: Rf 0.47 (dichloromethane:methanol=9:1);
$^1$H-NMR (DMSO-d$_6$): δ 1.50-1.59, 1.60-1.80, 1.93-2.12, 2.19, 2.31-2.51, 2.54-2.78, 3.78, 3.93-4.09, 4.19-4.31, 6.78, 7.09, 7.29, 7.40, 7.56, 7.85, 9.91, 12.08.

Example 7-11: 4-[4-Cyano-2-({[(2'R,4S)-6-(1,3-thiazol-5-yl)-2,3-dihydrospiro[chromene-4,1'-cyclopropan]-2'-yl]carbonyl}amino)phenyl]butanoic acid TLC: Rf 0.53 (ethyl acetate:methanol=20:1);
$^1$H-NMR (CDCl$_3$): δ 1.20-1.30, 1.58, 1.73-1.90, 2.26-2.37, 2.52, 2.64-2.82, 4.19-4.41, 6.81-6.97, 7.13-7.35, 7.77, 8.60, 8.69, 9.25.

Example 7-12: 4-[4-Cyano-2-({[(2'R,4S)-6-(pyrazolo[1,5-a]pyridin-3-yl)-2,3-dihydrospiro[chromene-4,1'-cyclopropan]-2'-yl]carbonyl}amino)phenyl]butanoic acid TLC: Rf 0.40 (dichloromethane:methanol=9:1);
$^1$H-NMR (CDCl$_3$): δ 1.59-1.70, 1.76-1.84, 2.31, 2.43-2.53, 2.60-2.80, 4.15-4.44, 6.72, 6.89, 6.97, 7.09-7.36, 7.68, 7.89, 8.43, 8.70, 9.15.

Example 7-13: 4-[4-Cyano-2-({[(2'R,4S)-6-(6-methoxy-3-pyridinyl)-2,3-dihydrospiro[chromene-4, 1'-cyclopropan]-2'-yl]carbonyl}amino)phenyl]butanoic acid

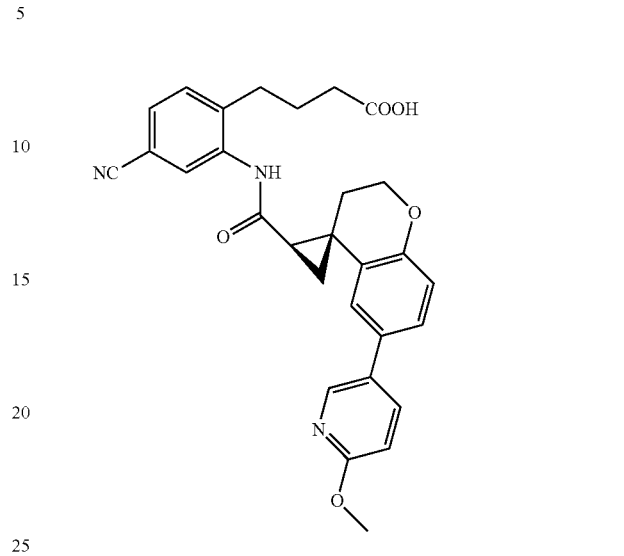

TLC: Rf 0.56 (ethyl acetate);
$^1$H-NMR (CD$_3$OD): δ 1.65-1.93, 2.14-2.29, 2.33, 2.58, 2.67-2.78, 3.92, 4.21, 4.32, 6.80-6.91, 7.06, 7.30, 7.42, 7.48, 7.84-7.95, 8.31.

Example 7-14: 4-{4-Cyano-2-[({(2'R,4S)-6-[6-(1H-pyrazol-1-yl)-3-pyridinyl]-2,3-dihydrospiro[chromene-4,1'-cyclopropan]-2'-yl}carbonyl)amino]phenyl}butanoic acid

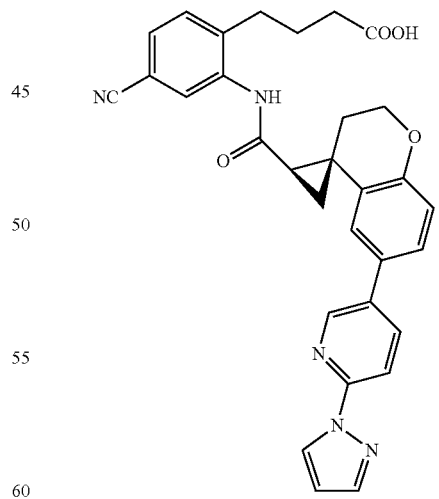

TLC: Rf 0.60 (chloroform:methanol=9:1);
$^1$H-NMR (DMSO-d$_6$): δ 1.57, 1.63-1.79, 1.89-2.01, 2.08-2.25, 2.50-2.56, 2.60-2.72, 4.03-4.18, 4.27-4.40, 6.59, 6.93, 7.27, 7.40, 7.47-7.60, 7.80-7.91, 7.96, 8.27, 8.63, 8.76, 9.88, 12.10.

Example 7-15: 4-{4-Cyano-2-[({(2'R,4S)-6-[6-(dimethylamino)-3-pyridinyl]-2,3-dihydrospiro[chromene-4,1'-cyclopropan]-2'-yl}carbonyl)amino]phenyl}butanoic acid

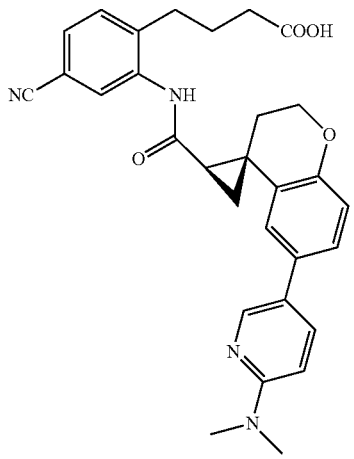 [SMILES: CN(C)c1ccc(-c2ccc3c(c2)[C@]2(CCO3)C[C@H]2C(=O)Nc2cc(C#N)ccc2CCCC(=O)O)cn1]

TLC: Rf 0.58 (chloroform:methanol=9:1);
$^1$H-NMR (DMSO-d$_6$): δ 1.51-1.62, 1.63-1.80, 1.84-1.95, 2.06-2.25, 2.51-2.57, 2.60-2.75, 3.18, 4.02-4.17, 4.23-4.39, 6.88, 7.01-7.21, 7.35-7.47, 7.55, 7.87, 8.10-8.29, 9.92, 12.10.

Example 7-16: 4-[4-Cyano-2-({[(2'R,4S)-6-(6-methyl-3-pyridinyl)-2,3-dihydrospiro[chromene-4,1'-cyclopropan]-2'-yl]carbonyl}amino)phenyl]butanoic acid

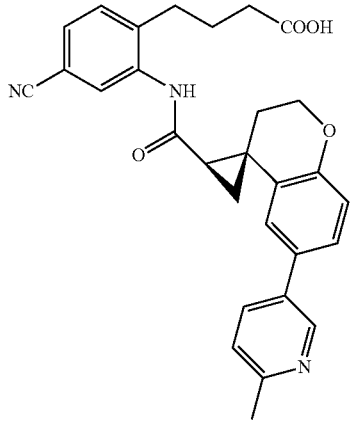 [SMILES: Cc1ccc(-c2ccc3c(c2)[C@]2(CCO3)C[C@H]2C(=O)Nc2cc(C#N)ccc2CCCC(=O)O)cn1]

TLC: Rf 0.63 (dichloromethane:methanol=9:1);
$^1$H-NMR (DMSO-d$_6$): δ 1.46-1.56, 1.56-1.79, 2.03, 2.16, 2.66, 4.15, 4.22-4.33, 6.86, 7.20, 7.27, 7.33-7.44, 7.44-7.52, 8.08-8.21, 8.70, 11.11.

Example 7-17: 4-[4-Cyano-2-({[(2'R,4S)-6-(6-fluoro-3-pyridinyl)-2,3-dihydrospiro[chromene-4,1'-cyclopropan]-2'-yl]carbonyl}amino)phenyl]butanoic acid TLC: Rf 0.59 (dichloromethane:methanol=9:1);
$^1$H-NMR (DMSO-d$_6$): δ 1.52-1.60, 1.65-1.79, 1.93, 2.07-2.23, 2.60-2.70, 4.03-4.15, 4.27-4.37, 6.90, 7.19-7.27, 7.40, 7.45, 1.56, 7.87, 8.25, 8.51, 9.87, 12.09.

Example 7-18: 4-{4-Cyano-2-[({(2'R,4S)-6-[6-(methylsulfonyl)-3-pyridinyl]-2,3-dihydrospiro[chromene-4,1'-cyclopropan]-2'-yl}carbonyl)amino]phenyl}butanoic acid TLC: Rf 0.57 (dichloromethane:methanol=9:1);
$^1$H-NMR (DMSO-d$_6$): δ1.58, 1.72, 1.92-2.01, 2.09-2.24, 2.60-2.70, 4.06-4.17, 4.30-4.40, 6.96, 7.33-7.45, 7.58, 7.88, 8.06, 8.41, 9.09, 9.90, 12.10.

Example 7-19: 4-[4-Cyano-2-({[(2'R,4S)-6-(1H-pyrrolo[2,3-b]pyridin-5-yl)-2,3-dihydrospiro[chromene-4,1'-cyclopropan]-2'-yl]carbonyl}amino)phenyl]butanoic acid TLC: Rf 0.55 (dichloromethane:methanol=9:1);
$^1$H-NMR (DMSO-d$_6$): δ 1.51-1.61, 1.65-1.80, 1.91, 2.09-2.24, 2.60-2.70, 4.09, 4.25-4.36, 6.47, 6.89, 7.18, 7.38-7.45, 7.45-7.50, 7.56, 7.88, 8.17, 8.47, 9.94, 11.65, 12.06.

Example 7-20: 4-[4-Cyano-2-({[(2'R,4S)-6-(4-methyl-3,4-dihydro-2H-pyrido [3,2-b][1,4]oxazin-7-yl)-2,3-dihydrospiro[chromene-4,1'-cyclopropan]-2'-yl]carbonyl}amino)phenyl]butanoic acid TLC: Rf 0.65 (dichloromethane:methanol=9:1);
$^1$H-NMR (DMSO-d$_6$): δ 1.48-1.58, 1.65-1.79, 1.88, 2.06-2.14, 2.19, 2.59-2.70, 3.03, 3.40-3.47, 3.99-4.11, 4.19-4.33, 6.81, 7.03, 7.23, 7.29, 7.40, 7.56, 7.86, 7.95, 9.87, 12.08.

Example 7-21: 4-{4-Cyano-2-[({(2'R,4S)-6-[6-(methylamino)-3-pyridinyl]-2,3-dihydrospiro[chromene-4,1'-cyclopropan]-2'-yl}carbonyl)amino]phenyl}butanoic acid

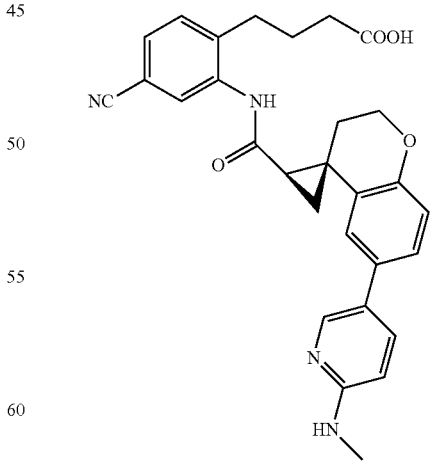

TLC: Rf 0.53 (dichloromethane:methanol=9:1);
$^1$H-NMR (DMSO-d$_6$): δ 1.52-1.61, 1.72, 1.84-1.94, 2.06-2.23, 2.60-2.70, 2.94, 4.02-4.13, 4.25-4.36, 6.88, 6.99, 7.14, 7.34-7.43, 7.56, 7.86, 8.09-8.21, 9.91, 12.13, 13.60.

Example 7-22: 4-{4-Cyano-2-[({(2'R,4S)-6-[3-(2-hydroxy-2-propanyl)phenyl]-2,3-dihydrospiro[chromene-4,1'-cyclopropan]-2'-yl}carbonyl)amino]phenyl}butanoic acid TLC: Rf 0.56 (dichloromethane:methanol=9:1);
$^1$H-NMR (DMSO-d$_6$): δ 1.46, 1.54-1.62, 1.72, 1.79-1.88, 2.07-2.24, 2.60-2.70, 4.02-4.15, 4.25-4.36, 5.05, 6.88, 7.09, 7.29-7.46, 7.57, 7.66, 7.87, 9.90, 12.09.

Example 7-23: 4-[4-Cyano-2-({[(2'R,4S)-6-(2-oxo-1-azetidinyl)-2,3-dihydrospiro[chromene-4,1'-cyclopropan]-2'-yl]carbonyl}amino)phenyl]butanoic acid TLC: Rf 0.47 (dichloromethane:methanol=20:1);
$^1$H-NMR (DMSO-d$_6$): δ 1.54-1.79, 2.02-2.11, 2.19, 2.39-2.68, 3.01-3.05, 3.55-3.61, 3.95-4.03, 4.20-4.29, 6.77-6.81, 7.16, 7.41, 7.56, 7.85, 9.90, 12.10.

Example 7-24: 4-[4-Cyano-2-({[(2'R,4S)-6-(2-oxo-1,3-oxazolidin-3-yl)-2,3-dihydrospiro[chromene-4,1'-cyclopropan]-2'-yl]carbonyl}amino)phenyl]butanoic acid TLC: Rf 0.47 (dichloromethane:methanol=20:1);
$^1$H-NMR (DMSO-d$_6$): δ 1.54-1.79, 2.05-2.24, 2.39-2.68, 3.96-4.06, 4.23-4.31, 4.36-4.45, 6.81, 7.01, 7.27, 7.41, 7.56, 7.86, 9.92, 12.10.

Example 7-25: 4-{4-Cyano-2-[({(2'R,4S)-6-[(4R)-4-hydroxy-2-oxo-1-pyrrolidinyl]-2,3-dihydrospiro[chromene-4,1'-cyclopropan]-2'-yl}carbonyl)amino]phenyl}butanoic acid TLC: Rf 0.40 (dichloromethane:methanol=20:1);
$^1$H-NMR (DMSO-d$_6$): δ 1.53-1.80, 2.06-2.13, 2.19, 2.37-2.81, 3.47-3.55, 4.00-4.08, 4.20-4.39, 5.29-5.37, 6.78, 7.14, 7.25, 7.40, 7.55, 7.87, 9.91, 12.10.

Example 7-26: 4-{4-Cyano-2-[({(2'R,4S)-6-[4-(methylsulfonyl)phenyl]-2,3-dihydrospiro[chromene-4,1'-cyclopropan]-2'-yl}carbonyl)amino]phenyl}butanoic acid TLC: Rf 0.49 (dichloromethane:methanol=9:1);
$^1$H-NMR (DMSO-d$_6$): δ 1.58, 1.72, 1.92, 2.08-2.24, 2.60-2.70, 3.23, 4.05-4.17, 4.27-4.39, 6.93, 7.25, 7.41, 7.50, 7.57, 7.84-7.99, 9.88, 12.09.

Example 7-27: 4-[4-Cyano-2-({[(2'R,4S)-6-(4-cyanophenyl)-2,3-dihydrospiro[chromene-4,1'-cyclopropan]-2'-yl]carbonyl}amino)phenyl]butanoic acid TLC: Rf 0.58 (dichloromethane:methanol=9:1);
$^1$H-NMR (DMSO-d$_6$): δ 1.56, 1.72, 1.93, 2.08-2.24, 2.59-2.69, 4.04-4.16, 4.27-4.38, 6.92, 7.25, 7.40, 7.51, 7.56, 7.87, 9.86, 12.08.

Example 7-28: 4-[4-Cyano-2-({[(2'R, 4S)-6-(1-methyl-1H-pyrazol-5-yl)-2, 3-dihydrospiro[chromene-4,1'-cyclopropan]-2'-yl]carbonyl}amino)phenyl]butanoic acid TLC: Rf 0.59 (chloroform:methanol=9:1);
$^1$H-NMR (DMSO-d$_6$): δ 1.51-1.61, 1.64-1.88, 2.08-2.28, 2.39-2.46, 2.58-2.71, 3.82, 4.05-4.17, 4.27-4.39, 6.32, 6.90, 7.00, 7.25, 7.37-7.45, 7.55, 7.86, 9.89, 12.10.

Reference Example 16: Ethyl 4-{4-cyano-2-[({(2'R, 4S)-6-[1-(tetrahydro-2H-pyran-2-yl)-1H-pyrazol-4-yl]-2, 3-dihydrospiro[chromene-4, 1'-cyclopropan]-2'-yl}carbonyl)amino]phenyl}butanoate

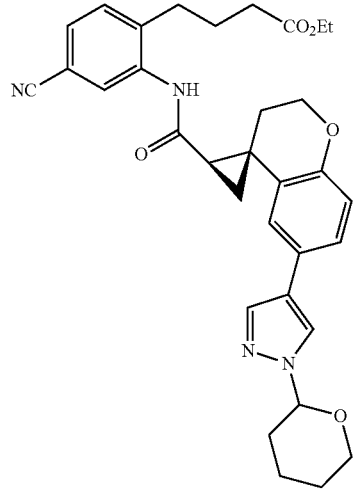 [SMILES: CCOC(=O)CCCc1ccc(C#N)cc1NC(=O)[C@@H]1C[C@]12CCOc1ccc(-c3cnn(C4CCCCO4)c3)cc12]

The title compound having the following physical property values was obtained by performing the procedures of Reference Example 15 using a 1-(2-tetrahydropyranyl)-1H-pyrazole-4-boronic acid pinacol ester, instead of 4-fluorophenylboronic acid.

TLC: Rf 0.62 (hexane:ethyl acetate=1:2);
$^1$H-NMR (CDCl$_3$): δ 0.86, 1.64-1.79, 1.82-1.90, 2.02-2.16, 2.21-2.29, 2.34-2.43, 2.52-2.72, 3.28-3.42, 3.45-3.60, 3.65-3.80, 4.03-4.16, 4.25-4.40, 5.35-5.45, 6.81, 6.90, 7.13-7.23, 7.28, 7.71, 7.76, 8.74, 9.36.

Example 8: 4-[4-Cyano-2-({[(2'R,4S)-6-(1H-pyrazol-4-yl)-2,3-dihydrospiro[chromene-4,1'-cyclopropan]-2'-yl]carbonyl}amino)phenyl]butanoic acid

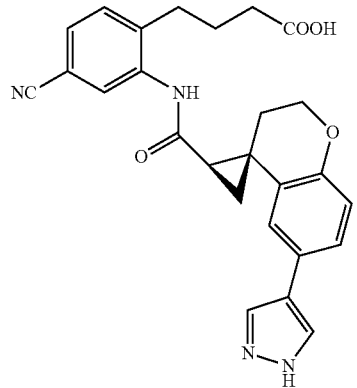 [SMILES: N#Cc1ccc(CCCC(=O)O)c(NC(=O)[C@@H]2C[C@]23CCOc2ccc(-c4cn[nH]c4)cc23)c1]

A hydrochloric acid 1,4-dioxane solution (4 mol/L, 0.1 mL) was added at room temperature to a 1-mL 1, 4-dioxane solution of the compound (30 mg) produced in Reference Example 16. The reaction mixture was stirred at 60° C. for 3 h. After concentrating the reaction mixture under reduced pressure, the procedures of Example 1 was performed to obtain the present compound having the following physical property values.

TLC: Rf 0.40 (ethyl acetate:methanol=20:1);
$^1$H-NMR (DMSO-d$_6$): δ 1.55, 1.64-1.79, 1.81-1.92, 2.04-2.27, 2.35-2.47, 2.52-2.74, 4.02, 4.27, 6.76, 7.09, 7.32, 7.40, 7.56, 7.85, 7.99, 9.89.

Reference Example 17: Ethyl 4-[4-cyano-2-({[(2'R,4S)-6-(4,4,5,5-tetramethyl-1,3,2-dioxabororan-2-yl)-2,3-dihydrospiro[chromene-4,1'-cyclopropan]-2'-yl]carbonyl}amino)phenyl]butanoate

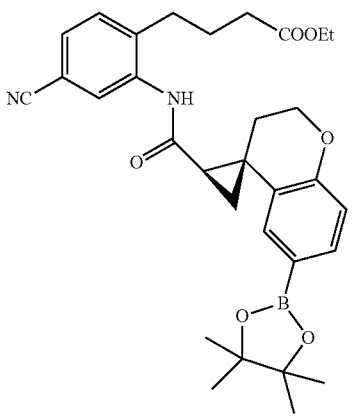 [SMILES: CCOC(=O)CCCc1ccc(C#N)cc1NC(=O)[C@@H]1C[C@]12CCOc1ccc(B3OC(C)(C)C(C)(C)O3)cc12]

While replacing the atmosphere with argon, potassium acetate (1.44 g), bis(pinacolato)diboron (2.43 g), and a [1,1'-bis(diphenylphosphino)ferrocene]palladium(II) dichloride dichloromethane complex (300 mg) were added to a 40-mL dimethyl sulfoxide solution of the compound (4.00 g) produced in Reference Example 10, and the mixture was stirred at 90° C. for 4 h. After diluting the reaction mixture with ethyl acetate, water was added, and the mixture was extracted with ethyl acetate. The organic layer was washed with water and saturated brine, dried over anhydrous sodium sulfate, and concentrated under reduced pressure. The resulting residue was then purified by silica gel column chromatography (Yamazen Autopurification Device) to obtain the title compound (3.54 g) having the following physical property values.

TLC: Rf 0.37 (hexane:ethyl acetate=2:1);
$^1$H-NMR (CDCl$_3$): δ 1.01, 1.20-1.29, 1.31, 1.63-1.77, 1.84, 2.18-2.27, 2.33-2.42, 2.53-2.60, 3.20-3.34, 3.45-3.60, 4.00-4.10, 4.25-4.37, 6.78, 7.18, 7.28, 7.52, 8.68, 9.37.

Example 9: 4-[4-Cyano-2-({[(2'R,4S)-6-(2-pyridinyl)-2,3-dihydrospiro[chromene-4,1'-cyclopropan]-2'-yl]carbonyl}amino)phenyl]butanoic acid

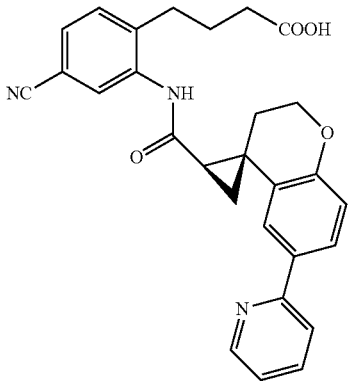 [SMILES: N#Cc1ccc(CCCC(=O)O)c(NC(=O)[C@@H]2C[C@]23CCOc2ccc(-c4ccccn4)cc23)c1]

While replacing the atmosphere with argon, 2-bromopyridine (36 μL), cesium carbonate (120 mg), and a [1,1'-bis(diphenylphosphino)ferrocene]palladium(II) dichloride dichloromethane complex (7.5 mg) were added to a solution of the compound (100 mg) of Reference Example 17 in 1,2-dimethoxyethane (0.3 mL) and water (0.3 mL), and the mixture was stirred at 95° C. for 17 h. The reaction mixture was extracted with ethyl acetate, and the organic layer was washed with water and saturated brine, dried over anhydrous sodium sulfate, and concentrated under reduced pressure. The resulting residue was purified by silica gel column chromatography (Yamazen Autopurification Device) to obtain ethyl 4-[4-cyano-2-({[(2'R,4S)-6-(2-pyridinyl)-2,3-dihydrospiro[chromene-4,1'-cyclopropan]-2'-yl]carbonyl}amino)phenyl]butanoate, and the procedures of Example 1 were performed with this compound to obtain the present compound having the following physical property values.

TLC: Rf 0.44 (dichloromethane:methanol=9:1);
$^1$H-NMR (DMSO-d$_6$): δ 1.54-1.66, 1.68-1.88, 2.07-2.29, 2.54-2.76, 4.04-4.17, 4.26-4.38, 6.89, 7.23-7.33, 7.40, 7.52-7.64, 7.77-7.99, 8.61, 9.90, 12.10.

Example 10

The present compounds having the following physical property values were obtained by performing the same procedures performed in Example 9, except that the 2-bromopyridine was replaced with a corresponding halogen-containing heterocyclic ring.

Example 10-1: 4-[4-Cyano-2-({[(2'R,4S)-6-(2-pyrimidinyl)-2,3-dihydrospiro[chromene-4,1'-cyclopropan]-2'-yl]carbonyl}amino)phenyl]butanoic acid TLC: Rf 0.45 (dichloromethane:methanol=9:1);
$^1$H-NMR (DMSO-d$_6$): δ 1.54-1.83, 2.07-2.28, 2.35-2.77, 4.05-4.22, 4.26-4.42, 6.93, 7.29-7.45, 7.56, 7.88, 7.94, 8.15, 8.84, 9.93, 12.10.

Example 10-2: 4-[4-Cyano-2-({[(2'R,4S)-6-(1,3-thiazol-2-yl)-2,3-dihydrospiro[chromene-4,1'-cyclopropan]-2'-yl]carbonyl}amino)phenyl]butanoic acid

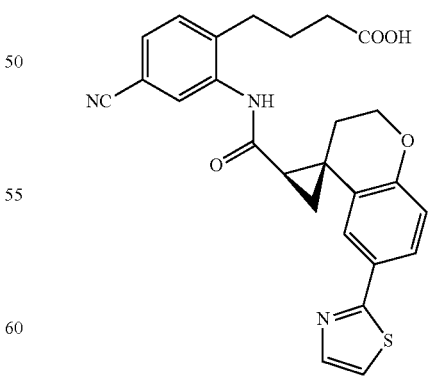

TLC: Rf 0.81 (ethyl acetate:methanol=20:1);
$^1$H-NMR (CDCl$_3$): δ 1.19-1.32, 1.34-1.85, 2.10-2.25, 2.40-2.79, 3.61, 4.35, 4.48-4.62, 6.88, 7.15-7.30, 7.35, 7.38-7.47, 7.68-7.77, 7.85, 8.88, 10.00.

Example 10-3: 4-[4-Cyano-2-({[(2'R,4S)-6-(1,3-oxazol-2-yl)-2,3-dihydrospiro[chromene-4,1'-cyclopropan]-2'-yl]carbonyl}amino)phenyl]butanoic acid

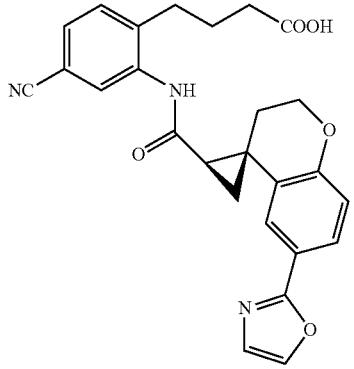 [SMILES: N#Cc1ccc(CCCC(=O)O)c(NC(=O)[C@@H]2C[C@]23CCOc2ccc(-c4ncco4)cc23)c1]

TLC: Rf 0.81 (ethyl acetate:methanol=20:1);
¹H-NMR (CDCl₃): δ 1.18-1.29, 1.53, 1.68-1.86, 2.09-2.33, 2.43-2.87, 3.60, 4.39, 4.52-4.64, 6.90, 7.15, 7.17, 7.28, 7.67, 7.72, 8.05, 8.92, 9.95.

Example 10-4: 4-[4-Cyano-2-({[(2'R,4S)-6-(1-methyl-1H-1,2,3-triazol-4-yl)-2,3-dihydrospiro[chromene-4,1'-cyclopropan]-2'-yl]carbonyl}amino)phenyl]butanoic acid

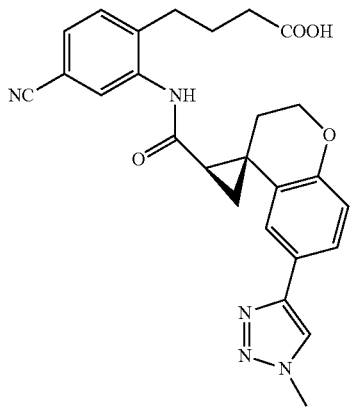 [SMILES: Cn1cc(-c2ccc3c(c2)[C@]2(CCO3)C[C@H]2C(=O)Nc2cc(C#N)ccc2CCCC(=O)O)nn1]

TLC: Rf 0.58 (ethyl acetate:methanol=20:1);
¹H-NMR (CDCl₃): δ 1.21-1.32, 1.56, 1.69-1.86, 2.14-2.31, 2.44-2.88, 3.64, 4.15-4.20, 4.34, 4.53, 6.86, 7.13-7.31, 7.63, 7.68, 7.79, 8.92, 10.01.

Example 10-5: 4-[4-Cyano-2-({[(2'R,4S)-6-(3-pyridazinyl)-2,3-dihydrospiro[chromene-4, 1'-cyclopropan]-2'-yl]carbonyl}amino)phenyl]butanoic acid

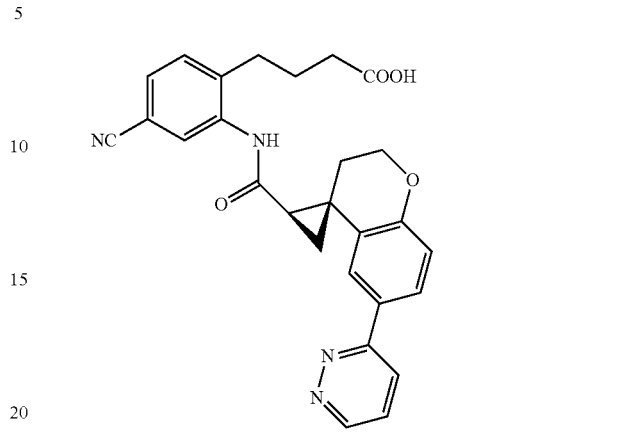

TLC: Rf 0.40 (dichloromethane:methanol=9:1);
¹H-NMR (CDCl₃): δ 1.17-1.31, 1.61, 1.66-1.90, 2.11-2.32, 2.36-2.82, 3.48-3.71, 4.35, 4.54, 6.98, 7.21, 7.28, 7.36, 7.66, 7.83, 7.80-7.83, 8.87, 9.15, 10.07.

Example 10-6: 4-[4-Cyano-2-({[(2'R,4S)-6-(2-pyrazinyl)-2,3-dihydrospiro[chromene-4,1'-cyclopropan]-2'-yl]carbonyl}amino)phenyl]butanoic acid TLC: Rf 0.40 (dichloromethane:methanol=9:1);
¹H-NMR (CDCl₃): δ 1.25, 1.61, 1.68-1.88, 2.08-2.29, 2.40-2.87, 3.49, 4.25-4.41, 4.52, 6.97, 7.21, 7.29, 7.46, 7.61, 8.45, 8.62, 8.85, 8.97, 9.93.

Example 10-7: 4-{4-Cyano-2-[({(2'R,4S)-6-[5-(methylsulfonyl)-2-pyridinyl]-2,3-dihydrospiro[chromene-4,1'-cyclopropan]-2'-yl}carbonyl)amino]phenyl}butanoic acid TLC: Rf 0.48 (dichloromethane:methanol=9:1);
¹H-NMR (DMSO-d₆): δ1.61, 1.73, 1.80-1.92, 2.07-2.28, 2.38-2.75, 3.34, 4.06-4.20, 4.26-4.44, 6.96, 7.41, 7.57, 7.71, 7.88, 7.97, 8.18-8.36, 9.06, 9.91, 12.08.

Example 10-8: 4-{4-Cyano-2-[({(2'R,4S)-6-[5-(hydroxymethyl)-2-pyridinyl]-2,3-dihydrospiro[chromene-4,1'-cyclopropan]-2'-yl}carbonyl)amino]phenyl}butanoic acid TLC: Rf 0.42 (dichloromethane:methanol=9:1);
¹H-NMR (DMSO-d₆): δ 1.51-1.62, 1.63-1.87, 2.07-2.30, 2.53-2.75, 4.03-4.19, 4.25-4.39, 4.54, 5.29, 6.88, 7.40, 7.52-7.64, 7.70-7.94, 8.53, 9.92, 12.07.

Example 10-9: 4-[4-Cyano-2-({[(2'R,4S)-6-(5-fluoro-2-pyridinyl)-2,3-dihydrospiro[chromene-4,1'-cyclopropan]-2'-yl]carbonyl}amino)phenyl]butanoic acid TLC: Rf 0.64 (dichloromethane:methanol=9:1);
¹H-NMR (DMSO-d₆): δ 1.53-1.64, 1.65-1.88, 2.06-2.32, 2.40-2.80, 4.00-4.19, 4.24-4.40, 6.89, 7.40, 7.51-7.65, 7.71-7.84, 7.88, 8.00-8.05, 8.60, 9.92, 12.08.

Example 10-10: 4-[4-Cyano-2-({[(2'R,4S)-6-(6-methoxy-2-pyridinyl)-2,3-dihydrospiro[chromene-4,1'-cyclopropan]-2'-yl]carbonyl}amino)phenyl]butanoic acid TLC: Rf 0.50 (dichloromethane:methanol=9:1);
$^1$H-NMR (DMSO-$d_6$): δ 1.53-1.64, 1.66-1.79, 1.79-1.91, 2.03-2.30, 2.40-2.79, 3.94, 4.02-4.16, 4.26-4.40, 6.70, 6.89, 7.40, 7.48-7.62, 7.73, 7.80-7.89, 9.89, 12.07.

Example 10-11: 4-[4-Cyano-2-({[(2'R,4S)-6-(5-methoxy-2-pyridinyl)-2,3-dihydrospiro[chromene-4,1'-cyclopropan]-2'-yl]carbonyl}amino) phenyl]butanoic acid TLC: Rf 0.70 (dichloromethane:methanol=9:1);
$^1$H-NMR (CDCl$_3$): δ 1.16-1.30, 1.57, 1.70-1.83, 2.04-2.27, 2.52, 2.59-2.73, 2.74-2.92, 3.54, 3.92, 4.30, 4.48, 6.89, 7.19, 7.24-7.31, 7.38, 7.49, 7.52, 8.18, 8.83, 10.06.

Example 10-12: 4-[4-Cyano-2-({[(2'R,4S)-6-(5-methyl-1,2,4-oxadiazol-3-yl)-2,3-dihydrospiro[chromene-4,1'-cyclopropan]-2'-yl]carbonyl}amino)phenyl]butanoic acid TLC: Rf 0.69 (ethyl acetate:methanol=9:1);
$^1$H-NMR (CDCl$_3$): δ 1.19-1.31, 1.56, 1.70-1.88, 2.12-2.32, 2.42-2.84, 3.54, 4.37, 4.56, 6.92, 7.16-7.31, 7.71-7.82, 8.91, 9.84.

Example 11: 4-(4-Cyano-2-{[(2'R,4S)-2,3-dihydrospiro[1-benzopyran-4,1'-cyclopropane]-2'-carbonyl]amino}phenyl) butanoic acid The present compound having the following physical property values was obtained by performing the same procedures from Reference Example 10 to Example 1 using the compound produced in Reference Example 9, and the compound produced in Reference Example 3.
TLC: Rf 0.62 (chloroform:methanol=9:1);
$^1$H-NMR (CD$_3$OD): δ 1.66, 1.77-1.91, 2.08-2.28, 2.34, 2.48, 2.71, 4.16, 4.28, 6.74, 6.82-6.91, 7.06, 7.42, 7.48, 7.91.

Reference Example 18: (2'R,4S)-2'-{[2-(4-Ethoxy-4-oxobutyl)-5-fluorophenyl]carbamoyl}-2,3-dihydrospiro[1-benzopyran-4,1'-cyclopropane]-6-carboxylic acid The title compound having the following physical property values was obtained by performing the same procedures of Reference Example 7→Reference Example 9→Reference Example 10→Example 1, except that 5-fluoro-2-iodonitrobenzene was used instead of 3-nitro-4-bromobenzaldehyde.
$^1$H-NMR (DMSO-$d_6$): δ 1.12, 1.52-1.77, 2.12, 2.26, 2.51-2.62, 3.87-4.02, 4.12, 4.34, 6.86, 6.92, 7.20, 7.41, 7.47, 7.68, 9.68, 12.68.

Example 12

The present compounds having the following physical property values were obtained by performing the same procedures from Reference Example 12 to Example 1 using the compound produced in Reference Example 18 instead of the compound produced in Reference Example 11, using methylamine hydrochloride or a corresponding amine compound.

Example 12-1: 4-[4-Fluoro-2-({[(2'R,4S)-6-(methylcarbamoyl)-2,3-dihydrospiro[chromene-4,1'-cyclopropan]-2'-yl]carbonyl}amino)phenyl]butanoic acid TLC: Rf 0.69 (ethyl acetate:methanol=19:1);
$^1$H-NMR (CD$_3$OD): δ 1.62-1.87, 2.12-2.28, 2.32, 2.56-2.78, 2.90, 4.23, 4.34, 6.76-6.89, 7.20, 7.38-7.51, 7.54.

Example 12-2: 4-{4-Fluoro-2-[({(2'R,4S)-6-[(2-methoxyethyl)carbamoyl]-2, 3-dihydrospiro[chromene-4,1'-cyclopropan]-2'-yl}carbonyl)amino]phenyl}butanoic acid TLC: Rf 0.67 (ethyl acetate:methanol=19:1);
$^1$H-NMR (DMSO-$d_6$): δ 1.51-1.79, 2.06-2.22, 2.41-2.61, 3.25, 3.36-3.46, 4.07, 4.31, 6.83, 6.95, 7.19, 7.33, 7.43, 7.63, 8.42, 9.74, 12.06.

Example 12-3: 4-{4-Fluoro-2-[({(2'R,4S)-6-[(1-methyl-1H-pyrazol-4-yl)carbamoyl]-2,3-dihydrospiro[chromene-4,1'-cyclopropan]-2'-yl}carbonyl)amino]phenyl}butanoic acid TLC: Rf 0.64 (ethyl acetate:methanol=9:1);
$^1$H-NMR (CD$_3$OD): δ 1.66-1.86, 2.12-2.37, 2.57-2.70, 3.88, 4.25, 4.37, 6.81-6.92, 7.21, 7.45, 7.58, 7.63, 7.68, 8.00.

Reference Example 19: Ethyl 4-(2-{[[(1R,2R)-6'-(benzyloxy)-2',3'-dihydrospiro[cyclopropane-1,1'-indene]-2-carbonyl]amino}-4-cyanophenyl)butanoate The title compound having the following physical property values was obtained by performing the procedures of Reference Example 1→Reference Example 2→Reference Example 3→Reference Example 10, using 6-(benzyloxy)-2,3-dihydro-1H-inden-1-one instead of 4-chromanone.

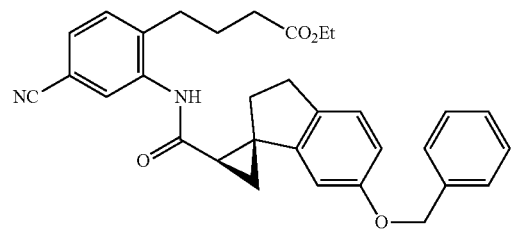 [SMILES: CCOC(=O)CCCc1ccc(C#N)cc1NC(=O)[C@@H]1C[C@]12CCc1ccc(OCc3ccccc3)cc12]

$^1$H-NMR (CDCl$_3$): δ 1.25, 1.38-1.45, 1.68-1.81, 1.82-1.87, 2.32-2.46, 2.57-2.67, 2.86-3.08, 3.82-3.92, 3.97-4.07, 5.00, 6.46, 6.77, 7.12, 7.17, 7.25-7.31, 7.32-7.43, 8.78, 9.15.

Example 13: 4-[2-({[(1R,2R)-6'-(Benzyloxy)-2',3'-dihydrospiro[cyclopropane-1,1'-inden]-2-yl]carbonyl}amino)-4-cyanophenyl]butanoic acid The present compound having the following physical property values was obtained by performing the procedures of Example 1 using the compound produced in Reference Example 19, instead of the compound produced in Reference Example 12.
TLC: Rf 0.53 (dichloromethane:methanol=10:1);
$^1$H-NMR (CDCl$_3$): δ 1.36-1.43, 1.66-1.77, 1.79-1.85, 2.31, 2.42-2.73, 2.84-3.09, 5.05, 6.49, 6.81, 7.13-7.21, 7.24-7.30, 7.32-7.47, 8.72, 8.92.

Example 14: 4-[4-Cyano-2-({[(1R,2R)-6'-hydroxy-2',3'-dihydrospiro[cyclopropane-1,1'-inden]-2-yl]carbonyl}amino)phenyl]butanoic acid 10% Palladium/carbon (12 mg) was added to a solution of the compound (40 mg) of Example 13 in ethyl acetate (3 mL) and 1,4-dioxane (1 mL). After replacing the atmosphere with hydrogen, the mixture was stirred at room temperature for 9 h. The reaction mixture was filtered using Celite, and the filtrate was concentrated under reduced pressure. The resulting residue was then purified by silica gel column chromatography to obtain the present compound (32 mg) having the following physical property values.

TLC: Rf 0.40 (dichloromethane:methanol=10:1);

$^1$H-NMR (CDCl$_3$): δ 1.36-1.43, 1.65-1.85, 2.32, 2.47-2.55, 2.58-2.76, 2.83-3.08, 6.37, 6.62, 7.06, 7.22, 7.25-7.37, 8.74, 8.92.

Reference Example 20: Ethyl 4-(4-cyano-2-{[(1R,2R)-6'-hydroxy-2',3'-dihydrospiro[cyclopropane-1,1'-indene]-2-carbonyl]amino}phenyl)butanoate The present compound having the following physical property values was obtained by performing the procedures of Example 14 using the compound produced in Reference Example 19, instead of the compound produced in Example 13.

$^1$H-NMR (CDCl$_3$): δ 1.24, 1.38-1.43, 1.70-1.87, 2.31-2.49, 2.58-2.67, 2.85-3.07, 3.89-4.01, 4.04-4.16, 4.49, 6.31, 6.58, 7.04, 7.17, 7.26-7.31, 8.78, 9.18.

Reference Example 21: Ethyl 4-[4-cyano-2-({(1R,2R)-6'-[(1-methyl-1H-pyrazol-4-yl)methoxy]-2',3'-dihydrospiro[cyclopropane-1,1'-indene]-2-carbonyl}amino)phenyl]butanoate Under a stream of nitrogen, cyanomethylenetributylphosphorane (0.06 mL) was dropped into a 0.2-mL toluene solution of the compound (30 mg) produced in Reference Example 20, and (1-methylpyrazol-4-yl)methanol (9.6 mg), and the mixture was stirred overnight at 100° C. The reaction mixture was concentrated under reduced pressure, and the resulting residue was purified by silica gel column chromatography to obtain the title compound (7 mg) having the following physical property values.

$^1$H-NMR (CDCl$_3$): δ 1.26, 1.39-1.42, 1.68-1.85, 2.28-2.51, 2.55-2.65, 2.83-3.05, 3.87-4.01, 4.04-4.18, 4.89, 6.40, 6.72-6.79, 7.06-7.38, 7.41, 7.51, 8.77, 9.13.

Example 15: 4-{4-Cyano-2-[({(1R,2R)-6'-[(1-methyl-1H-pyrazol-4-yl)methoxy]-2',3'-dihydrospiro[cyclopropane-1,1'-inden]-2-yl}carbonyl}amino]phenyl}butanoic acid The present compound having the following physical property values was obtained by performing the procedures of Example 1 using the compound produced in Reference Example 21, instead of the compound produced in Reference Example 12.

TLC: Rf 0.26 (dichloromethane:methanol=20:1);

$^1$H-NMR (DMSO-d$_6$): δ1.45-1.57, 1.66-1.79, 2.13-2.25, 2.26-2.75, 2.84-2.92, 3.81, 4.90, 6.51, 6.77, 7.09, 7.39, 7.47, 7.55, 7.77, 7.96.

Reference Example 22: Ethyl 4-[4-cyano-2-({(1R,2R)-6'-[2-(methylamino)-2-oxoethoxy]-2',3'-dihydrospiro[cyclopropane-1,1'-indene]-2-carbonyl}amino)phenyl]butanoate Potassium carbonate (33 mg) and tetrabutylammonium iodide (4.4 mg), and subsequently 2-chloro-N-methylacetamide (25.7 mg) were added at room temperature to a 0.5-mL DMF solution of the compound (50 mg) produced in Reference Example 20, and the reaction mixture was stirred overnight at 50° C. The reaction mixture was diluted with ethyl acetate, and, after adding a saturated ammonium chloride aqueous solution and water, extracted with ethyl acetate. The organic layer was washed with water and 20% brine, dried over anhydrous sodium sulfate, and concentrated under reduced pressure. The resulting residue was then purified by silica gel column chromatography (Yamazen Autopurification Device) to obtain the title compound (51 mg) having the following physical property values.

TLC: Rf 0.26 (hexane:ethyl acetate=4:1);

$^1$H-NMR (CDCl$_3$): δ 1.19, 1.39-1.44, 1.68-1.84, 1.86-1.89, 2.27-2.70, 2.84-3.08, 3.79-3.93, 3.95-4.06, 4.07, 4.44, 6.38, 6.55, 6.70, 7.13-7.20, 7.26-7.30, 8.75, 9.07.

Example 16: 4-{4-Cyano-2-[({(1R,2R)-6'-[2-(methylamino)-2-oxoethoxy]-2',3'-dihydrospiro[cyclopropane-1,1'-inden]-2-yl}carbonyl)amino]phenyl}butanoic acid The present compound having the following physical property values was obtained by performing the procedures of Example 1 using the compound produced in Reference Example 22, instead of the compound produced in Reference Example 12.

TLC: Rf 0.59 (ethyl acetate:methanol=9:1);

$^1$H-NMR (DMSO-d$_6$): δ 1.44-1.51, 1.56, 2.07-2.34, 2.66, 2.87, 6.54, 6.76, 7.12, 7.41, 7.56, 7.92, 8.01, 9.75, 12.12.

Example 17: 4-{4-Cyano-2-[({(1R,2R)-6'-[2-(dimethylamino)-2-oxoethoxy]-2',3'-dihydrospiro[cyclopropane-1,1'-inden]-2-yl}carbonyl)amino]phenyl}butanoic acid The present compound having the following physical property values was obtained by performing the procedures from Reference Example 22 to Example 1, using 2-chloro-N,N-dimethylacetamide instead of 2-chloro-N-methylacetamide.

TLC: Rf 0.54 (ethyl acetate:methanol=9:1);

$^1$H-NMR (DMSO-d$_6$): δ 1.47-1.58, 1.71, 2.08-2.32, 2.33-2.70, 2.82-2.91, 3.00, 4.74, 6.49, 6.70, 7.10, 7.41, 7.57, 7.91, 9.79, 12.16.

Reference Example 23: Ethyl 4-[4-cyano-2-({(1R,2R)-6'-[(trifluoromethanesulfonyl)oxy]-2',3'-dihydrospiro[cyclopropane-1,1'-indene]-2-carbonyl}amino)phenyl]butanoate

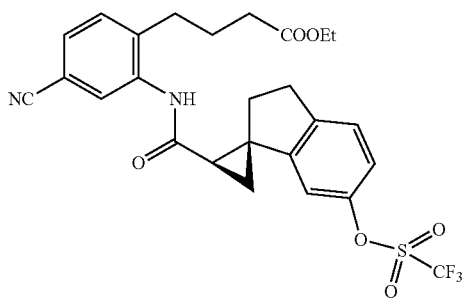 [SMILES: CCOC(=O)CCCc1ccc(C#N)cc1NC(=O)[C@@H]1C[C@]12CCc1ccc(OS(=O)(=O)C(F)(F)F)cc12]

In a nitrogen atmosphere, triethylamine (0.1 mL), and 1,1,1-trifluoro-N-phenyl-N-(trifluoromethylsulfonyl)methanesulfoneamide (128 mg) were added to a 2-mL dichloromethane solution of the compound (100 mg) produced in Reference Example 20, and the mixture was stirred at room temperature for 3 h. The mixture was further stirred at room temperature for 2 h after adding 1,1,1-trifluoro-N-phenyl-N-(trifluoromethylsulfonyl)methanesulfoneamide (128 mg) to the reaction liquid. The reaction liquid was then purified by silica gel column chromatography to obtain the title compound (130 mg) having the following physical property values.

$^1$H-NMR (CDCl$_3$): δ 1.22-1.29, 1.39-1.44, 1.70-1.83, 1.86-1.91, 2.34-2.51, 2.60-2.67, 2.95-3.14, 3.90-4.02, 4.05-4.16, 6.67, 7.03, 7.19, 7.21-7.31, 8.78, 9.19.

Reference Example 24: (1R,2R)-2-{[5-Cyano-2-(4-ethoxy-4-oxobutyl)phenyl]carbamoyl}-2',3'-dihydrospiro[cyclopropane-1,1'-indene]-6'-carboxylic acid

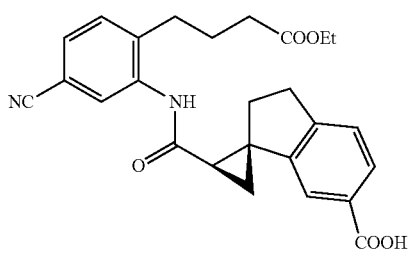 [SMILES: CCOC(=O)CCCc1ccc(C#N)cc1NC(=O)[C@@H]1C[C@]12CCc1ccc(C(=O)O)cc12]

The compound (120 mg) produced in Reference Example 23 was dissolved in DMSO (3 mL), and ultrasonically deaerated under reduced pressure. To the reaction liquid were then added 1,3-bis(diphenylphosphino)propane (dppp; 18 mg), palladium(II) acetate (10 mg), lithium chloride (92 mg), sodium formate (148 mg), diisopropylethylamine (0.34 mL), and an acetic anhydride (0.19 mL). The mixture was stirred at 90° C. for 4 h while replacing the atmosphere with carbon monoxide. After adding a 0.1 N hydrochloric acid aqueous solution, the reaction mixture was extracted with ethyl acetate, and the organic layer was dried over anhydrous sodium sulfate, and concentrated under reduced pressure. The resulting residue was then purified by silica gel column chromatography to obtain the title compound (40 mg) having the following physical property values.

$^1$H-NMR (CDCl$_3$): δ 1.18, 1.44-1.51, 1.64-1.79, 1.85-1.90, 2.35-2.48, 2.57-2.78, 2.99-3.17, 3.84-3.91, 4.03-4.11, 7.18, 7.24-7.36, 7.52, 7.89, 8.81, 9.29.

Example 18

The present compounds having the following physical property values were obtained by performing the procedures from Reference Example 12 to Example 1 using the compound produced in Reference Example 24 instead of the compound produced in Reference Example 11, using methylamine hydrochloride or a corresponding amine compound.

Example 18-1: 4-[4-Cyano-2-({[(1R,2R)-6'-(methylcarbamoyl)-2',3'-dihydrospiro[cyclopropane-1,1'-inden]-2-yl]carbonyl}amino)phenyl]butanoic acid

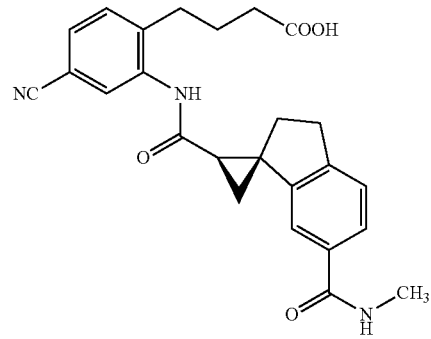 [SMILES: CNC(=O)c1ccc2c(c1)[C@]1(CC2)C[C@H]1C(=O)Nc1cc(C#N)ccc1CCCC(=O)O]

TLC: Rf 0.29 (dichloromethane:methanol=20:1);
$^1$H-NMR (CDCl$_3$): δ 1.26-1.31, 1.66-1.78, 1.82-1.87, 2.23-2.30, 2.34-2.48, 2.52-2.71, 2.91-3.03, 3.04, 3.13-3.27, 6.21-6.29, 7.17, 7.19-7.35, 7.70, 8.82, 9.56.

Example 18-2: 4-{4-Cyano-2-[({(1R,2R)-6'-[(2-methoxyethyl)carbamoyl]-2',3'-dihydrospiro[cyclopropane-1,1'-inden]-2-yl}carbonyl)amino]phenyl}butanoic acid

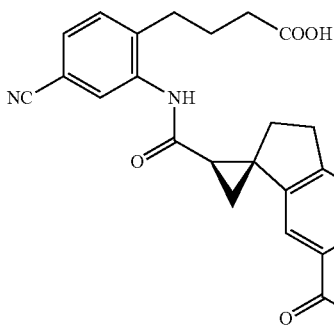

TLC: Rf 0.50 (dichloromethane:methanol=20:1);
$^1$H-NMR (CDCl$_3$): δ 1.25-1.31, 1.65-1.77, 1.81-1.86, 2.23-2.30, 2.35-2.47, 2.51-2.71, 2.91-3.03, 3.13-3.27, 3.41, 3.54-3.78, 6.62-6.67, 7.17, 7.19-7.30, 7.34, 7.66, 8.82, 9.51.

Example 18-3: 4-{4-Cyano-2-[({(1R,2R)-6'-[(1-methyl-1H-pyrazol-4-yl)carbamoyl]-2',3'-dihydrospiro[cyclopropane-1,1'-inden]-2-yl}carbonyl)amino]phenyl}butanoic acid

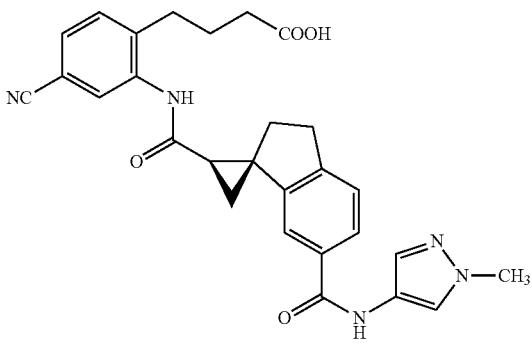 [SMILES: Cn1cc(NC(=O)c2ccc3c(c2)[C@]2(CC3)C[C@H]2C(=O)Nc2cc(C#N)ccc2CCCC(=O)O)cn1]

TLC: Rf 0.28 (dichloromethane:methanol=20:1);
¹H-NMR (CDCl₃): δ 1.26-1.34, 1.68-1.78, 1.81-1.88, 2.25-2.31, 2.43-2.72, 2.95-3.06, 3.17-3.23, 3.92, 7.16-7.33, 7.42, 7.52, 7.75, 7.86, 7.99, 8.83, 9.54.

Example 19: 4-[4-Cyano-2-({[(1R,2R)-6'-(3-pyridinyl)-2',3'-dihydrospiro[cyclopropane-1, 1'-inden]-2-yl]carbonyl}amino)phenyl]butanoic acid The present compound having the following physical property values was obtained by performing the procedures from Reference Example 15 to Example 1 using the compound produced in Reference Example 23. Pyridine-3-boronic acid was used instead of 4-fluorophenylboronic acid.
TLC: Rf 0.30 (dichloromethane:methanol=20:1);
¹H-NMR (CD₃OD): δ 1.58-1.66, 1.75-1.90, 2.25-2.45, 2.47-2.55, 2.68-2.79, 3.07-3.16, 7.15, 7.34-7.56, 7.98, 8.10, 8.52, 8.78.

Reference Example 25: (2'R,4S)-2'-{[5-Cyano-2-(4-ethoxy-4-oxobutyl)phenyl]carbamoyl}-7-fluoro-2,3-dihydrospiro[1-benzopyran-4,1'-cyclopropane]-6-carboxylic acid

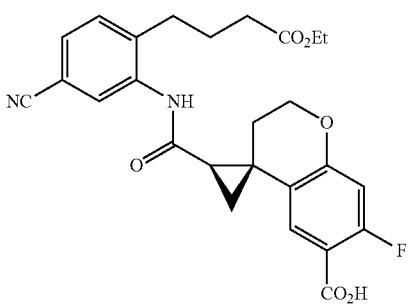 [SMILES: CCOC(=O)CCCc1ccc(C#N)cc1NC(=O)[C@@H]1C[C@]12CCOc1cc(F)c(C(=O)O)cc12]

The title compound having the following physical property values was obtained by performing the procedures of Reference Example 1→Reference Example 2→Reference Example 3→Reference Example 4→Reference Example 5→Reference Example 6→Reference Example 10→Reference Example 11, using 7-fluorochroman-4-one instead of 4-chromanone.

¹H-NMR (CDCl₃): δ 1.13, 1.66-1.78, 1.84-1.90, 2.25-2.35, 2.42-2.47, 2.58-2.67, 3.60-3.73, 3.78-3.90, 4.10-4.22, 4.35-4.44, 6.60, 7.19, 7.26-7.33, 7.50, 8.71, 9.37.

Example 20

The present compounds having the following physical property values were obtained by performing the procedures from Reference Example 12 to Example 1 using the compound produced in Reference Example 25 instead of the compound produced in Reference Example 11, using methylamine hydrochloride or a corresponding amine compound.

Example 20-1: 4-[4-Cyano-2-(({[(2'R,4S)-7-fluoro-6-(methylcarbamoyl)-2,3-dihydrospiro[chromene-4,1'-cyclopropan]-2'-yl]carbonyl}amino)phenyl]butanoic acid

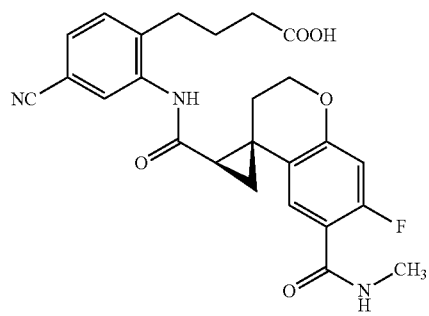 [SMILES: CNC(=O)c1cc2c(cc1F)OCC[C@]21C[C@H]1C(=O)Nc1cc(C#N)ccc1CCCC(=O)O]

TLC: Rf 0.74 (dichloromethane:methanol=10:1);
¹H-NMR (CDCl₃): δ 1.18-1.29, 1.50-1.62, 1.70-1.80, 2.05-2.15, 2.20-2.27, 2.44-2.76, 3.03, 3.54-3.60, 4.31-4.40, 4.54-4.59, 6.57, 6.82-6.95, 7.20, 7.24-7.33, 8.06, 8.88, 9.94.

Example 20-2: 4-{4-Cyano-2-[({(2'R,4S)-7-fluoro-6-[(2-methoxyethyl)carbamoyl]-2,3-dihydrospiro[chromene-4,1'-cyclopropan]-2'-yl}carbonyl)amino]phenyl}butanoic acid

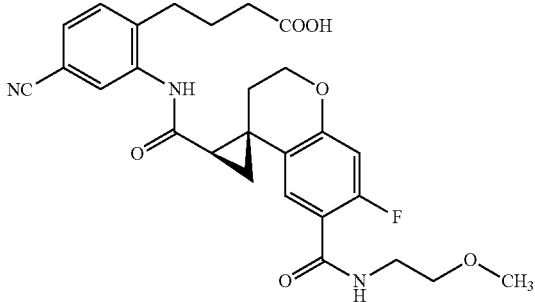 [SMILES: COCCNC(=O)c1cc2c(cc1F)OCC[C@]21C[C@H]1C(=O)Nc1cc(C#N)ccc1CCCC(=O)O]

TLC: Rf 0.49 (dichloromethane:methanol=10:1);
¹H-NMR (CDCl₃): δ 1.19-1.26, 1.58-1.64, 1.68-1.84, 2.05-2.29, 2.45-2.77, 3.39, 3.53-3.64, 3.65-3.72, 4.31-4.43, 4.54-4.62, 6.57, 7.17-7.34, 8.05, 8.88, 9.93.

Example 20-3: 4-[4-Cyano-2-({[(2'R,4S)-6-(ethyl-carbamoyl)-7-fluoro-2,3-dihydrospiro[chromene-4,1'-cyclopropan]-2'-yl]carbonyl}amino)phenyl]butanoic acid TLC: Rf 0.62 (hexane:ethyl acetate=1:3);
$^1$H-NMR (DMSO-d$_6$): δ 1.09, 1.55, 1.65-1.78, 2.02-2.28, 2.47, 2.60-2.71, 3.17-3.33, 4.12, 4.33, 6.73, 7.19, 7.41, 7.56, 7.88, 8.07, 9.89, 12.11.

Example 20-4: 4-[4-Cyano-2-({[(2'R,4S)-7-fluoro-6-(propylcarbamoyl)-2,3-dihydrospiro[chromene-4,1'-cyclopropan]-2'-yl]carbonyl}amino)phenyl]butanoic acid TLC: Rf 0.56 (hexane:ethyl acetate=1:2);
$^1$H-NMR (DMSO-d$_6$): δ 0.87, 1.42-1.58, 1.62-1.78, 2.04-2.23, 2.42, 2.60-2.69, 3.11-3.23, 4.12, 4.31, 6.73, 7.18, 7.41, 7.56, 7.88, 8.06, 9.90, 12.11.

Example 20-5: 4-[4-Cyano-2-({[(2'R,4S)-7-fluoro-6-(isopropylcarbamoyl)-2,3-dihydrospiro[chromene-4,1'-cyclopropan]-2'-yl]carbonyl}amino)phenyl]butanoic acid

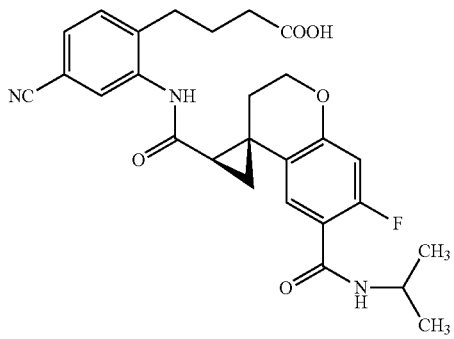 [SMILES: CC(C)NC(=O)c1cc2c(cc1F)OCC[C@]21C[C@H]1C(=O)Nc1cc(C#N)ccc1CCCC(=O)O]

TLC: Rf 0.68 (hexane:ethyl acetate=1:3);
$^1$H-NMR (DMSO-d$_6$): δ 1.13, 1.53, 1.63-1.79, 2.02-2.24, 2.46, 2.61-2.69, 3.96-4.18, 4.33, 6.72, 7.14, 7.41, 7.56, 7.80-7.92, 9.89, 12.11.

Example 21: 4-[4-Cyano-2-({[(2'R,4S)-6-fluoro-2,3-dihydrospiro[chromene-4, 1'-cyclopropan]-2'-yl]carbonyl}amino)phenyl]butanoic acid The present compound having the following physical property values was obtained by performing the procedures of Reference Example 1→Reference Example 2→Reference Example 3→Reference Example 10→Example 1 using 6-fluoro-4-chromanone instead of 4-chromanone.
TLC: Rf 0.38 (dichloromethane:methanol=10:1);
$^1$H-NMR (CDCl$_3$): δ 1.46-1.80, 2.18-2.24, 2.48-2.75, 4.09-4.32, 6.55, 6.75-6.87, 7.21, 7.25-7.34, 8.66, 9.00.

Reference Example 26: Ethyl 4-(2-{[(2'R,4S)-6-benzoyl-2,3-dihydrospiro[1-benzopyran-4, 1'-cyclopropane]-2'-carbonyl]amino}-4-cyanophenyl)butanoate Phenylboronic acid (10 mg), potassium carbonate (22 mg), and a [1,1'-bis(diphenylphosphino)ferrocene]palladium(II) dichloride dichloromethane complex (9 mg) were added to a 1-mL anisole solution of the compound (30 mg) produced in Reference Example 10, and the mixture was stirred at 80° C. for 3 h in a carbon monoxide atmosphere. A saturated sodium bicarbonate aqueous solution was poured into the reaction mixture, and the mixture was extracted with ethyl acetate. The organic layer was washed with saturated brine, dried over anhydrous magnesium sulfate, and concentrated under reduced pressure. The resulting residue was then purified by silica gel column chromatography (Yamazen Autopurification Device) to obtain the title compound (18 mg) having the following physical property values.
TLC: Rf 0.38 (hexane:ethyl acetate=1:1);
$^1$H-NMR (CDCl$_3$): δ 0.99, 1.61-1.80, 1.87, 2.27-2.36, 2.37-2.44, 2.61, 2.71, 3.43-3.56, 3.66, 3.81, 4.11-4.23, 4.32-4.42, 6.86, 7.19, 7.27, 7.42-7.62, 7.73, 8.73, 9.38.

Example 22: 4-[2-({[(2'R,4S)-6-Benzoyl-2,3-dihydrospiro[chromene-4,1'-cyclopropan]-2'-yl]carbonyl}amino)-4-cyanophenyl]butanoic acid The present compound having the following physical property values was obtained by performing the procedures of Example 1 using the compound produced in Reference Example 26, instead of the compound produced in Reference Example 12.
TLC: Rf 0.42 (dichloromethane:methanol=9:1);
$^1$H-NMR (DMSO-d$_6$): δ 1.53-1.64, 1.64-1.78, 2.10-2.30, 2.41-2.75, 3.20-3.49, 4.10-4.23, 4.33-4.45, 6.94, 7.36-7.45, 7.46-7.59, 7.60-7.73, 7.87, 9.89, 12.09.

Example 23

The present compounds having the following physical property values were produced by performing the same procedures from Reference Example 26 to Example 1, except that the phenylboronic acid was replaced with a correspond boronic acid.

Example 23-1: 4-[4-Cyano-2-({[(2'R,4S)-6-(cyclopropylcarbonyl)-2,3-dihydrospiro[chromene-4,1'-cyclopropan]-2'-yl]carbonyl}amino)phenyl]butanoic acid TLC: Rf 0.41 (dichloromethane:methanol=9:1);
$^1$H-NMR (CDCl$_3$): δ 1.02-1.38, 1.67-1.83, 2.06-2.38, 2.45-2.78, 4.33-4.45, 4.53-4.67, 6.89, 7.19, 7.25-7.30, 7.87, 7.98, 8.88, 9.85.

Example 23-2: 4-[2-({[(2'R,4S)-6-Acetyl-2,3-dihydrospiro[chromene-4,1'-cyclopropan]-2'-yl]carbonyl}amino)-4-cyanophenyl]butanoic acid TLC: Rf 0.40 (dichloromethane:methanol=9:1);
$^1$H-NMR (CDCl$_3$): δ 1.20-1.31, 1.70-1.85, 2.05-2.20, 2.23-2.33, 2.44-2.83, 4.33-4.45, 4.53-4.65, 6.85, 7.20, 7.28, 7.70, 8.06, 8.89, 9.83.

Reference Example 27: Ethyl 4-(4-cyano-2-{[(2'R,4S)-6-(methanesulfonyl)-2,3-dihydrospiro[1-benzopyran-4,1'-cyclopropane]-2'-carbonyl]amino}phenyl)butanoate In an argon atmosphere, sodium hydroxide (2.3 mg) was added to a 2-mL DMSO solution of L-proline (7 mg), and the mixture was stirred at room temperature for 30 min. To the reaction mixture were added the compound (40 mg)

produced in Reference Example 10, copper iodide (11 mg), and sodium methanesulfinate (37 mg), and the mixture was stirred at 100° C. for 1 h using a microwave reactor (Biotage, Ltd.). The reaction mixture was then purified by silica gel column chromatography (Yamazen Autopurification Device) to obtain the title compound (33 mg) having the following physical property values.

TLC: Rf 0.58 (hexane:ethyl acetate=1:3);

$^1$H-NMR (CDCl$_3$): δ 1.13, 1.66-1.80, 1.91, 2.20-2.45, 2.53-2.64, 2.67, 3.01, 3.45-3.60, 3.73-3.86, 4.11-4.20, 4.40, 6.96, 7.20, 7.30, 7.40, 7.63, 8.71, 9.44.

Example 24: 4-[4-Cyano-2-({[(2'R,4S)-6-(methylsulfonyl)-2,3-dihydrospiro[chromene-4,1'-cyclopropan]-2'-yl]carbonyl}amino)phenyl]butanoic acid The present compound having the following physical property values was obtained by performing the procedures of Example 1 using the compound produced in Reference Example 27, instead of the compound produced in Reference Example 12.

TLC: Rf 0.42 (dichloromethane:methanol=9:1);

$^1$H-NMR (DMSO-d$_6$): δ 1.53-1.64, 1.72, 1.80-1.87, 2.08-2.29, 2.35-2.74, 3.18, 4.05-4.20, 4.32-4.44, 7.02, 7.40, 7.42, 7.57, 7.64, 7.87, 9.95, 12.10.

Example 25: 4-[4-Cyano-2-({[(2'R,4S)-6-(cyclopropylsulfonyl)-2,3-dihydrospiro[chromene-4,1'-cyclopropan]-2'-yl]carbonyl}amino)phenyl]butanoic acid The present compound having the following physical property values was obtained by performing the procedures from Reference Example 27 to Example 1, using sodium cyclopropanesulfinate instead of sodium methanesulfinate.

TLC: Rf 0.40 (dichloromethane:methanol=9:1);

$^1$H-NMR (CDCl$_3$): δ 1.00-1.15, 1.20-1.43, 1.60-1.82, 2.09-2.35, 2.38-2.60, 2.63-2.75, 3.39, 4.35, 4.57, 6.95, 7.20, 7.29, 7.59, 7.71, 8.90, 9.64.

Reference Example 28: (2'R,4S)-7-(Benzyloxy)-2,3-dihydrospiro[1-benzopyran-4,1'-cyclopropane]-2'-carboxylic acid

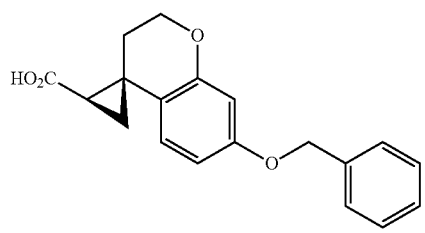 [SMILES: O=C(O)[C@@H]1C[C@]12CCOc1cc(OCc3ccccc3)ccc12]

The title compound having the following physical property values was obtained by performing the procedures of Reference Example 1→Reference Example 2→Reference Example 3, using 7-(benzyloxy)-2,3-dihydro-4H-chromen-4-one instead of 4-chromanone.

TLC: Rf 0.21 (hexane:ethyl acetate=1:1);

$^1$H-NMR (CDCl$_3$): δ 1.53-1.70, 2.07, 2.20, 4.20-4.09, 4.23-4.33, 5.01, 6.46, 6.52, 6.60, 7.27-7.44.

HPLC retention time: 12.2 min (CHIRALPAK IC 4.6 mm×250 mm hexane:ethyl acetate:formic acid=97:3:1).

Reference Example 29: Ethyl 4-(2-{[(2'R,4S)-7-(benzyloxy)-2,3-dihydrospiro[1-benzopyran-4,1'-cyclopropane]-2'-carbonyl]amino}-4-cyanophenyl)butanoate

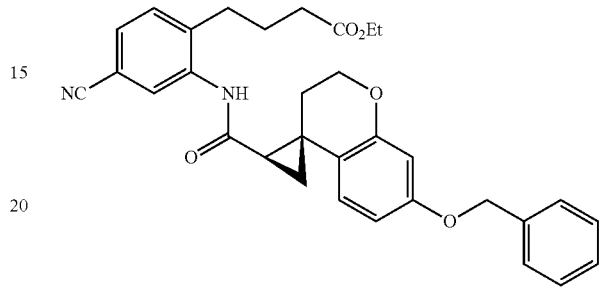

The title compound having the following physical property values was obtained by performing the procedures of Reference Example 10 using the compound produced in Reference Example 28, instead of the compound produced in Reference Example 6.

$^1$H-NMR (CDCl$_3$): δ 1.13, 1.54-1.61, 1.64-1.81, 2.22, 2.37-2.45, 2.51-2.66, 3.55-3.68, 3.72-3.86, 4.03, 4.16, 4.22-4.32, 4.99, 6.42-6.51, 6.73, 7.18, 7.28, 7.29-7.44, 8.72, 9.28.

Example 26: 4-[2-({[(2'R,4S)-7-(Benzyloxy)-2,3-dihydrospiro[chromene-4,1'-cyclopropan]-2'-yl]carbonyl}amino)-4-cyanophenyl]butanoic acid

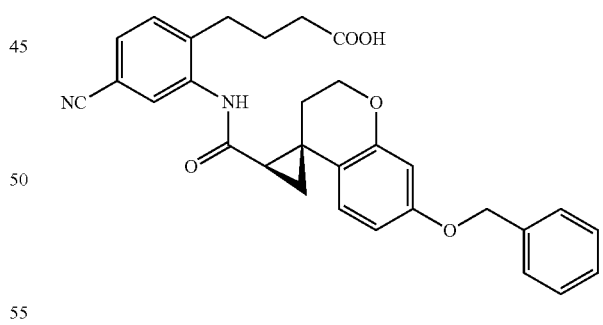

The present compound having the following physical property values was obtained by performing the procedures of Example 1 using the compound produced in Reference Example 29, instead of the compound produced in Reference Example 12.

TLC: Rf 0.42 (dichloromethane:methanol=9:1);

$^1$H-NMR (CDCl$_3$): δ 1.58, 1.68-1.84, 2.10-2.20, 2.36, 2.46, 2.50-2.75, 4.03-4.16, 4.20-4.32, 5.02, 6.48, 6.54, 6.71, 7.20, 7.27-7.45, 8.54, 8.82.

Reference Example 30: Ethyl 4-(4-cyano-2-{[(2'R, 4S)-7-hydroxy-2,3-dihydrospiro[1-benzopyran-4,1'-cyclopropane]-2'-carbonyl]amino}phenyl)butanoate

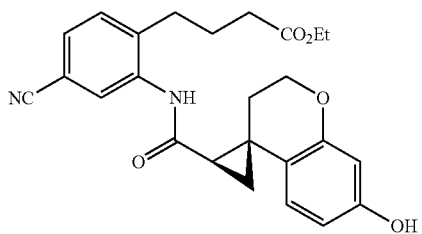 [SMILES: CCOC(=O)CCCc1ccc(C#N)cc1NC(=O)[C@@H]1C[C@]12CCOc1cc(O)ccc12]

ASCA-2 (trade name; 50% wet, 300 mg) was added to a mixed solution of the compound (650 mg) produced in Reference Example 29 in ethanol (50 mL) and ethyl acetate (10 mL), and the mixture was stirred at room temperature for 8 h in a hydrogen atmosphere. The reaction mixture was filtered using Celite (trade name), and the filtrate was concentrated under reduced pressure. The resulting residue was purified by silica gel column chromatography (Yamazen Autopurification Device), and washed with a tert-butyl methyl ether and hexane to obtain the title compound (368 mg) having the following physical property values.

TLC: Rf 0.28 (hexane:ethyl acetate=1:1);

$^1$H-NMR (CDCl$_3$): δ 1.16, 1.55-1.62, 1.66-1.80, 2.16-2.25, 2.38-2.47, 2.52-2.66, 3.60-3.73, 3.76-3.87, 4.04-4.15, 4.22-4.32, 4.63, 6.28-6.37, 6.69, 7.18, 7.28, 8.71, 9.28.

Example 27: 4-[4-Cyano-2-({[(2'R,4S)-7-(3-pyridinyl)-2,3-dihydrospiro[chromene-4,1'-cyclopropan]-2'-yl]carbonyl}amino)phenyl]butanoic acid The present compound having the following physical property values was obtained by performing the procedures of Reference Example 23→Reference Example 15→Example 1 using the compound produced in Reference Example 30 instead of the compound produced in Reference Example 20, using pyridine-3-boronic acid instead of 4-fluorophenylboronic acid.

TLC: Rf 0.39 (dichloromethane:methanol=9:1);

$^1$H-NMR (DMSO-d$_6$): δ 1.55-1.63, 1.65-1.80, 2.09-2.18, 2.21, 2.40-2.47, 2.53-2.77, 4.04-4.16, 4.28-4.38, 7.05, 7.15, 7.25, 7.41, 7.43-7.50, 7.57, 7.88, 8.02-8.08, 8.55, 8.85, 9.90, 12.10.

Example 28

The present compounds having the following physical property values were obtained by performing the procedures of Reference Example 23→Reference Example 24→Reference Example 12→Example 1 using the compound produced in Reference Example 30 instead of the compound produced in Reference Example 20, using methylamine hydrochloride or 2-methoxyethylamine.

Example 28-1: 4-[4-Cyano-2-({[(2'R,4S)-7-(methylcarbamoyl)-2,3-dihydrospiro[chromene-4,1'-cyclopropan]-2'-yl]carbonyl}amino)phenyl]butanoic acid

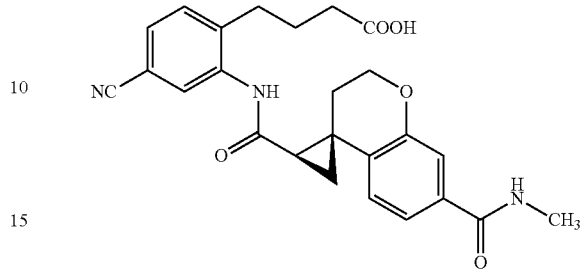

TLC: Rf 0.40 (dichloromethane:methanol=9:1);

$^1$H-NMR (DMSO-d$_6$): δ 1.56, 1.63-1.80, 2.02-2.15, 2.20, 2.42, 2.57-2.69, 2.74, 4.01-4.13, 4.23-4.37, 6.99, 7.24, 7.36, 7.40, 7.56, 7.86, 8.34, 9.89, 12.11.

Example 28-2: 4-{4-Cyano-2-[({(2'R,4S)-7-[(2-methoxyethyl)carbamoyl]-2,3-dihydrospiro[chromene-4,1'-cyclopropan]-2'-yl}carbonyl)amino]phenyl}butanoic acid

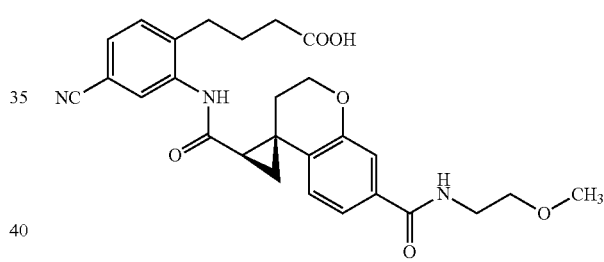

TLC: Rf 0.40 (dichloromethane:methanol=9:1);

$^1$H-NMR (CDCl$_3$): δ 1.63-1.89, 2.00-2.13, 2.25-2.47, 2.48-2.73, 2.78-2.93, 3.24-3.39, 3.51, 3.55-3.65, 3.85-4.06, 6.68, 6.79, 7.06, 7.20, 7.29, 7.98, 8.78, 9.84.

Example 29: 4-[2-({[(2'R,4S)-6-(Benzyloxy)-2,3-dihydrospiro[chromene-4,1'-cyclopropan]-2'-yl]carbonyl}amino)-4-cyanophenyl]butanoic acid The present compound having the following physical property values was obtained by performing the procedures of Reference Example 1→Reference Example 2→Reference Example 3→Reference Example 4→Reference Example 6→Reference Example 10-3 Example 1, using 6-(benzyloxy)-3,4-dihydro-2H-1-benzopyran-4-one instead of 4-chromanone. Iodoethane was used instead of iodomethane.

TLC: Rf 0.47 (dichloromethane:methanol=9:1);

$^1$H-NMR (CDCl$_3$): δ 1.46-1.55, 1.62-1.80, 2.12-2.18, 2.43-2.48, 2.51-2.76, 4.18-4.26, 4.95-5.07, 6.62, 6.75-6.80, 7.18, 7.28, 7.31-7.45, 8.68, 9.14.

Reference Example 31: Ethyl 4-(4-cyano-2-{[(2'R, 4S)-6-hydroxy-2,3-dihydrospiro[1-benzopyran-4,1'-cyclopropane]-2'-carbonyl]amino}phenyl)butanoate The title compound having the following physical property values was obtained by performing the procedures of Reference Example 1→Reference Example 2→Reference Example 3→Reference Example 4→Reference Example 6→Reference Example 10→Reference Example 30, using 6-(benzyloxy)-3,4-dihydro-2H-1-benzopyran-4-one instead of 4-chromanone.

TLC: Rf 0.66 (hexane:ethyl acetate=1:2);
$^1$H-NMR (CDCl$_3$): δ 1.16, 1.52-1.58, 1.66-1.83, 2.21, 2.41, 2.55-2.73, 3.65-3.78, 3.84-3.98, 4.02-4.13, 4.17-4.27, 4.54, 6.33, 6.55, 6.68, 7.19, 7.28, 8.74, 9.38.

Example 30: 4-[4-Cyano-2-({[(2'R, 4S)-6-hydroxy-2,3-dihydrospiro[chromene-4,1'-cyclopropan]-2'-yl]carbonyl}amino)phenyl]butanoic acid The present compound having the following physical property values was obtained by performing the procedures of Example 1, using the compound produced in Reference Example 31 instead of the compound produced in Reference Example 12.

TLC: Rf 0.38 (dichloromethane:methanol=9:1);
$^1$H-NMR (CD$_3$OD): δ 1.55-1.70, 1.77-1.90, 2.11-2.20, 2.33, 2.40-2.48, 2.67-2.78, 4.04-4.15, 4.17-4.26, 6.28, 6.53, 6.64, 7.41, 7.48, 7.90.

Example 31

The present compounds having the following physical property values were obtained by performing the procedures from Reference Example 21 to Example 1, using the compound produced in Reference Example 31 instead of the compound produced in Reference Example 20. 2-Oxazolemethanol or methanol was used instead of (1-methyl-pyrazol-4-yl)methanol.

Example 31-1: 4-[4-Cyano-2-({[(2'R,4S)-6-(1,3-oxazol-2-ylmethoxy)-2,3-dihydrospiro[chromene-4,1'-cyclopropan]-2'-yl]carbonyl}amino)phenyl]butanoic acid TLC: Rf 0.45 (dichloromethane:methanol=9:1);
$^1$H-NMR (CD$_3$OD): δ 1.58-1.76, 1.77-1.90, 2.09-2.21, 2.33, 2.47, 2.72, 4.08-4.17, 4.18-4.29, 5.11, 6.53, 6.70, 6.77, 7.21, 7.42, 7.48, 7.92, 7.96.

Example 31-2: 4-(4-Cyano-2-{[(2'R,4S)-6-methoxy-2,3-dihydrospiro[1-benzopyran-4,1'-cyclopropane]-2'-carbonyl]amino}phenyl)butanoic acid TLC: Rf 0.35 (ethyl acetate);
$^1$H-NMR (DMSO-d$_6$) δ 1.50-1.56, 1.65-1.80, 2.00-2.09, 2.20, 2.35-2.47, 2.55-2.60, 2.61-2.69, 2.70-2.75, 3.69, 3.92-4.04, 4.15-4.26, 6.43, 6.71, 7.40, 7.56, 7.85, 9.86, 12.11.

Example 32: 4-[4-Cyano-2-({[(2'R,4S)-7-(1,3-oxazol-2-ylmethoxy)-2,3-dihydrospiro[chromene-4,1'-cyclopropan]-2'-yl]carbonyl}amino)phenyl]butanoic acid The present compound having the following physical property values was obtained by performing the procedures from Reference Example 21 to Example 1, using the compound produced in Reference Example 30 instead of the compound produced in Reference Example 20. 2-Oxazolemethanol was used instead of (1-methylpyrazol-4-yl)methanol.

TLC: Rf 0.47 (dichloromethane:methanol=9:1);
$^1$H-NMR (CDCl$_3$): δ 1.58-1.68, 1.68-1.80, 2.03-2.15, 2.18-2.46, 2.41-2.50, 2.50-2.63, 2.64-2.83, 4.00-4.13, 4.20-4.31, 5.05, 5.17, 6.33, 6.48, 6.63, 7.10, 7.20, 7.28, 7.73, 8.62, 8.91.

Reference Example 32: Ethyl (2'R,4S)-7-methoxy-2,3-dihydrospiro[1-benzopyran-4,1'-cyclopropane]-2'-carboxylate

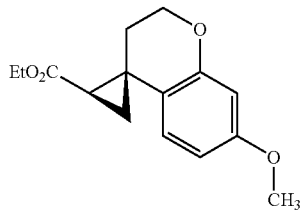 [SMILES: CCOC(=O)[C@@H]1C[C@]12CCOc1cc(OC)ccc12]

The procedures of Reference Example 4 were performed using the compound produced in Reference Example 28 instead of the compound produced in Reference Example 3. Iodoethane was used instead of iodomethane. Palladium hydroxide/carbon (10% wet, 0.2 g) was added to a 5-mL ethyl acetate solution of the resulting compound (2.1 g), and the mixture was stirred at room temperature for 30 min in a hydrogen atmosphere. The reaction mixture was filtered using Celite (trade name), and the filtrate was concentrated under reduced pressure. After adding potassium carbonate (1.46 g) to a 5-mL DMF solution of the resulting residue (1.31 g), iodomethane (1.5 g) was dropped, and the mixture was stirred overnight at room temperature. The reaction mixture was poured into ice water, and extracted with a hexane-ethyl acetate mixed solution. The organic layer was washed with water and saturated brine, dried over anhydrous sodium sulfate, concentrated under reduced pressure to obtain the title compound (1.38 g) having the following physical property values.

TLC: Rf 0.69 (hexane:ethyl acetate=1:1);
$^1$H-NMR (CDCl$_3$): δ 1.25, 1.55-1.60, 2.05, 2.13-2.20, 3.75, 4.05-4.20, 4.23-4.31, 6.38, 6.45, 6.59.

Example 33

The present compounds having the following physical property values were obtained by performing the procedures of Reference Example 5→Reference Example 6→Reference Example 10→Reference Example 11→Reference Example 12→Example 1, using the compound produced in Reference Example 32 instead of the compound produced in Reference Example 4, using methylamine hydrochloride or a corresponding amine compound.

Example 33-1: 4-[4-Cyano-2-({[(2'R,4S)-7-methoxy-6-(methylcarbamoyl)-2,3-dihydrospiro[chromene-4,1'-cyclopropan]-2'-yl]carbonyl}amino)phenyl]butanoic acid

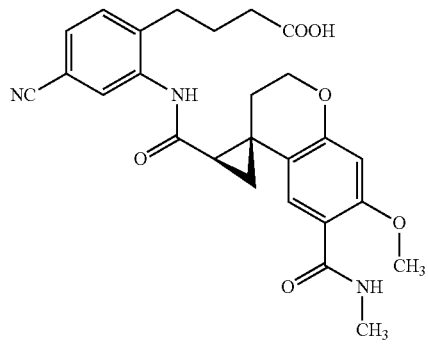 [SMILES: CNC(=O)c1cc2c(cc1OC)OCC[C@]21C[C@H]1C(=O)Nc1cc(C#N)ccc1CCCC(=O)O]

TLC: Rf 0.39 (dichloromethane:methanol=9:1);

$^1$H-NMR (DMSO-d$_6$): δ 1.42-1.60, 1.65-1.79, 2.00-2.29, 2.32-2.74, 2.77, 3.83, 4.05-4.17, 4.24-4.38, 6.54, 7.35-7.45, 7.55, 7.89, 7.98, 9.88, 12.12.

Example 33-2: 4-{4-Cyano-2-[({(2'R,4S)-7-methoxy-6-[(2-methoxyethyl)carbamoyl]-2,3-dihydrospiro[chromene-4,1'-cyclopropan]-2'-yl}carbonyl)amino]phenyl}butanoic acid

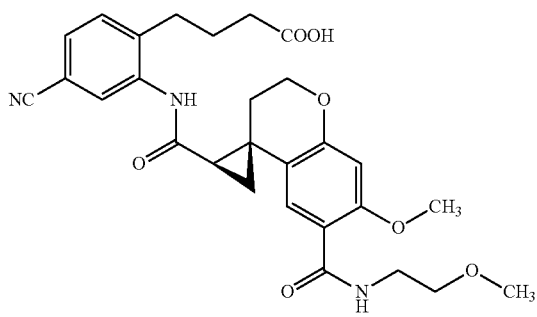 [SMILES: COCCNC(=O)c1cc2c(cc1OC)OCC[C@]21C[C@H]1C(=O)Nc1cc(C#N)ccc1CCCC(=O)O]

TLC: Rf 0.39 (dichloromethane:methanol=9:1);

$^1$H-NMR (DMSO-d$_6$): δ 1.46-1.60, 1.64-1.81, 2.00-2.29, 2.36-2.76, 3.27, 3.38-3.48, 3.85, 4.06-4.18, 4.25-4.36, 6.56, 7.40, 7.41, 7.55, 7.89, 8.09, 9.87, 12.10.

Example 33-3: 4-[4-Cyano-2-({[(2'R,4S)-6-(ethylcarbamoyl)-7-methoxy-2,3-dihydrospiro[chromene-4,1'-cyclopropan]-2'-yl]carbonyl}amino)phenyl]butanoic acid TLC: Rf 0.54 (hexane:ethyl acetate=1:3);

$^1$H-NMR (DMSO-d$_6$): δ 1.09, 1.47-1.58, 1.65-1.78, 2.04-2.23, 2.47, 2.60-2.69, 3.21-3.30, 3.84, 4.11, 4.30, 6.54, 7.35-7.44, 7.56, 7.89, 8.04, 9.88, 12.11.

Example 33-4: 4-[4-Cyano-2-({[(2'R,4S)-7-methoxy-6-(propylcarbamoyl)-2,3-dihydrospiro[chromene-4,1'-cyclopropan]-2'-yl]carbonyl}amino)phenyl]butanoic acid TLC: Rf 0.70 (hexane:ethyl acetate=1:3);

$^1$H-NMR (DMSO-d$_6$): δ 0.87, 1.41-1.58, 1.63-1.76, 2.00-2.23, 2.43, 2.59-2.70, 3.13-3.28, 3.84, 4.11, 4.29, 6.55, 7.32-7.42, 7.56, 7.90, 8.02, 9.88, 12.11.

Example 33-5: 4-[4-Cyano-2-({[(2'R,4S)-6-(isopropylcarbamoyl)-7-methoxy-2,3-dihydrospiro[chromene-4,1'-cyclopropan]-2'-yl]carbonyl}amino)phenyl]butanoic acid TLC: Rf 0.68 (hexane:ethyl acetate=1:3);

$^1$H-NMR (DMSO-d$_6$): δ 1.14, 1.46-1.58, 1.63-1.78, 2.01-2.22, 2.46, 2.58-2.69, 3.84, 3.97-4.16, 4.31, 6.55, 7.34-7.43, 7.56, 7.74, 7.89, 9.87, 12.09.

Example 34: 4-[4-Cyano-2-({[(2'R,4S)-7-methoxy-6-(5-methyl-1,3,4-oxadiazol-2-yl)-2,3-dihydrospiro[chromene-4,1'-cyclopropan]-2'-yl]carbonyl}amino)phenyl]butanoic acid The present compound having the following physical property values was obtained by performing the procedures of Reference Example 5→Reference Example 6→Reference Example 10→Reference Example 11→Reference Example 13→Example 1, using the compound produced in Reference Example 32 instead of the compound produced in Reference Example 4.

TLC: Rf 0.38 (dichloromethane:methanol=9:1);

$^1$H-NMR (CDCl$_3$): δ 1.16-1.27, 1.50-1.58, 1.66-1.85, 2.09-2.30, 2.42-2.83, 3.46, 3.85, 4.35, 4.55, 6.48, 7.19, 7.27, 7.68, 8.88, 9.90.

Example 35: 4-[4-Cyano-2-({[(2'R,4S)-6-(4-morpholinyl)-2,3-dihydrospiro[chromene-4,1'-cyclopropan]-2'-yl]carbonyl}amino)phenyl]butanoic acid Cesium carbonate (129 mg), [(2-dicyclohexylphosphino-2',4',6'-triisopropyl-1,1'-biphenyl)[2-(2-aminoethyl)phenyl]palladium(II) chloride (9 mg), and morpholine (34 mg) were added to a 1-mL DMF solution of the compound (72 mg) produced in Reference Example 10, and the mixture was stirred at 110° C. for 1 h using a microwave reactor (Biotage, Ltd.). A potassium carbonate aqueous solution was poured into the reaction mixture, and the mixture was extracted with ethyl acetate. The organic layer was washed with saturated brine, dried over anhydrous magnesium sulfate, and concentrated under reduced pressure. The resulting residue was purified by silica gel column chromatography (Yamazen Autopurification Device) to obtain an ethyl ester (46 mg). The present compound was obtained by performing the procedures of Example 1 using the ethyl ester, instead of the compound produced in Reference Example 12.

TLC: Rf 0.36 (dichloromethane:methanol=9:1);

$^1$H-NMR (DMSO-d$_6$): δ 1.45-1.55, 1.62-1.80, 2.00-2.10, 2.16-2.26, 2.32-2.77, 2.89-3.06, 3.65-3.78, 3.90-4.05, 4.13-4.26, 6.39, 6.67, 6.74, 7.40, 7.56, 7.84, 9.87, 12.08.

Reference Example 33: Ethyl 4-(4-cyano-2-{[(2'R, 3S)-5-iodo-2H-spiro[1-benzofuran-3,1'-cyclopropane]-2'-carbonyl]amino}phenyl)butanoate

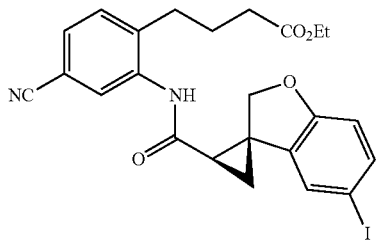 [SMILES: CCOC(=O)CCCc1ccc(C#N)cc1NC(=O)[C@@H]1C[C@]12COc1ccc(I)cc12]

The title compound having the following physical property values was obtained by performing the procedures of Reference Example 1→Reference Example 2→Reference Example 3→Reference Example 4→Reference Example 5→Reference Example 6→Reference Example 10, using 3-coumaranone instead of 4-chromanone. Iodoethane was used instead of iodomethane.

$^1$H-NMR (CDCl$_3$): δ 1.32, 1.57, 1.66-1.82, 2.36-2.70, 2.79, 3.95-4.22, 4.70, 6.60, 7.02, 7.20, 7.24-7.32, 7.38, 8.74, 9.40.

Example 36: 4-[4-Cyano-2-({[(2'R,3S)-5-(3-pyridinyl)spiro[1-benzofuran-3,1'-cyclopropan]-2'-yl]carbony}amino)phenyl]butanoic acid

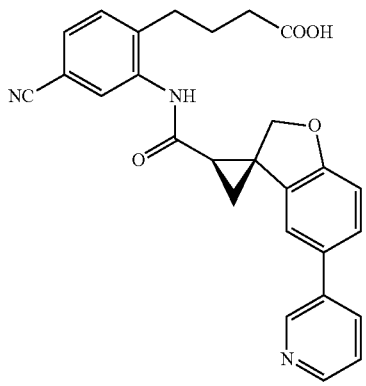 [SMILES: N#Cc1ccc(CCCC(=O)O)c(NC(=O)[C@@H]2C[C@]23COc2ccc(-c4cccnc4)cc23)c1]

The present compound having the following physical property values was obtained by performing the procedures from Reference Example 15 to Example 1 using the compound produced in Reference Example 33 instead of the compound produced in Reference Example 10. Pyridine-3-boronic acid was used instead of 4-fluorophenylboronic acid.

TLC: Rf 0.42 (dichloromethane:methanol=9:1);
$^1$H-NMR (CDCl$_3$): δ 1.06, 1.62-1.92, 2.58, 2.78, 2.94, 4.85, 6.47, 6.87, 7.01-7.40, 8.41, 8.61, 8.79, 9.75.

Example 37

The present compounds having the following physical property values were obtained by performing the procedures of Reference Example 11→Reference Example 12→Example 1, using the compound produced in Reference Example 33 instead of the compound produced in Reference Example 10, using methylamine hydrochloride or 2-methoxyethylamine.

Example 37-1: 4-[4-Cyano-2-({[(2'R,3S)-5-(methylcarbamoyl)spiro[1-benzofuran-3,1'-cyclopropan]-2'-yl]carbonyl}amino)phenyl]butanoic acid

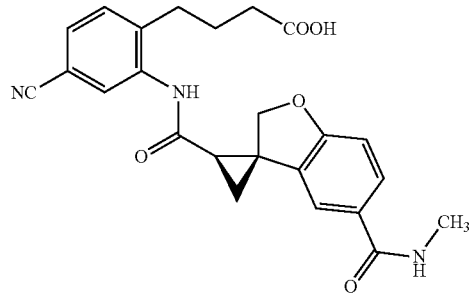 [SMILES: CNC(=O)c1ccc2c(c1)[C@]1(CO2)C[C@H]1C(=O)Nc1cc(C#N)ccc1CCCC(=O)O]

TLC: Rf 0.47 (dichloromethane:methanol=9:1);
$^1$H-NMR (CDCl$_3$): δ 1.57, 1.61-1.86, 2.30-2.73, 3.02, 3.22, 4.59, 4.73, 6.18, 6.76, 7.18, 7.20-7.32, 7.59, 8.70, 9.51.

Example 37-2: 4-{4-Cyano-2-[({(2'R,3S)-5-[(2-methoxyethyl)carbamoyl]spiro[1-benzofuran-3,1'-cyclopropan]-2'-yl}carbonyl)amino]phenyl}butanoic acid

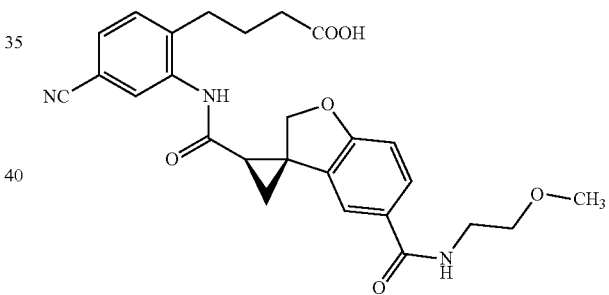

TLC: Rf 0.57 (dichloromethane:methanol=9:1);
$^1$H-NMR (CDCl$_3$): δ 1.58, 1.60-1.85, 2.30-2.75, 3.19, 3.41, 3.50-3.73, 4.61, 4.74, 6.47-6.62, 6.77, 7.19, 7.21-7.40, 7.56, 8.72, 9.47.

Reference Example 34: 6-Iodo-3,3-dimethyl-2,3-dihydro-1H-inden-1-one

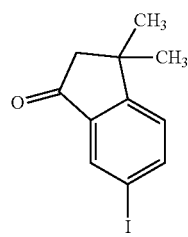

A sodium nitrite aqueous solution (4.5 mol/L, 4 mL) was dropped into a hydrochloric acid aqueous solution (5 mol/L, 15 mL) of 6-amino-3,3-dimethyl-indan-1-one (2.1 g) on ice, and the mixture was stirred for 30 min. After confirming the disappearance of the raw materials, a potassium iodide aqueous solution (4 mol/L, 6 mL) was dropped into the mixture on ice. The mixture was then stirred at room temperature for 1 h after adding acetonitrile (20 mL). A saturated sodium bicarbonate aqueous solution was added to the reaction mixture on ice, and the mixture was extracted with ethyl acetate. The organic layer was washed with a saturated sodium thiosulfate aqueous solution, dried over anhydrous sodium sulfate, and concentrated under reduced pressure. The resulting residue was then purified by silica gel column chromatography to obtain the title compound (2.66 g) having the following physical property values.

TLC: Rf 0.86 (hexane:ethyl acetate=1:1);
$^1$H-NMR (CDCl$_3$): δ 1.38-1.44, 2.59, 7.25-7.30, 7.90, 8.03.

Reference Example 35: Ethyl 4-(4-cyano-2-{[(1S,2R)-6'-iodo-3',3'-dimethyl-2',3'-dihydrospiro[cyclopropane-1,1'-indene]-2-carbonyl]amino}phenyl)butanoate

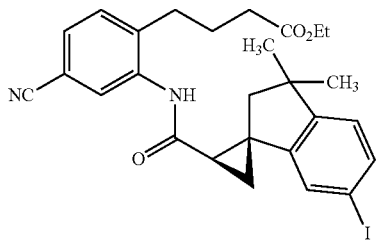 [SMILES: CCOC(=O)CCCc1ccc(C#N)cc1NC(=O)[C@@H]1C[C@]12CC(C)(C)c1ccc(I)cc12]

The title compound having the following physical property values was obtained by performing the procedures of Reference Example 1→Reference Example 2→Reference Example 3→Reference Example 10, using the compound produced in Reference Example 34 instead of 4-chromanone.

$^1$H-NMR (CDCl$_3$): δ 1.14-1.35, 1.44, 1.64-1.79, 1.79-1.88, 2.17, 2.28-2.50, 2.50-2.71, 3.83, 4.05, 6.91, 7.11, 7.19, 7.22-7.31, 7.45-7.53, 8.79, 9.28.

Example 38

The present compounds having the following physical property values were obtained by performing the procedures of Reference Example 11→Reference Example 12→Example 1, using the compound produced in Reference Example 35 instead of the compound produced in Reference Example 10, using methylamine hydrochloride or 2-methoxyethylamine.

Example 38-1: 4-[4-Cyano-2-({[(1S,2R)-6'-[(2-methoxyethyl)carbamoyl]-3',3'-dimethyl-2',3'-dihydrospiro[cyclopropane-1, 1'-inden]-2-yl]carbonyl}amino)phenyl]butanoic acid

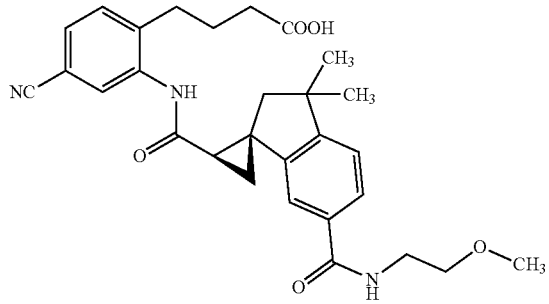 [SMILES: COCCNC(=O)c1ccc2c(c1)[C@@]1(C[C@H]1C(=O)Nc1cc(C#N)ccc1CCCC(=O)O)CC2(C)C]

TLC: Rf 0.64 (ethyl acetate:methanol=9:1);
$^1$H-NMR (CDCl$_3$): δ 1.28-1.40, 1.72, 1.86, 2.01-2.10, 2.14-2.23, 2.63, 3.16, 3.40, 3.53-3.81, 6.64, 7.17, 7.22-7.31, 7.33-7.44, 7.70, 8.82, 9.51.

Example 38-2: 4-[4-Cyano-2-({[(1S,2R)-3',3'-dimethyl-6'-(methylcarbamoyl)-2',3'-dihydrospiro[cyclopropane-1, 1'-inden]-2-yl]carbonyl}amino)phenyl]butanoic acid

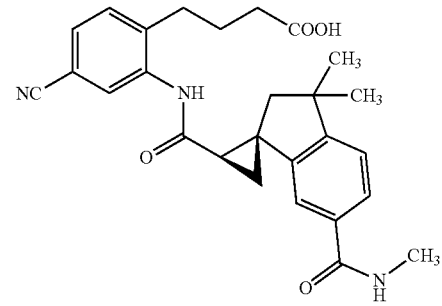 [SMILES: CNC(=O)c1ccc2c(c1)[C@@]1(C[C@H]1C(=O)Nc1cc(C#N)ccc1CCCC(=O)O)CC2(C)C]

TLC: Rf 0.55 (ethyl acetate:methanol=9:1);
$^1$H-NMR (CDCl$_3$): δ 1.29-1.42, 1.63-1.80, 1.83-1.90, 1.98-2.11, 2.11-2.24, 2.32-2.56, 2.57-2.69, 3.04, 3.19, 6.24, 7.11-7.19, 7.21-7.34, 7.72, 8.82, 9.57.

Example 39: 4-[4-Cyano-2-({[(1S,2R)-3',3'-dimethyl-6'-(3-pyridinyl)-2',3'-dihydrospiro[cyclopropane-1,1'-inden]-2-yl]carbonyl}amino)phenyl]butanoic acid

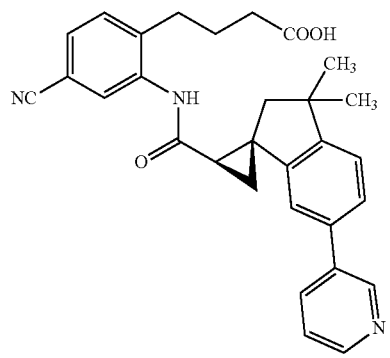 [SMILES: CC1(C)C[C@]2(C[C@H]2C(=O)Nc2cc(C#N)ccc2CCCC(=O)O)c2cc(-c3cccnc3)ccc21]

The present compound having the following physical property values was obtained by performing the procedures from Reference Example 15 to Example 1 using the compound produced in Reference Example 35 instead of the compound produced in Reference Example 10. Pyridine-3-boronic acid was used instead of 4-fluorophenylboronic acid.

TLC: Rf 0.62 (ethyl acetate:methanol=9:1);

$^1$H-NMR (CDCl$_3$): δ 0.59, 1.27-1.43, 1.55-1.69, 1.79, 2.18-2.38, 2.52-2.64, 2.64-2.91, 6.53, 7.16-7.35, 7.54, 8.39-8.50, 8.75-8.84, 9.35.

PHARMACOLOGICAL EXPERIMENT EXAMPLES

Pharmacological Experiment Example 1: EP$_4$ Antagonistic Activity Measurement Experiment Using Prostanoid Receptor Subtype Expressing Cells CHO cells expressing rat EP$_4$ receptor subtypes were prepared according to the methods of Nishigaki et al. (FEBS Letters, Vol. 364, p. 339-341, 1995), and used for experiment. Cultured subconfluent cells were detached, and suspended in an assay medium (MEM containing 1 mmol/L IBMX, 1% HSA) in a concentration of 1×10$^6$ cells/mL. For reaction, PGE$_2$ was added to the cell suspension (25 μL) in a final concentration of 10 nmol/L, either alone or as a 25-μL PGE$_2$ solution containing the test compound. After 30 minutes of reaction at room temperature, the amount of cAMP in the cells was quantified according to the method in the descriptions of the cAMP assay kit (CISBIO).

The antagonistic effect (IC$_{50}$ value) of the test compound was calculated as a value that represents an inhibition rate against a reaction with PGE$_2$ alone at 10 nM, a concentration that produces a submaximal cAMP producing effect.

The present compounds were shown to have strong EP$_4$ receptor antagonistic activity. As examples, Table 1 below shows the IC$_{50}$ values of some of the present compounds. The EP$_4$ receptor antagonistic activity was very weak, 2,800 nM, for the compound in Example 8-128 of WO2003/016254.

TABLE 1

| Example | EP$_4$ antagonistic activity (IC$_{50}$, nM) |
| --- | --- |
| 1 | 2.5 |
| 2-2 | 5.3 |
| 2-3 | 3.5 |
| 2-4 | 3.3 |
| 2-5 | 1.3 |
| 2-9 | 4.5 |
| 2-10 | 4.0 |
| 2-13 | 7.8 |
| 2-14 | 4.5 |
| 2-23 | 4.5 |
| 2-29 | 2.5 |
| 2-32 | 3.7 |
| 2-33 | 9.7 |
| 2-36 | 5.4 |
| 2-37 | 3.4 |
| 2-38 | 4.7 |
| 2-39 | 3.4 |
| 2-40 | 7.2 |
| 2-41 | 3.4 |
| 2-43 | 3.6 |
| 2-44 | 2.5 |
| 2-45 | 8.3 |
| 2-46 | 3.0 |
| 3 | 2.7 |
| 5 | 2.8 |
| 7-1 | 17 |
| 7-3 | 3.8 |
| 7-4 | 2.4 |
| 7-10 | 8.6 |
| 7-13 | 3.5 |
| 7-16 | 5.7 |
| 7-17 | 6.1 |
| 7-19 | 4.5 |
| 7-21 | 10 |
| 10-3 | 5.7 |
| 10-4 | 3.5 |
| 10-5 | 4.1 |
| 10-9 | 6.7 |
| 18-1 | 1.2 |
| 18-2 | 3.0 |
| 18-3 | 2.7 |
| 20-1 | 8.5 |
| 20-2 | 1.6 |
| 20-5 | 9.5 |
| 28-1 | 6.4 |
| 28-2 | 6.9 |
| 33-1 | 10 |
| 33-2 | 8.4 |
| 36 | 4.5 |
| 37-1 | 7.2 |
| 37-2 | 6.2 |
| 38-1 | 5.4 |
| 38-2 | 4.3 |
| 39 | 5.7 |

Pharmacological Experiment Example 2: Pharmacokinetics Test (Hepatic Microsome Stability Test)

(1) Preparation of Subject Substance Solution

A DMSO solution of the subject substance (the present compound, and a comparative compound) (10 mmol/L; 5 μL) was diluted with a 50% acetonitrile aqueous solution (195 μL) to prepare a 250 μmol/L subject substance solution.

(2) Preparation of Standard Sample (Sample Immediately after Reaction)

First, 245 μL of a 0.1 mol/L phosphate buffer (pH 7.4) containing an NADPH-Co-Factor (BD-Bioscience), and 1 mg/mL of human hepatic microsome was added to a reaction vessel that had been heated to 37° C. with a water bath, and the solution was preincubated for 5 min. To this solution was added 5 μL of the subject substance solution to start a reaction (final concentration of 1 μmol/L). Immediately after the reaction was started, 20 μL of the reaction solution was collected, and added to 180 μL of acetonitrile (containing candesartan as an internal standard) to quench the reaction. The quenched solution (20 μL; a sample solution immediately after the reaction) was stirred with 50% acetonitrile (180 μL) on a deproteinization filter plate, and subjected to suction filtration. The filtrate was then obtained as a standard sample.

(3) Preparation of Reaction Sample (Sample after 60 Min from Reaction)

The reaction solution was incubated at 37° C. for 60 min, and 20 μL of the reaction solution was collected, and added to 180 μL of acetonitrile (containing candesartan as an internal standard) to quench the reaction. The quenched solution (20 μL; a sample solution after 60 minutes of reaction) was stirred with 50% acetonitrile (180 μL) on a deproteinization filter plate, and subjected to suction filtration. The filtrate was then obtained as a reaction sample.

(4) Evaluation Method

Using peak areas from LC-MS/MS, the subject substance remaining rate (%) was calculated from the mass (X) of the subject substance in the standard sample, and the mass (Y) of the subject substance in the reaction sample, according to the following formula.

Remaining rate (%)=(Y/X)×100

X: Mass of the subject substance in standard sample (ratio=peak area of subject substance/peak area of internal standard)

Y: Mass of the subject substance in reaction sample (ratio=peak area of subject substance/peak area of internal standard)

(5) Result

The present compounds were shown to have high stability against human hepatic microsome (high remaining rate (%)). As examples, Table 2 below shows the remaining rates of some of the present compounds. The remaining rate was 35% for the compound in Example 6-117 of WO2003/016254.

TABLE 2

| Example | Remaining rate (%) |
|---|---|
| 1 | 94 |
| 2-2 | 97 |
| 2-3 | 91 |
| 2-4 | 86 |
| 2-5 | 93 |
| 2-9 | 92 |
| 2-10 | 94 |
| 2-13 | 100 |
| 2-14 | 96 |
| 2-23 | 100 |
| 2-29 | 80 |
| 2-32 | 85 |
| 2-33 | 89 |
| 2-36 | 100 |
| 2-37 | 97 |
| 2-38 | 100 |
| 2-39 | 90 |
| 2-40 | 100 |
| 2-41 | 100 |
| 2-43 | 100 |
| 2-44 | 100 |
| 2-45 | 100 |
| 2-46 | 90 |
| 3 | 100 |
| 5 | 80 |
| 7-1 | 81 |
| 7-3 | 72 |
| 7-4 | 71 |
| 7-10 | 89 |
| 7-13 | 95 |
| 7-16 | 80 |
| 7-17 | 82 |
| 7-19 | 100 |
| 7-21 | 76 |
| 10-3 | 87 |
| 10-4 | 73 |
| 10-5 | 86 |
| 10-9 | 75 |
| 18-1 | 90 |
| 18-2 | 100 |
| 18-3 | 91 |
| 20-1 | 88 |
| 20-2 | 77 |
| 20-5 | 100 |
| 28-1 | 91 |
| 28-2 | 100 |
| 33-1 | 98 |
| 33-2 | 100 |
| 36 | 93 |
| 37-1 | 77 |
| 37-2 | 87 |
| 38-1 | 69 |
| 38-2 | 89 |
| 39 | 78 |

Pharmacological Experiment Example 3:
Anti-Tumor Effect in Allograft Model of Mouse Colorectal Cancer Cell Line CT26

The anti-tumor effect of the present compound was evaluated in an allograft model of the mouse colorectal cancer cell line CT26. CT26 was cultured in a $CO_2$ incubator, using an RPMI-1640 medium containing 10 vol % inactivated fetal bovine serum (FBS), 100 units/mL of penicillin, and 100 g/mL of streptomycin. On the day of transplant, CT26 was harvested after removing the culture supernatant, and washing the cells with phosphate buffer (hereinafter, "PBS"). The harvested CT26 cells were suspended in Hank's buffer to obtain transplant cells. The transplant cells ($3 \times 10^5$) were then subcutaneously transplanted to the right back of a female Balb/C mouse (Charles River Laboratories Japan Inc.) under anesthesia. The present compound was orally administered in a dose of 10 mg/kg, once on the day of transplant, and twice a day from the next day. For the control group, distilled water was administered for the same duration as in the present compound-administered group. The tumor volume ($mm^3$) was determined by calculating a relative tumor volume from the measured tumor lengths along the minor axis and major axis using a digital caliper, according to the following formulae 1 and 2.

Tumor volume=[(minor axis)$^2$×major axis]/2

Relative tumor volume=medium value of tumor volumes of each group after 21 days from transplant/medium value of tumor volume of control group after 21 days from transplant The present compounds had a tumor growth inhibitory effect. As examples, FIG. 1 shows the relative tumor volumes for Examples 2-2 and 2-13.

PREPARATION EXAMPLES

Preparation Example 1

The following components were mixed and punched using an ordinary method to obtain 10,000 tablets containing 10 mg of the active component per tablet.

4-[4-Cyano-2-({[(2'R,4S)-6-(methylcarbamoyl)-2,3-dihydrospiro[chromene-4,1'-cyclopropan]-2'-yl]carbonyl}amino)phenyl]butanoic acid: 100 g
Carboxymethyl cellulose calcium (disintegrator): 20 g
Magnesium stearate (lubricant): 10 g
Microcrystalline cellulose: 870 g Preparation Example 2

The following components were mixed using an ordinary method, and filtered through a dust filter. The preparation was charged into ampules in 5-ml portions, and heat sterilized with an autoclave to obtain 10,000 ampules containing 20 mg of the active component per ampule.

4-[4-Cyano-2-({[(2'R,4S)-6-(methylcarbamoyl)-2,3-dihydrospiro[chromene-4,1'-cyclopropan]-2'-yl]carbonyl}amino)phenyl]butanoic acid: 200 g
Mannitol: 20 g
Distilled water: 50 L

INDUSTRIAL APPLICABILITY

The present compound has antagonistic activity against the $EP_4$ receptor, and is effective for the prevention and/or treatment of diseases caused by $EP_4$ receptor activation.

The invention claimed is:
1. A compound that is 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, which is represented by the following structural formula:

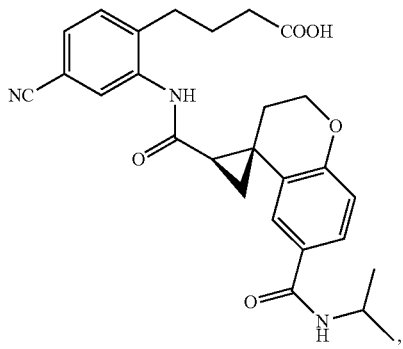 [SMILES: CC(C)NC(=O)c1ccc2c(c1)[C@]1(CCO2)C[C@H]1C(=O)Nc1cc(C#N)ccc1CCCC(=O)O]

a salt thereof, or a solvate thereof.

2. A compound that is 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, which is represented by the following structural formula:

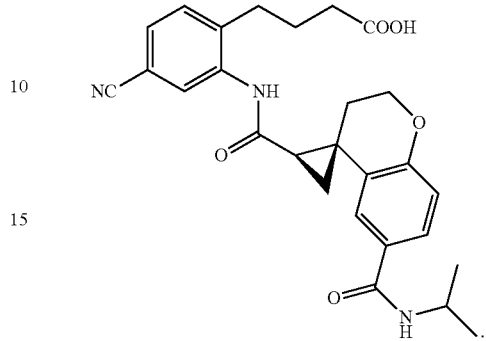

* * * * *